US012171795B2

(12) United States Patent
Mueller et al.

(10) Patent No.: US 12,171,795 B2
(45) Date of Patent: Dec. 24, 2024

(54) RECOMBINANT RHABDOVIRUS ENCODING FOR A CD80 EXTRACELLULAR DOMAIN Fc-FUSION PROTEIN

(71) Applicant: Boehringer Ingelheim International GmbH, Ingelheim am Rhein (DE)

(72) Inventors: Philipp Mueller, Mittelbiberach (DE); Klaus Erb, Mittelbiberach (DE); Patrik Erlmann, Goetzens (AT); Guido Wollmann, Innsbruck (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 576 days.

(21) Appl. No.: 17/336,351

(22) Filed: Jun. 2, 2021

(65) Prior Publication Data

US 2021/0379130 A1 Dec. 9, 2021

(30) Foreign Application Priority Data

Jun. 3, 2020 (EP) .................................... 20178032

(51) Int. Cl.

*A61K 35/766* (2015.01)
*A61K 45/06* (2006.01)
*C07K 14/705* (2006.01)

(52) U.S. Cl.

CPC ............ *A61K 35/766* (2013.01); *A61K 45/06* (2013.01); *C07K 14/70532* (2013.01); *C07K 2319/02* (2013.01); *C07K 2319/30* (2013.01)

(58) Field of Classification Search

CPC .................. A61K 35/766; A61K 45/06; C07K 14/70532; C07K 2319/02; C07K 2319/30
See application file for complete search history.

(56) References Cited

U.S. PATENT DOCUMENTS

| | | | | |
|---|---|---|---|---|
| 2009/0175906 | A1* | 7/2009 | Kalyan | C12N 7/00 435/235.1 |
| 2016/0296572 | A1* | 10/2016 | Van Den Pol | A61P 35/00 |
| 2022/0227833 | A1* | 7/2022 | Song | A61P 37/02 |

FOREIGN PATENT DOCUMENTS

| | | | |
|---|---|---|---|
| CN | 108728488 | A | 11/2018 |
| WO | 2001254450 | | 4/2001 |
| WO | 2005035773 | | 4/2005 |
| WO | 20080016893 | A1 | 2/2008 |
| WO | 2009082664 | A2 | 7/2009 |
| WO | 2013127729 | A1 | 9/2013 |
| WO | 2015025018 | A1 | 2/2015 |
| WO | 2015025019 | A1 | 2/2015 |
| WO | 2016023858 | A1 | 2/2016 |
| WO | 2017143449 | A1 | 8/2017 |
| WO | 2017181152 | | 10/2017 |
| WO | 2017197525 | A1 | 11/2017 |
| WO | 2018170026 | A2 | 9/2018 |
| WO | 2020047087 | A1 | 3/2020 |

OTHER PUBLICATIONS

Schildberg, Immunity, Cohinitory Pathways in the B7-CD28 Ligand-Receptor Family, vol. 44, 2017.
Lichty, perspectives, Ging Viral with Viral cancer Immunotherapy, vol. 14, 2014.
Liu, Combination B7-Fc Fusion Protein Treatment and Treg Cell Deptetion Therapy, Clin. Cancer Research. vol. 11, p. 492-498, 2005.
Reul, Dissertation, Viral gene transfer systems for cancer immunotherapy, 2018.
Smith, Cancer, Immunotherapy, Cancer-Vaccines, Genetic Engineering of Hematopoietic Stem Cells to Generate Invariant Natural Killer y Cells, 2018.
Pickup, NIH, The roles of TGFß in the tumor microenvironment, 2013.
Deng, MABS, Preclinical Pharmacokinetics, pharmacodynamics, tissue distribution, and tumor penetration, vol. 8, 2016.
Calon, Nature Genetics, Stromal geneexpression defines poor prognosis subtypes in colorectal cancer, vol. 47, 2013.
Boyerinas, Cancer immunol. Res., Antibody-dependent cellular cytotoxicity, vol. 3, 2015.
Ryner, Clinical Cancer Research, Upregulation of Periostatin and reactive stroma is associated with primary chemoresistance, 2015.
Tothill, Clinical Cancer Research, Novel Molecular Subtypes of Serous and Endometroid Ovarian Cancer, vol. 14, 2008.
Stewart, Cancer Immunol. Research, Id and Characterization of MEDI4736, vol. 3, 2016.
Ibrahim, PD-LI Blockade for Treatment, Semin, Oncol.,2015.
Walker, J. of Gem. Virology, ICTV Virus Taxonomy Profile, 2018.
Muik, Cancer Research, Re-engineering Vesicular Stomatitis Virus to Abrogate Neurotoxicity, 2014.
Penheiter, Current Gene Therapy, The Sodium Iosise Supporter, vol. 12 , 2012.
Karlin, Proc. Natl., Acad. Science, Methods for assessing the statisitcal significance of molecular sequence features, vol. 87, 1990.
Altschul, J. Molecular Biol., Basic Local Alignment Search tool, vol. 15, 1990.
Altschul, Nucleic Acids Research, Gapped BLAST and PSI BLAST, vol. 25, 1997, p. 3389-3402.
Torelli, Cabios, ADVANCE and ADAM: 2 algorithms for the analysis of global similarity between homologous informational sequences, 1994.
Pearson, Proc. Natl. Acad, Sci, Improved Tools for Biological sequence Comparison, vol. 85, 1988.
Schnell, J. of Virology, The minimal Conserved Transcription stop start signal promotes stable expression of a foreign gene, vol. 70, 1996.

(Continued)

*Primary Examiner* — Shin Lin Chen
*Assistant Examiner* — Khoa Nhat Tran
(74) *Attorney, Agent, or Firm* — Wendy M. Gombert

(57) ABSTRACT

The present invention relates to the field of oncolytic viruses and in particular to a recombinant rhabdovirus, such as vesicular stomatitis virus encoding in its genome for a CD80 extracellular domain Fc-fusion protein. The invention is further directed to the use of the recombinant virus in the treatment of cancer, and also to methods for producing such viruses.

15 Claims, 24 Drawing Sheets

Specification includes a Sequence Listing.

(56) References Cited

OTHER PUBLICATIONS

Higgins, Methods in Enzymology, Using Clustal for Multiple Signal Alignments, vol. 266, 1996.
Li, Int. J. of Molecular Sciences, A mini Review for Cancer immunotherapy, 2016.
Hamid, NE J. of Medicine, Safety and Tumor responses, 2013.
International Search Report and Written Opinion mailed on Aug. 24, 2021 for PCT/EP2021/064728.
Abstract cited herein for CN 108728488 dated 2018.
Reul, Viral gene transfer systems for cancer immunotherapy: semireplication-competent VSV and receptor-targeted AAV for the delivery of immunomodulatory proteins, vom Fachbereich Biologie der Technischen Universitat Darmstadt zur Erlangung des akademischen Grades, 2018, vol. 1, p. 1-166.
Smith, Genetic Engineering of Hematopoietic Stem cells to generate invariant Natural Killer T Cells, Cancer-Immunotherapy, Cancer Vaccines I, vol. 24, 2016, p. 1.
Liu, Combination B7-Fc Fusion Protein Treatment and Treg Cell Depletion Therapy, Cancer Therapy: Preclinical, 2005, vol. 23, p. 8492-8502.

* cited by examiner

FIG.3A-B

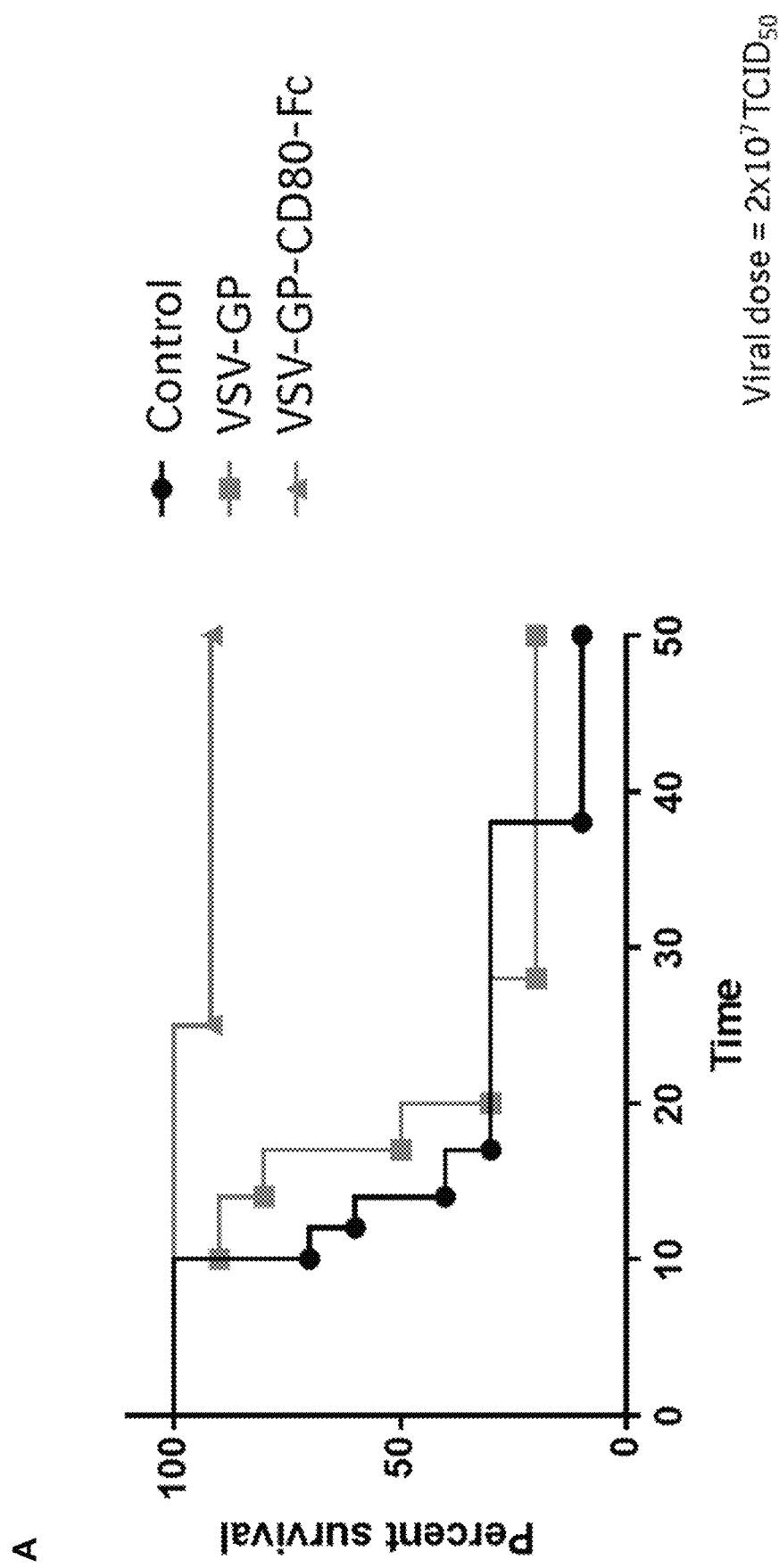
FIG.5A-B

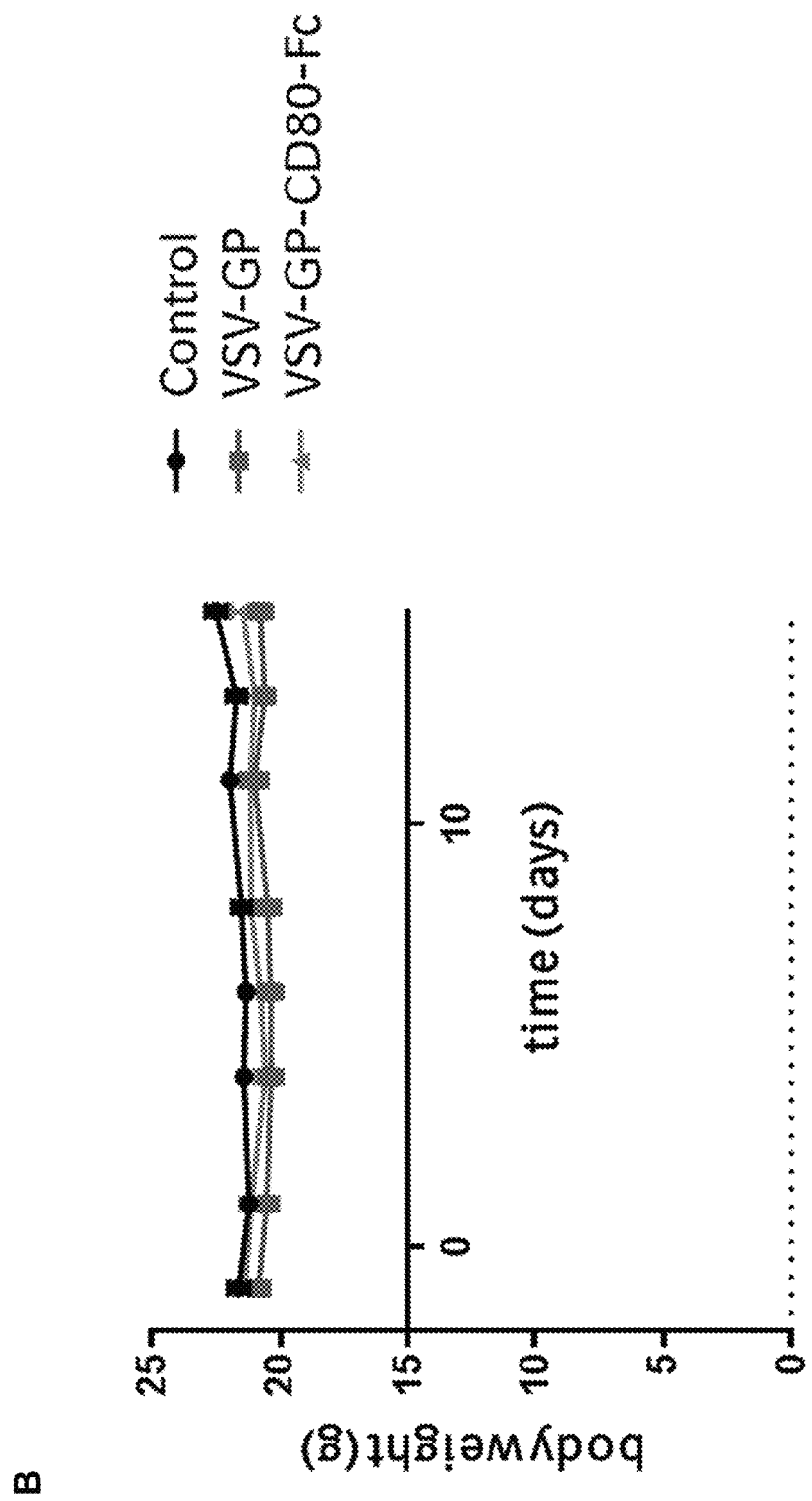
FIG. 5A-B cont.

FIG.6A-C
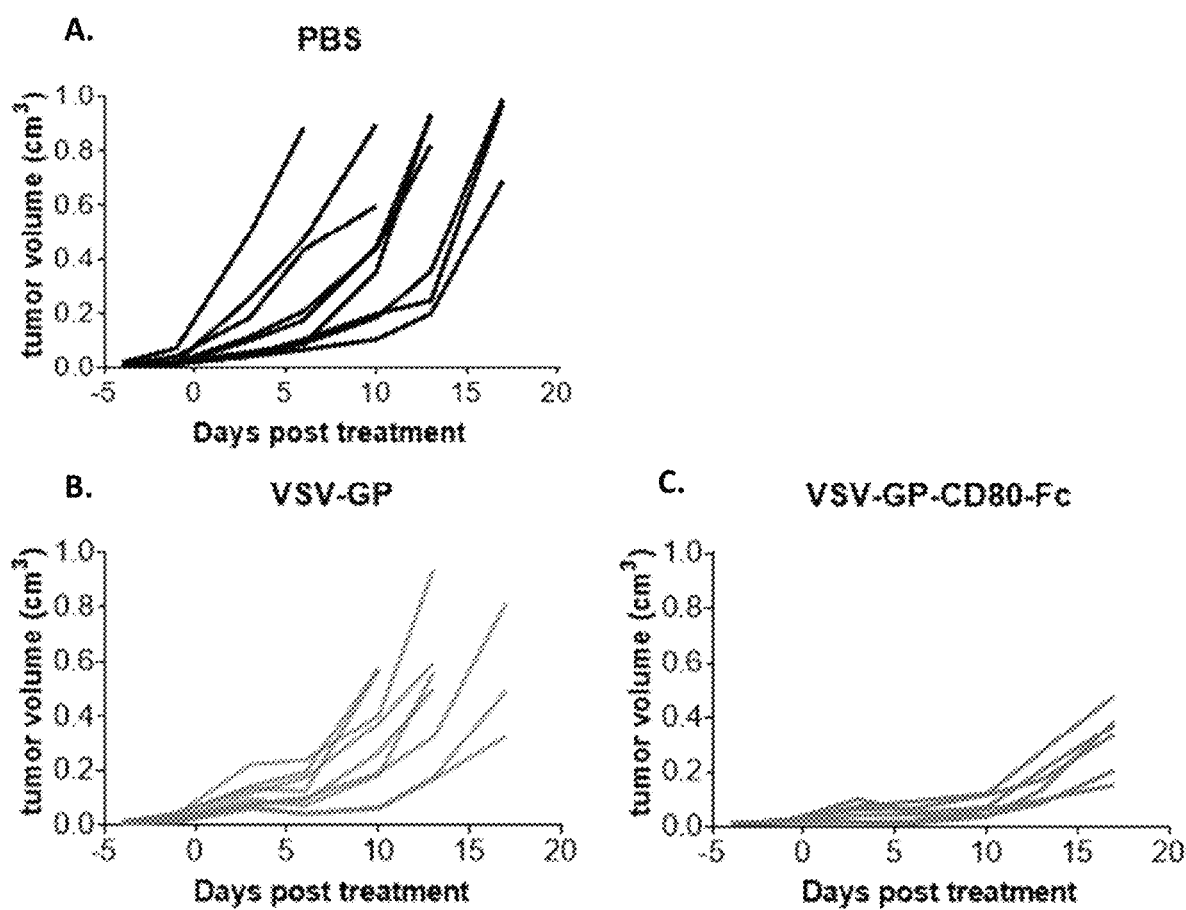

FIG.7A-B
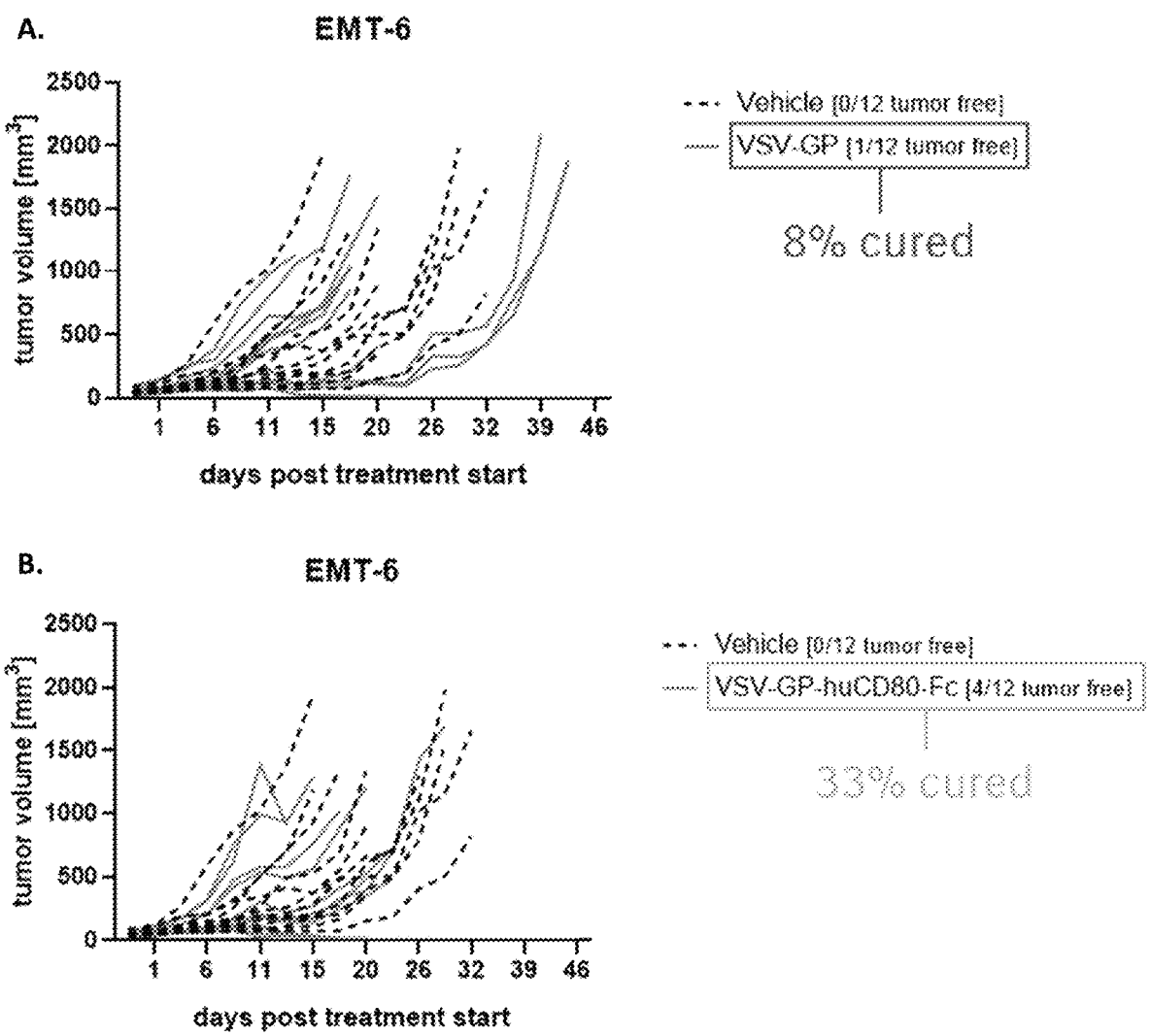

FIG. 13A-D
A
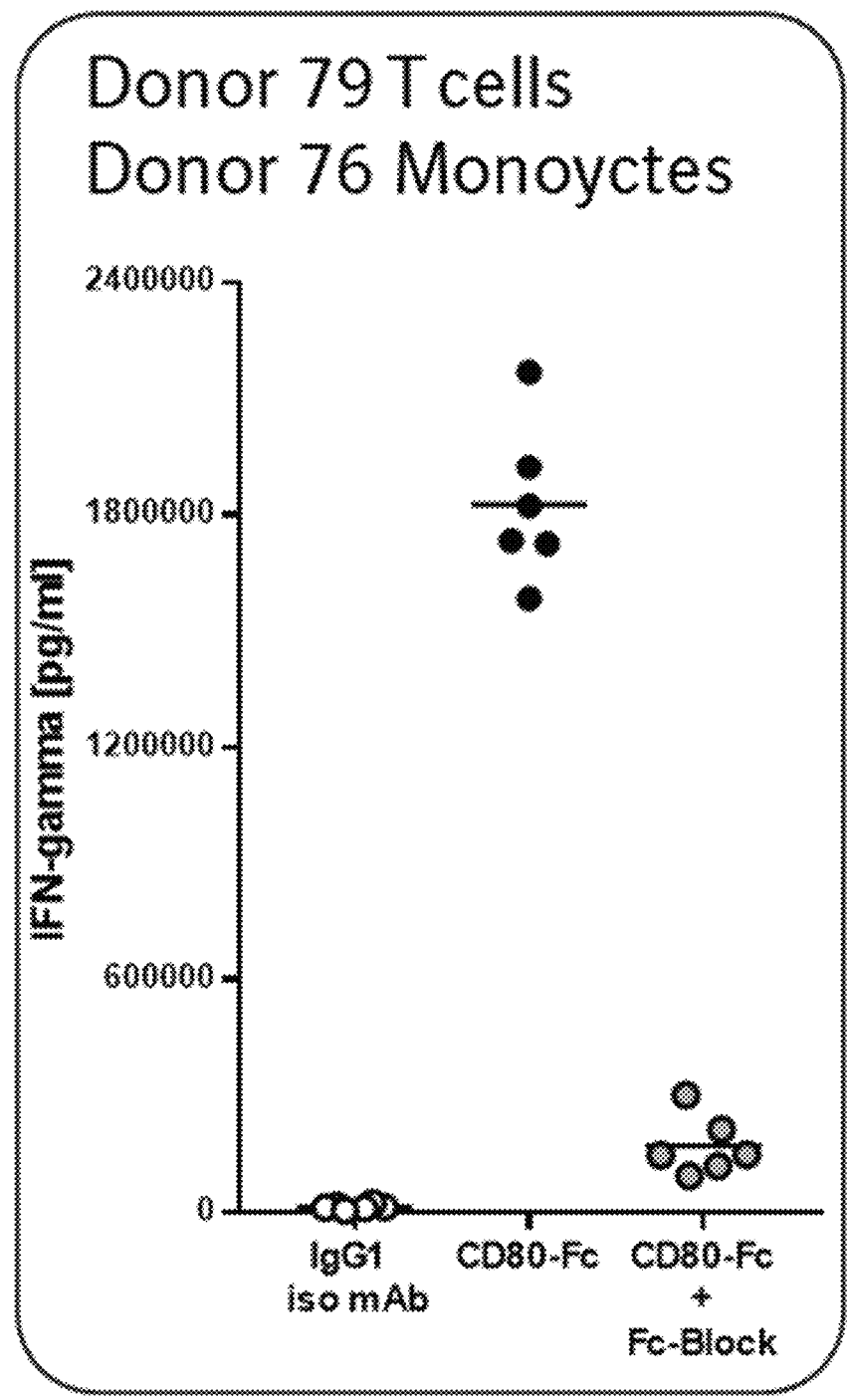

FIG. 13A-D cont.
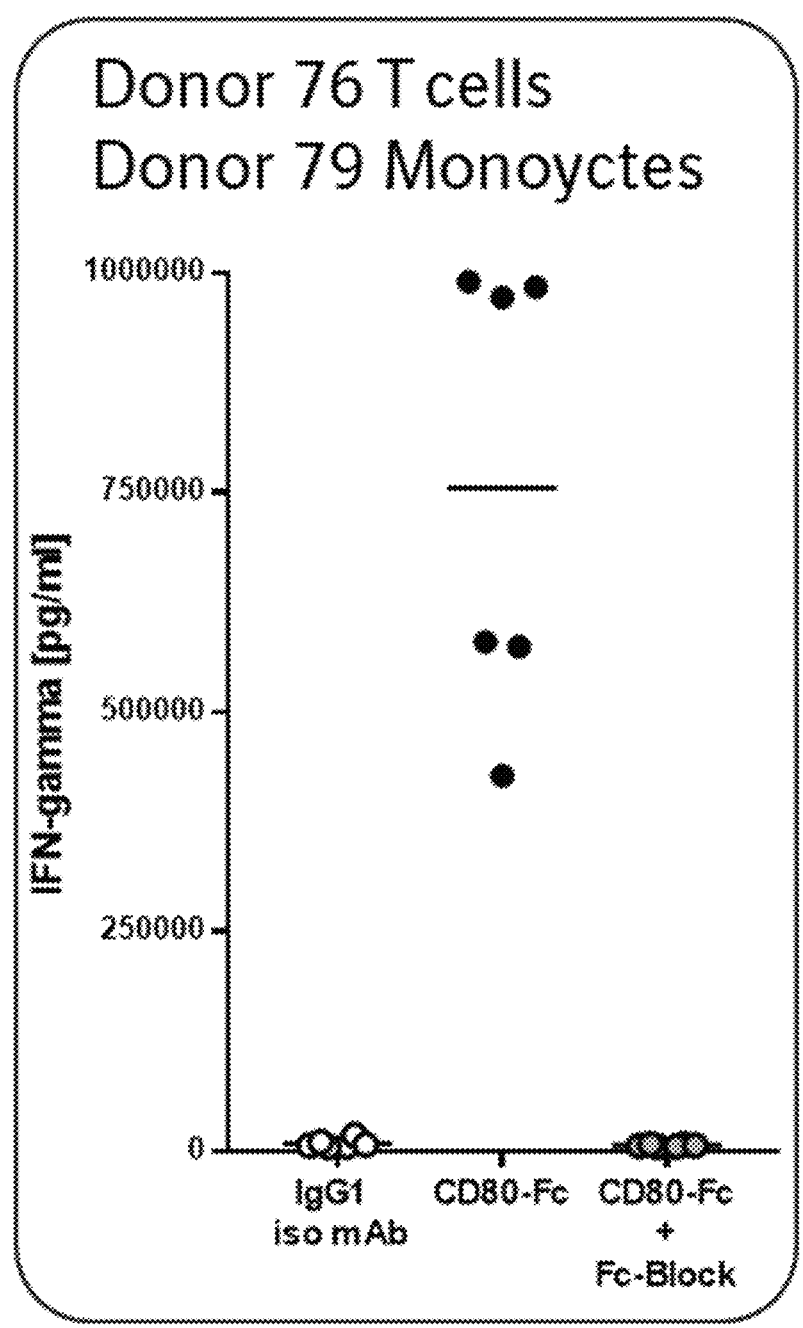

FIG. 13A-D cont.
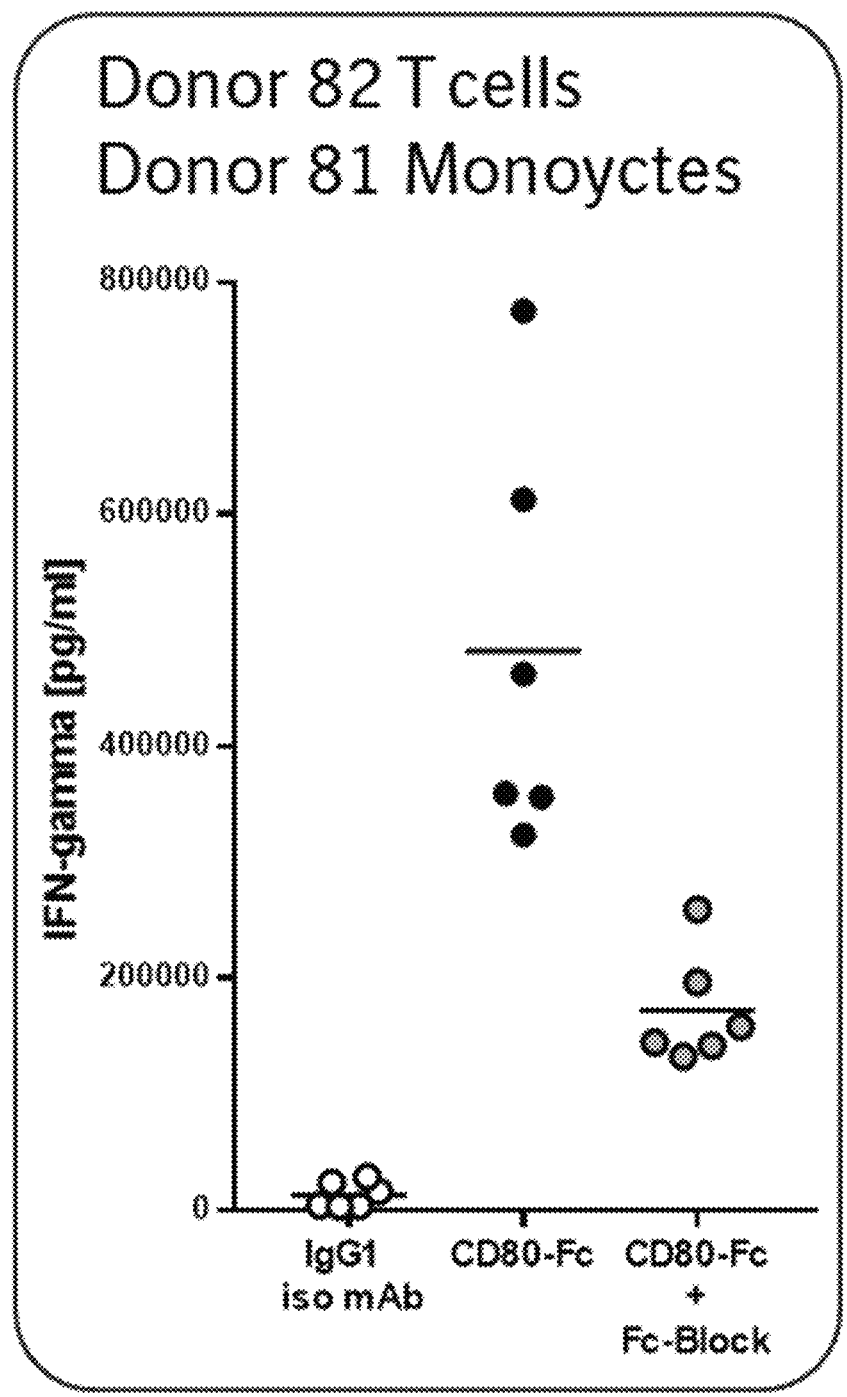

FIG. 13A-D cont.
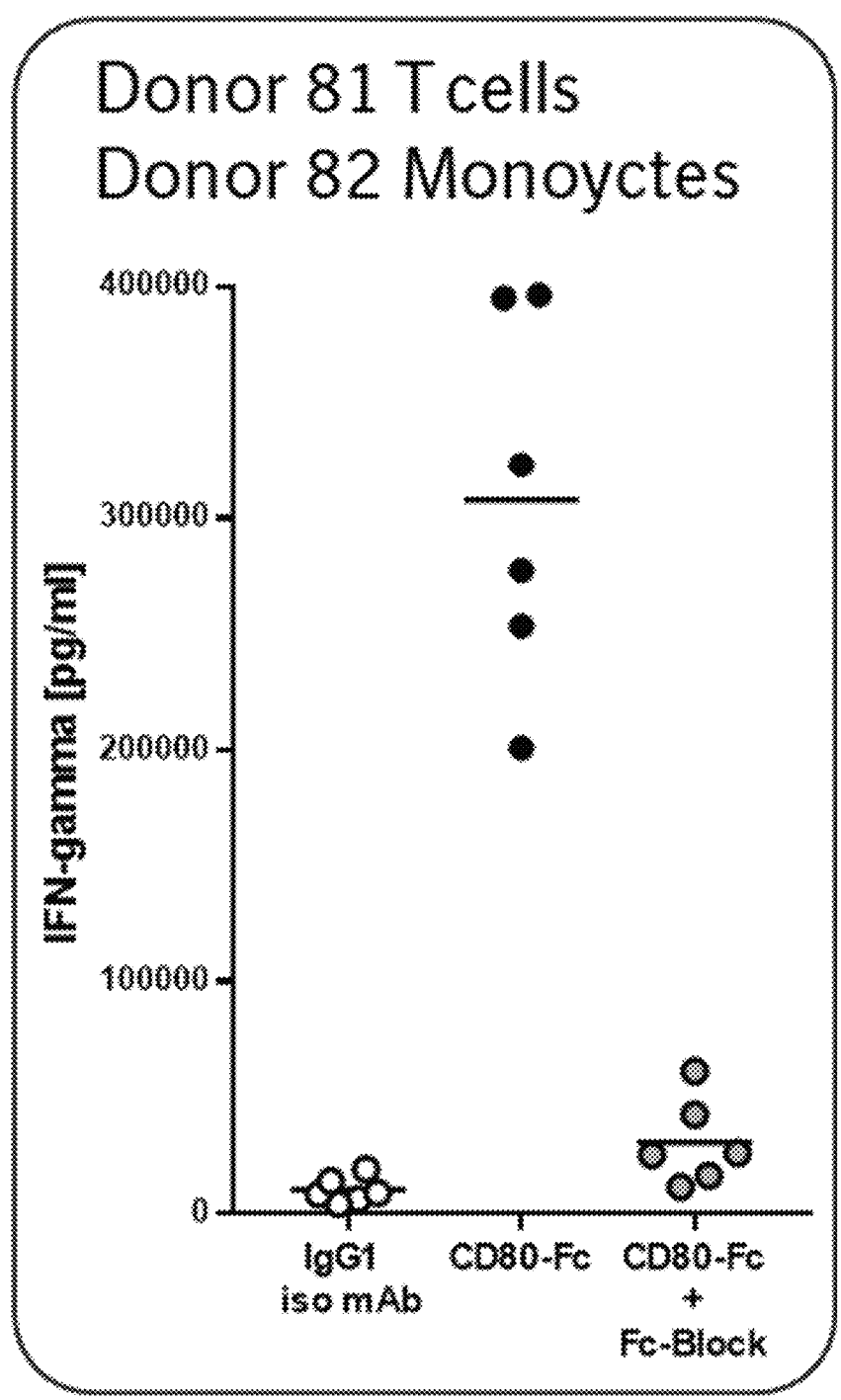

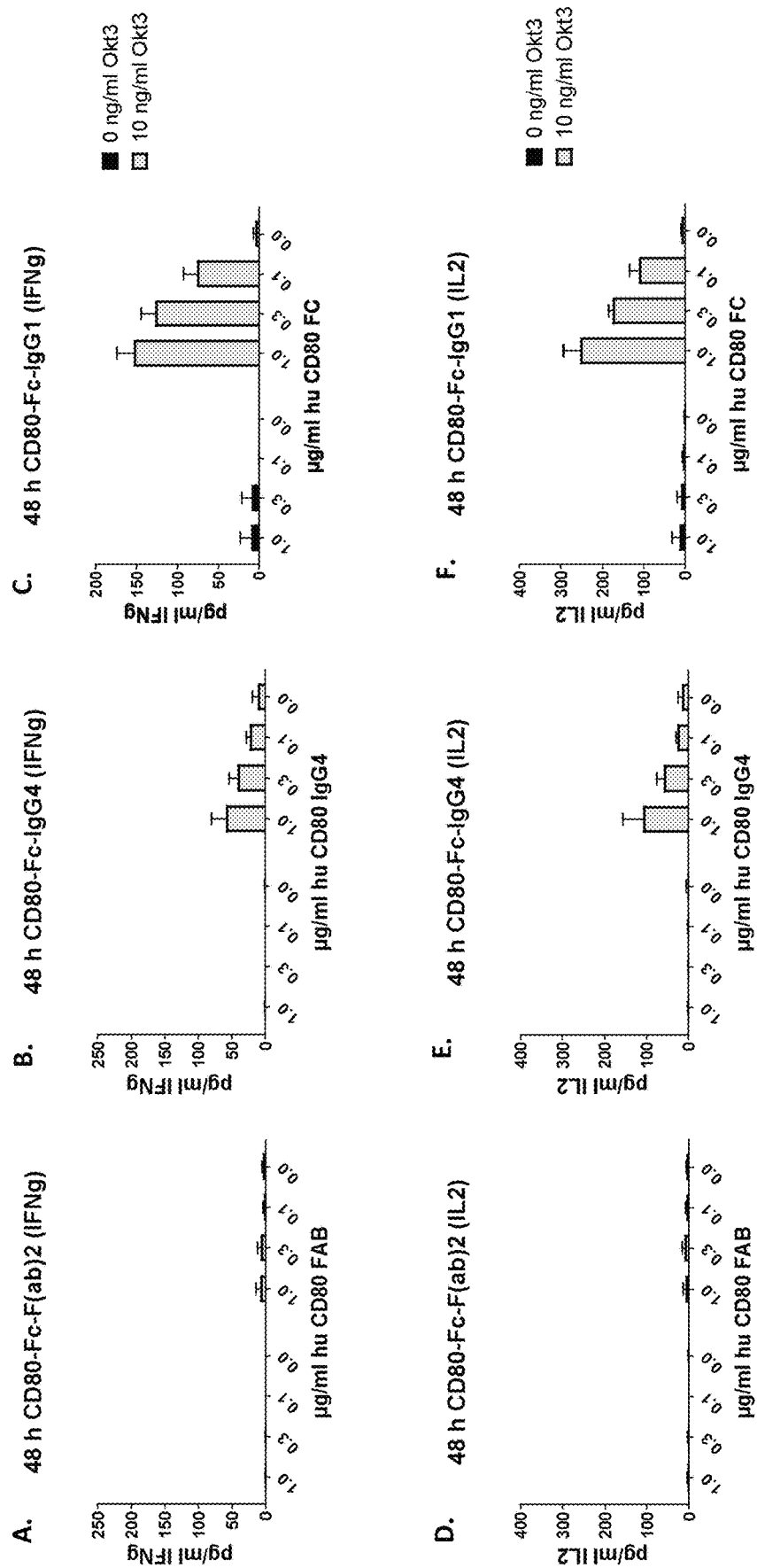
FIG. 14A-F

FIG.16A-C
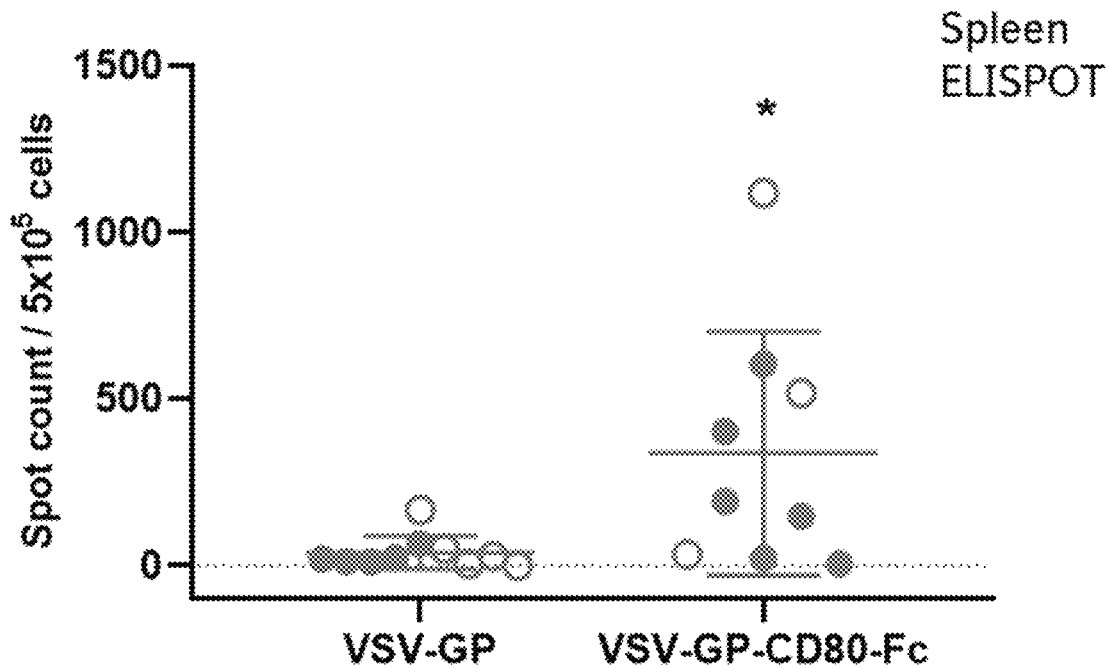
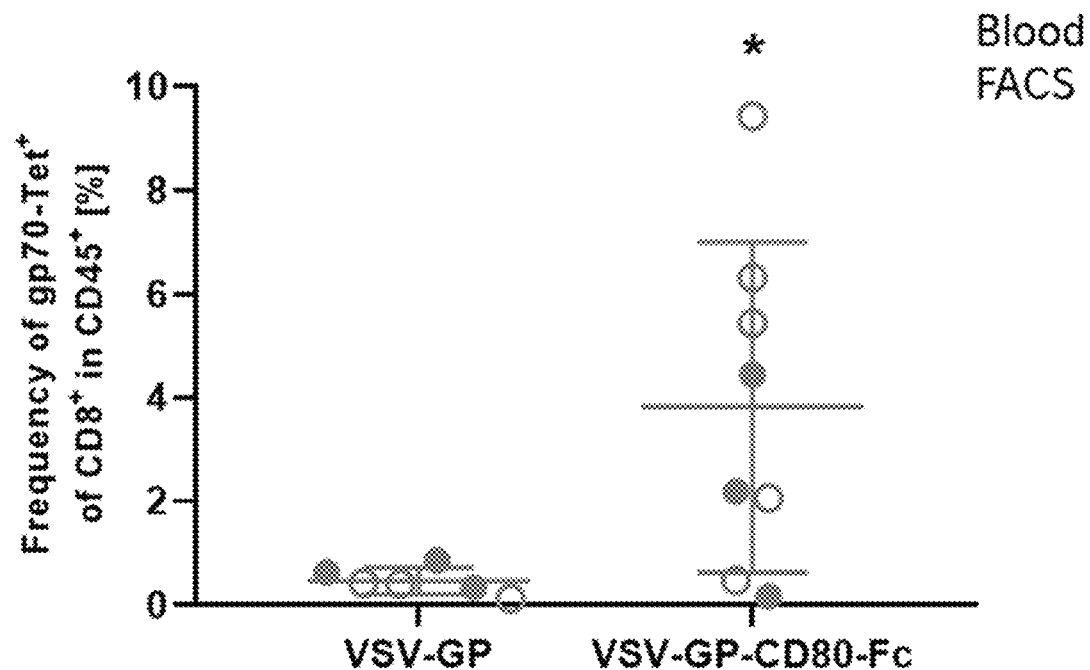

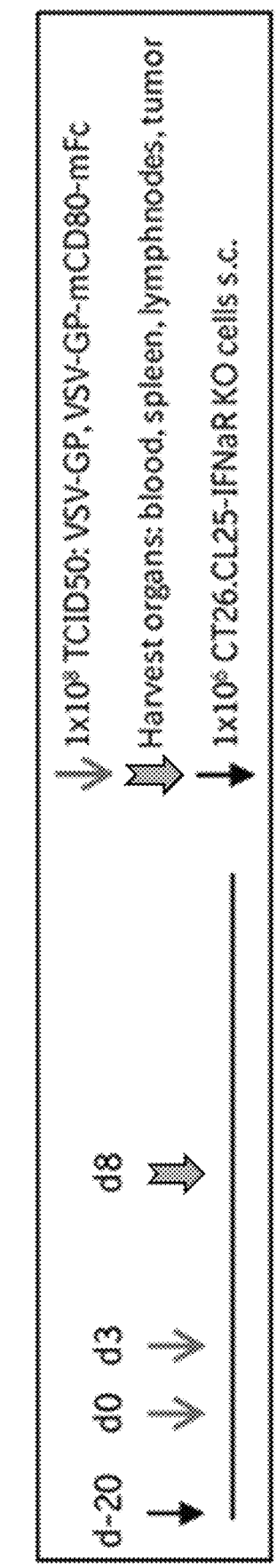
FIG. 16A-C cont.

FIG.18A-B
A
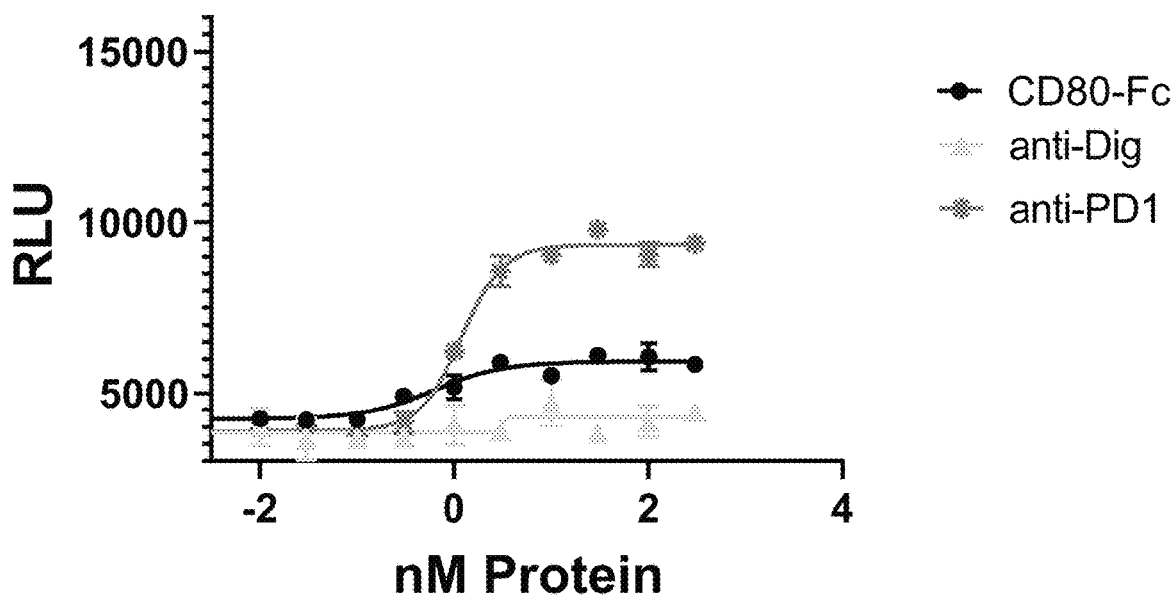
B
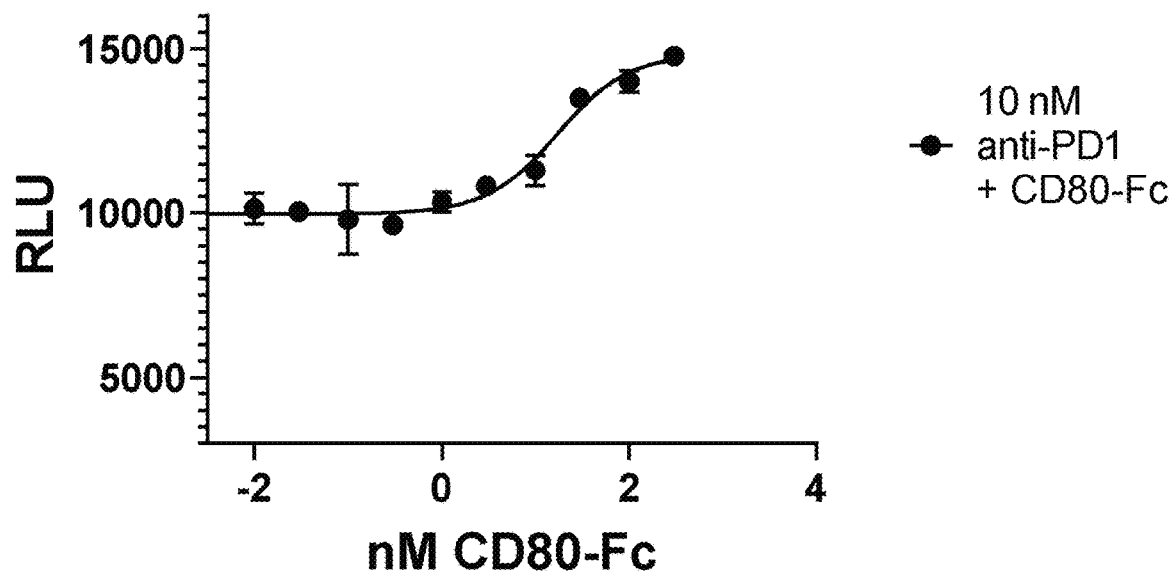

FIG.19A-C
A
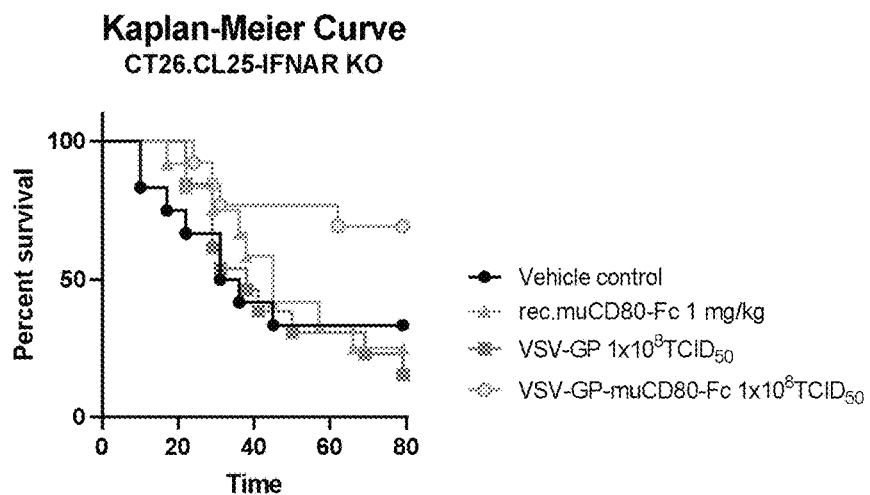
B
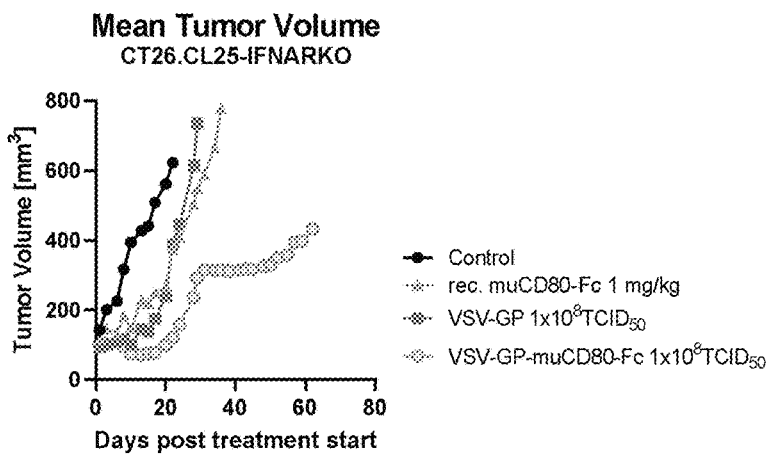
C
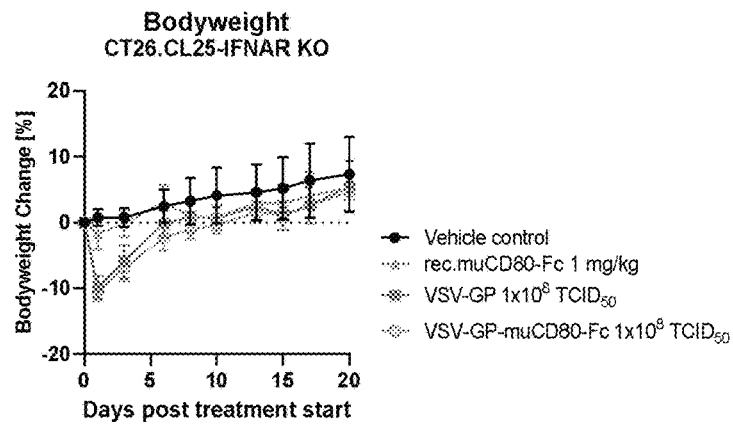

RECOMBINANT RHABDOVIRUS ENCODING FOR A CD80 EXTRACELLULAR DOMAIN Fc-FUSION PROTEIN

SEQUENCE LISTING

The instant application contains a Sequence Listing which has been submitted electronically in ASCII format and is hereby incorporated by reference in its entirety. Said ASCII copy, created on May 27, 2021, is named 01-3411-US-1_SL.txt and is 99,535 bytes in size.

FIELD OF THE INVENTION

The present invention relates to the field of oncolytic viruses and in particular to a recombinant rhabdovirus encoding in its genome for a CD80 extracellular domain Fc-fusion protein. The invention is further directed to the use of the recombinant rhabdovirus in the treatment of cancer, and to methods for producing such viruses.

BACKGROUND OF THE INVENTION

Oncolytic viruses are an emerging class of biologicals, which selectively replicate in and kill cancer cells and are able to spread within tumors. Efforts to further improve oncolytic viruses to increase their therapeutic potential has led to the development of so called armed viruses, which encode in their genome tumor antigens or immune modulatory transgenes to improve their efficacy in tumor treatment.

In many cases there is a paucity of T cells in tumors and therefor there exists what has become known as "immune deserts"—a tumor microenvironment where the immune system's T cells cannot or do not penetrate the tumor to kill the cells growing out of control. It has been postulated that to evade immune surveillance, tumors create an immunosuppressive microenvironment by recruiting myeloid-derived suppressor cells or secrete factors including TGFβ, which play a dual role of inducing the expression of extracellular matrix genes and suppressing the expression of chemokines and cytokines required to facilitate T-cell infiltration into tumors (Pickup M, Novitskiy S, Moses H L. The roles of TGFbeta in the tumour microenvironment. Nat Rev Cancer 2013; 13:788-99). Furthermore, studies have found that tumors exhibiting high expression of genes which correspond to an immunosuppressive microenvironment are associated with poor outcomes across a number of cancer types, including ovarian cancer and colorectal cancer (Calon A, Lonardo E, Berenguer-Llergo A, Espinet E, Hernando-Momblona X, Iglesias M, et al. Stromal gene expression defines poor-prognosis subtypes in colorectal cancer. Nat Genet 2015; 47:320-9; Ryner L, Guan Y, Firestein R, Xiao Y, Choi Y, Rabe C, et al. Upregulation of periostin and reactive stroma is associated with primary chemoresistance and predicts clinical outcomes in epithelial ovarian cancer. Clin Cancer Res 2015; 21:2941-51; Tothill R W, Tinker A V, George J, Brown R, Fox S B, Lade S, et al. Novel molecular subtypes of serous and endometrioid ovarian cancer have been linked to clinical outcome. Clin Cancer Res 2008; 14:5198-208). The hallmarks of the adaptive immune response are specificity and memory. The cellular response is mediated by T-cells, which express cell surface T-cell receptors (TCRs) that recognize peptide antigens in complex with major histocompatibility complex (MHC) molecules on antigen presenting cells (APCs). However, interaction of cognate TCRs with MHC-peptide complexes alone (signal 1) does not trigger optimal T-cell activation. In addition to signal 1, the binding of positive and negative costimulatory receptors to their cognate ligands modulates T-cell activation. This complex signaling network on the one hand provides optimal T-cell activation, while on the other hand aberrant activation of T-cells under physiological conditions is prevented. CD28 (signal 2) is the main positive co-stimulatory receptor on T-cells. When signal 2 (CD28 interaction with B7.1 (CD80) or B7.2 (CD86)) is lacking, for instance on TAA-presenting tumor cells, chronic interactions with TAA-specific T-cells render the latter non-responsive (anergic): the T-cell becomes refractory to signals even when the TCR interacts with TAAs. This situation has been described in cancer patients, especially in chronic situations of advanced disease. Strong T-cell co-stimulation may however reactivate TAA-specific T-cells in late-stage metastasized cancer patients.

One recent approach foresees an oncolytic virus that encodes in its genome the IFN-β protein as a cargo. In a further approach expression of the tumor antigen MAGE-A3 is being explored in the clinic. In addition to identifying a suitable and effective cargo, the expression of additional cargos from a viral backbone, always carries the risk that it will not only potentiate anti-tumor efficacy but also anti-viral immunity. Care has to be taken that the cargo does not restrict the oncolytic potential of the virus to a degree where the benefit gained by expression of the therapeutic cargo is negated by the loss of oncolytic potency. Thus, there is a need in the art for further improved armed oncolytic viruses that can be used in effective cancer treatments. There is further a need in the art to selectively improve T-cell and/or dendritic cell infiltration into immunosuppressive tumor microenvironments.

SUMMARY OF THE INVENTION

The present invention addresses the above needs by providing a recombinant rhabdovirus, such as a vesicular stomatitis virus, which encodes in its genome a CD80 extracellular domain Fc-fusion protein or a functional variant thereof, preferably a human CD80 extracellular domain.

It is to be understood that any embodiment relating to a specific aspect might also be combined with another embodiment also relating to that specific aspect, even in multiple tiers and combinations comprising several embodiments to that specific aspect.

In a first aspect, the present invention relates to a recombinant rhabdovirus encoding in its genome at least one CD80 extracellular domain Fc-fusion protein or a functional variant thereof, wherein the CD80 extracellular domain Fc-fusion protein comprises the extracellular domain of CD80 and further comprises the Fc domain of an IgG.

In one embodiment relating to the first aspect, the CD80 extracellular domain Fc-fusion protein or functional variant thereof is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, (vii) a CD80 extracellular domain Fc-fusion protein, comprising SEQ ID NO:3 or having at least 80% identity to SEQ ID NO:3.

In one embodiment relating to the first aspect, the recombinant rhabdovirus is a *vesiculovirus*.

In one embodiment relating to the first aspect, the *vesiculovirus* is selected from the group comprising: vesicular stomatitis alagoas virus (VSAV), carajás virus (CJSV), chandipura virus (CHPV), cocal virus (COCV), vesicular stomatitis Indiana virus (VSIV), isfahan virus (ISFV), maraba virus (MARAV), vesicular stomatitis New Jersey virus (VSNJV), or piry virus (PIRYV), preferably a vesicular stomatitis Indiana virus (VSIV) or preferably a vesicular stomatitis New Jersey virus (VSNJV).

In one embodiment relating to the first aspect, the recombinant rhabdovirus is replication-competent.

In one embodiment relating to the first aspect, the CD80 extracellular domain is human CD80 extracellular domain.

In one embodiment relating to the first aspect, the recombinant rhabdovirus lacks a functional gene coding for glycoprotein G, and/or lacks a functional glycoprotein G; or, the gene coding for the glycoprotein G is replaced by the gene coding for the glycoprotein GP of another virus, and/or the glycoprotein G is replaced by the glycoprotein GP of another virus; or, the gene coding for the glycoprotein G is replaced by the gene coding for the glycoprotein GP of an arenavirus, and/or the glycoprotein G is replaced by the glycoprotein GP of an arenavirus. In a further preferred embodiment, the gene coding for the glycoprotein G is replaced by the gene coding for the glycoprotein GP of Dandenong virus or Mopeia virus, and/or the glycoprotein G is replaced by the glycoprotein GP of Dandenong virus or Mopeia virus. Even more preferred, the gene coding for the glycoprotein G is replaced by the gene coding for the glycoprotein GP of lymphocyte choriomeningitis virus (LCMV), and/or the glycoprotein G is replaced by the glycoprotein GP of LCMV.

In a preferred embodiment relating to the first aspect, the invention provides a recombinant vesicular stomatitis virus encoding in its genome at least one CD80 extracellular domain Fc-fusion protein or a functional variant thereof, wherein the CD80 extracellular domain Fc-fusion protein comprises the extracellular domain of CD80 and further comprises the Fc domain of an IgG. In a related embodiment, the CD80 extracellular domain Fc-fusion protein is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3; and wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

In a second aspect, the present invention relates to a recombinant vesicular stomatitis virus, encoding in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the CD80 extracellular domain Fc-fusion protein comprises the extracellular domain of CD80 and further comprises the Fc domain of an IgG.

In one embodiment relating to the second aspect, the nucleoprotein (N) comprises an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7.

In one embodiment relating to the second aspect, the phosphoprotein (P) comprises an amino acid sequence as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8.

In one embodiment relating to the second aspect, the large protein (L) comprises an amino acid sequence as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9.

In one embodiment relating to the second aspect, the matrix protein (M) comprises an amino acid sequence as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a preferred embodiment relating to the second aspect, the nucleoprotein (N) comprises an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid sequence as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid sequence as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid sequence as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In one embodiment relating to the second aspect, the recombinant vesicular stomatitis virus is replication-competent.

In one embodiment relating to the second aspect, the recombinant vesicular stomatitis virus lacks a functional gene coding for glycoprotein G, and/or lacks a functional glycoprotein G; or, the gene coding for the glycoprotein G is replaced by the gene coding for the glycoprotein GP of another virus, and/or the glycoprotein G is replaced by the glycoprotein GP of another virus; or, the gene coding for the glycoprotein G is replaced by the gene coding for the glycoprotein GP of lymphocyte choriomeningitis virus (LCMV), and/or the glycoprotein G is replaced by the glycoprotein GP of LCMV.

In one embodiment relating to the second aspect, the CD80 extracellular domain Fc-fusion protein is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3.

In a preferred embodiment relating to the second aspect, the invention provides a recombinant vesicular stomatitis virus encoding in its genome a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the CD80 extracellular domain Fc-fusion protein comprises the extracellular domain of CD80 and further comprises the Fc domain of an IgG and is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3; and wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a third aspect, the present invention provides for a pharmaceutical composition, characterized in that the composition comprises a recombinant rhabdovirus according to the first aspect or any of its embodiments, or a recombinant vesicular stomatitis virus according the second aspect or any of its embodiments.

In a fourth aspect, the present invention provides for a recombinant rhabdovirus according to the first aspect or any of its embodiments, or a recombinant vesicular stomatitis virus according the second aspect or any of its embodiments, or a pharmaceutical composition according to the third aspect or any of its embodiments, for use as a medicament.

In one embodiment relating to the fourth aspect, the invention provides a recombinant rhabdovirus, a recombinant vesicular stomatitis virus, or a pharmaceutical composition for the use in the treatment of cancer, preferably solid cancers. In a preferred embodiment, the solid cancer is selected from the list comprising: reproductive tumor, an ovarian tumor, a pancreatic tumor, a testicular tumor, an endocrine tumor, a gastrointestinal tumor, a liver tumor, a kidney tumor, a colon tumor, a colorectal tumor, a bladder tumor, a prostate tumor, a skin tumor, melanoma, a respiratory tumor, a lung tumor, a breast tumor, a head & neck tumor, a head and neck squamous-cell carcinoma (HNSCC), and a bone tumor.

In one embodiment relating to the fourth aspect, the recombinant rhabdovirus, the recombinant vesicular stomatitis virus, or the pharmaceutical composition is to be administered intratumorally or intravenously. In another related embodiment, the recombinant rhabdovirus, the recombinant vesicular stomatitis virus or the pharmaceutical composition is to be administered at least once intratumorally and subsequently intravenously. In a further related embodiment, the subsequent intravenous administration of the recombinant rhabdovirus, recombinant vesicular stomatitis virus or the pharmaceutical composition is given 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

In a fifth aspect, the present invention provides for a composition comprising a recombinant rhabdovirus according to the first aspect or any of its embodiments, or a recombinant vesicular stomatitis virus according the second aspect or any of its embodiments and further an inhibitor, wherein the inhibitor is a PD-1 pathway inhibitor or a SMAC mimetic.

In one embodiment relating to the fifth aspect, the PD-1 pathway inhibitor is an antagonistic antibody, which is directed against PD-1 or PD-L1. In a further related embodiment, the SMAC mimetic is selected from the group consisting of any of compounds 1 to 26 from table 2 or a pharmaceutically acceptable salt of one of these compounds. In another related embodiment, the PD-1 pathway inhibitor is an antagonist selected from the group consisting of pembrolizumab, nivolumab, pidilizumab, atezolizumab, avelumab, durvalumab, PDR-001, PD1-1, PD1-2, PD1-3, PD1-4 and PD1-5 (as shown in Table 1). In a most preferred embodiment, the PD-1 pathway inhibitor is BI-754091.

In a sixth aspect, the present invention provides a kit of parts comprising: a recombinant rhabdovirus, a recombinant vesicular stomatitis virus or a pharmaceutical composition as defined in any of the first to third aspects or any of their embodiments, and a PD-1 pathway inhibitor or SMAC mimetic as defined in any of the embodiments relating to the fifth aspect.

In a seventh aspect, the present invention provides for a combination treatment comprising: a) a recombinant rhabdovirus according to the first aspect or any of its embodiments, or a recombinant vesicular stomatitis virus according the second aspect or any of its embodiments, or a pharmaceutical composition according to the third aspect or any of its embodiments, and b) a PD-1 pathway inhibitor or a SMAC mimetic. In one embodiment relating to the seventh aspect a) and b) may be administered concomitantly, sequentially or alternately. In a related embodiment, a) and b) are administered via different administration routes. In a further related embodiment, a) is administered intratumorally b) is administered intravenously.

In one embodiment relating to the seventh aspect, the PD-1 pathway inhibitor is an antagonistic antibody, which is directed against PD-1 or PD-L1. In a related embodiment the PD-1 pathway inhibitor is selected from the group consisting of pembrolizumab, nivolumab, pidilizumab, atezolizumab, avelumab, durvalumab, PDR-001, PD1-1, PD1-2, PD1-3, PD1-4 and PD1-5 (see Table 1). In a further related embodiment the SMAC mimetic is selected from the group consisting of any one of compounds 1 to 26 according to table 2 or a pharmaceutically acceptable salt of one of these compounds.

In an eight aspect, the invention provides for a virus producing cell, characterized in that the cell produces a recombinant rhabdovirus according to the first aspect or any of its embodiments, or a recombinant vesicular stomatitis virus according the second aspect or any of its embodiments.

In one embodiment relating to the eight aspect, the virus producing cell is a Vero cell, a HEK cell, a HEK293 cell, a Chinese hamster ovary cell (CHO), or a baby hamster kidney (BHK) cell.

In a ninth aspect, the invention provides for a method of producing a recombinant rhabdovirus in a cell culture:
(i) Infecting a host cell with a recombinant rhabdovirus, preferably a vesicular stomatitis virus,
(ii) Culturing the host cell under conditions allowing replication of the recombinant rhabdovirus,
(iii) Harvesting the recombinant rhabdovirus from the cell culture,
(iv) Optionally, enzyme treatment of the virus harvest, preferably with benzonase,
(v) Capturing the rhabdovirus harvest by loading on a cation exchange monolith membrane adsorber or resin followed by elution,
(vi) Polish rhabdovirus by subjecting the eluate of step (v) to size exclusion, multi modal size exclusion/ion exchange or tangential flow filtration,
(vii) Buffer change of polished rhabdovirus by ultrafiltration/diafiltration,
(viii) Sterile filtration of rhabdovirus.

In one embodiment relating to the ninth aspect, the host cell is a HEK293 cell.

In one embodiment relating to the ninth aspect, the host cell is cultured in suspension.

In one embodiment relating to the ninth aspect, the recombinant rhabdovirus is formulated into a pharmaceutical composition. In a preferred embodiment, the recombinant rhabdovirus according to the first aspect or any of its embodiments, or a recombinant vesicular stomatitis virus according the second aspect or any of its embodiments is formulated into a pharmaceutical composition.

BRIEF DESCRIPTION OF THE DRAWINGS

FIG. 5A-B In vivo efficacy (A) and body weight development (B) of mice treated with VSV-GP-CD80-Fc compared to the parental virus VSV-GP using the CT26.CL25-IFNARKO tumor model (i.v.). (A) Mice were treated on day 0 & 3 with a low viral dose of $2 \times 10^7$ $TCID_{50}$. X-axis shows the time (in days) and y-axis the percentage of mice that survived. (B) Body weight development of the same treated mice as in FIG. 6A is shown. X-axis shows the time (in days) and y-axis the body weight (in g)

FIG. 6A-C In vivo efficacy of VSV-GP-CD80-Fc compared to the parental virus VSV-GP in treated mice using the B16-F1-OVA tumor model (i.t.) with treatments on day 0 & 3 with a viral dose of $10^8$ $TCID_{50}$ VSV-GP (B), the same viral dose of VSV-GP-CD80-Fc (C) or PBS (A). X-axis shows the days post treatment (in days) and y-axis the tumor volume (in $cm^3$).

FIG. 7A-B In vivo efficacy of VSV-GP-CD80-Fc in treated mice (B) compared to the parental virus VSV-GP (A) using the EMT-6 tumor model (i.t.) and treatments on day 0 & 3 with a low viral dose of $2 \times 10^7$ $TCID_{50}$. X-axis shows the days post treatment (in days) and y-axis the tumor volume (in $cm^3$). Dotted line represents mice treated with vehicle and solid line mice treated with virus.

FIG. 9 NanoString-based measurement of VSV-GP N-protein as well as CD80-Fc transcripts in control, VSV-GP or VSV-GP-CD80-Fc infected LLC-IFNARKO tumors taken from treated mice. Mice were either used as control or treated with $10^8$ $TCID_{50}$ VSV-GP or VSV-GP-CD80-Fc and the relative expression of the viral N-protein or CD80-Fc (y-axis) were determined after 3 days.

FIG. 13A-D Human Mixed-Leukocyte culture (T-cells and monocytes from two genetically different individuals are co-cultured), stimulated with recombinant CD80-Fc protein (10 µg/ml) and with or without the addition of FcγR-block (and in the absence of human serum), using IFNs secretion as readout. The different sub-figures (A-D) depict different donor pairs.

FIG. 14A-F Human PBMC cultures were stimulated with or without low doses of anti-CD3 and increasing concentrations of recombinant CD80-Fc protein (F(ab)2 (A, D), Fc=IgG4 (B, E) or Fc=IgG1 (C, F)), measuring IFNγ (A-C) or IL2 (D-F) secretion as readouts, which were detected by standard ELISA of the supernatants.

FIG. 16A-C Improved induction of tumor-specific T-cells by VSV-GP-mCD80-Fc vs. VSV-GP was determined in CT26.CL25-IFNARKO tumor bearing mice using ELIS-POT and tetramer staining. gp70-specific α-Tumor-T-cells are increased in the Spleen of VSV-GP-mCD80-Fc vs. VSV-GP treated mice. Open symbols represent i.v. treatments. Closed symbols represent i.v./i.t. treatments. (A) Detection of gp70-specific T-cells from spleens by ELIS-POT or (B) from blood by Dextramers. (C) Experimental outline.

FIG. 18A-B Reporter Cell Assay: Jurkat-PD1 (luciferase reporter cells) in co-culture with THP-1-PDL1 cells (express FcγRs). T-cell activation is triggered by a CD33XCD3 BiTE (10 nM) in this system. (A) Treatment with the indicated reagents (anti-PD1=Pembrolizumab; anti-Dig=isotype control & recombinant CD80-Fc) at the indicated concentrations. (B) Anti-PD1 (10 nM) and increasing concentrations of recombinant CD80-Fc improve Jurkat T-cell activation beyond the activity of the individual compounds.

FIG. 19A-C In vivo efficacy (A), tumor growth curves (B) and body weight change (C) of mice treated with VSV-GP-muCD80-Fc, the parental virus VSV-GP, and recombinant murine CD80-Fc using the CT26.CL25-IFNARKO tumor model (i.v.). (A) Mice were treated on day 0 & 3 with a viral dose of $1 \times 10^8$ $TCID_{50}$ and on day 0, 3 and 6 with 1 mg/kg recombinant murine CD80-Fc, respectively. The x-axis shows the time (in days) and the y-axis the percentage of mice that survived. (B) Mean tumor volumes over time of the same treated mice as in FIG. 19A is shown. The x-axis shows the time (in days after start of treatment) and the y-axis the tumor volume (in $mm^3$). Data show the group mean with last observation carried forward until 70% of group size was reached (70% LOCF). (C) Body weight change of the same treated mice as in FIG. 19A is shown. The x-axis shows the time (in days after start of treatment) and the y-axis the body weight change compared to initial body weight at treatment start (in %).

DETAILED DESCRIPTION OF THE INVENTION

Figure 1:
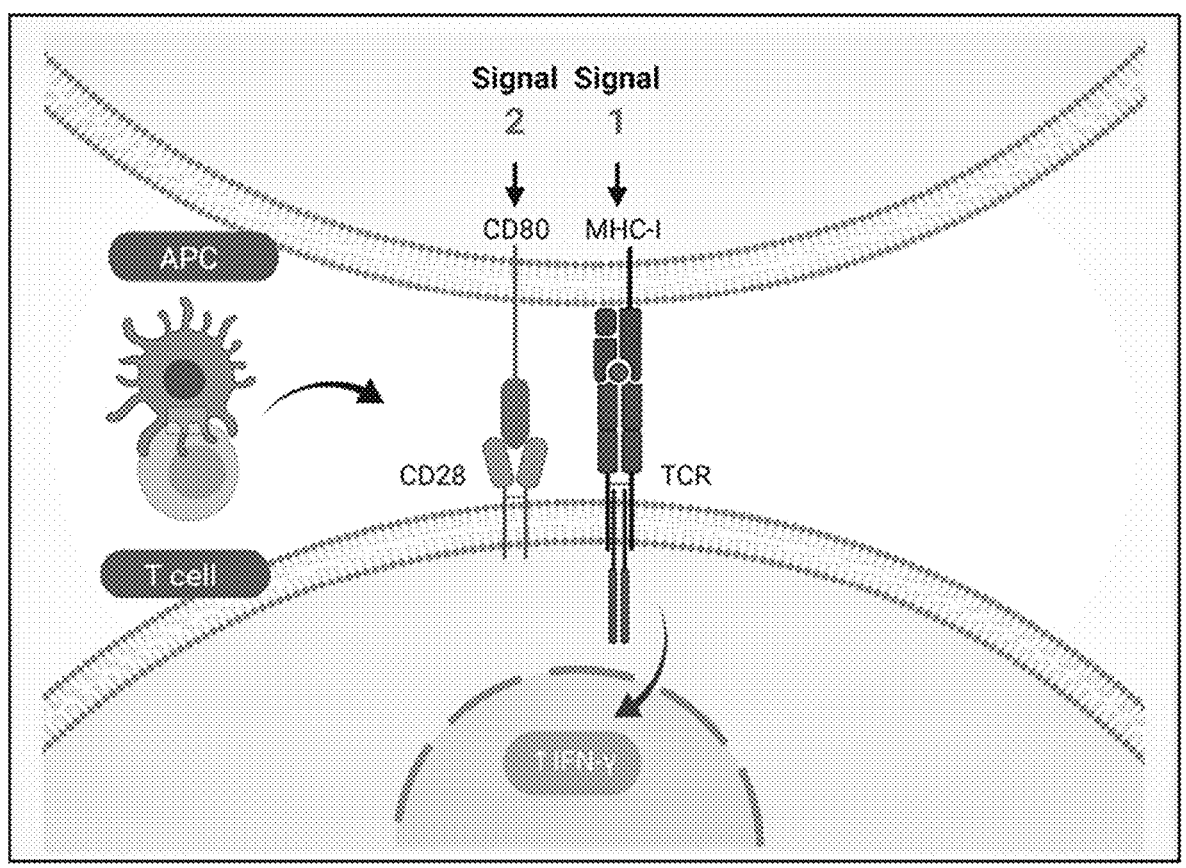
FIG. 1: A schematic representation of an immunological synapse and components between an Antigen Presenting Cell (APC) and a T-cell. CD80 is a key co-stimulatory molecule during T-cell activation. Efficient T-cell stimulation requires two converging molecular signals within the immunological synapse. Signal 1: Antigen-specific (TCR: MHC/Peptide) and Signal 2. Antigen-independent (CD28: CD80).
Figure 2:
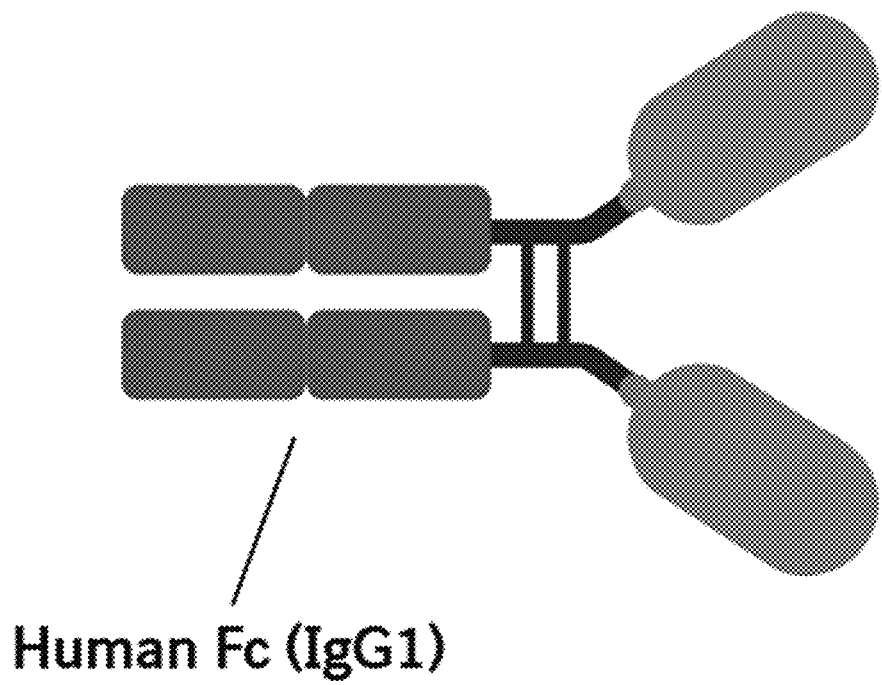
FIG. 2: Cartoon of CD80 extracellular domain (ECD) Fc-fusion protein (bivalent). The fusion protein is expressed in the transduced tumor cells following viral infection. The two CD80 extracellular domain Fc-fusion monomers are covalently linked together by disulfide bonds formed between cysteine residues in each monomer, thereby forming the CD80 extracellular domain Fc-fusion protein dimer.

In the following detailed description, numerous specific details are set forth to provide a full understanding of the present invention. It will be apparent, however, to one ordinarily skilled in the art that the subject technology may be practiced without some of these specific details. In other instances, well-known structures and techniques have not been shown in detail so as not to obscure the present invention. The headings are included merely for convenience to assist in reading and shall not be understood to limit the invention to specific aspects or embodiments.

Rhabdoviruses

The family of rhabdoviruses includes 18 genera and 134 species with negative-sense, single-stranded RNA genomes of approximately 10-16 kb (Walke et al., ICTV Virus Taxonomy Profile: Rhabdoviridae, Journal of General Virology, 99:447-448 (2018)).

Characterizing features of members of the family of rhabdoviruses include one or more of the following: A bullet-shaped or bacilliform particle 100-430 nm in length and 45-100 nm in diameter comprised of a helical nucleocapsid surrounded by a matrix layer and a lipid envelope, wherein some rhabdoviruses have non-enveloped filamentous viruses. A negative-sense, single-stranded RNA of 10.8-16.1 kb, which are mostly unsegmented. A genome encoding for at least 5 genes encoding the structural proteins nucleoprotein (N), large protein (L), phosphoprotein (P), matrix protein (M), and glycoprotein (G).

As used herein a rhabdovirus can belong to the genus of: *almendravirus, curiovirus, cytorhabdovirus, dichorhavirus, ephemerovirus, Hapavirus, ledantevirus, lyssavirus, novirhabdovirus, nucleorhabdovirus, perhabdovirus, sigmavirus, sprivivirus, sripuvirus, tibrovirus, tupavirus, varicosavirus* or *vesiculovirus*.

Within the genus mentioned herein the rhabdovirus can belong to any of the listed species. The genus of *almendravirus* includes: *Arboretum almendravirus, Balsa almendravirus*, Coot Bay *almendravirus*, Puerto Almendras *almendravirus*, Rio Chico *almendravirus*; the genus of *curiovirus* includes: *Curionopolis curiovirus, Iriri curiovirus, Ltacaiunas curiovirus, Rochambeau curiovirus*; the genus of *cythorhabdovirus* includes: *Alfalfa dwarf cytorhabdovirus*, Barley yellow striate mosaic *cytorhabdovirus*, Broccoli necrotic yellows *cytorhabdovirus, Colocasia bobone* disease-associated *cytorhabdovirus*, Festuca leaf streak *cytorhabdovirus*, Lettuce necrotic yellows *cytorhabdovirus*, Lettuce yellow mottle *cytorhabdovirus*, Northern cereal mosaic *cytorhabdovirus, Sonchus cytorhabdovirus* 1, Strawberry crinkle *cytorhabdovirus*, Wheat American striate mosaic *cytorhabdovirus*; the genus of *dichorhavirus* includes: Coffee ringspot *dichorhavirus*, Orchid fleck *dichorhavirus*; the genus of *ephemerovirus* includes: Adelaide River *ephemerovirus, Berrimah ephemerovirus*, Bovine fever *ephemerovirus, Kimberley ephemerovirus, Koolpinyah ephemerovirus, Kotonkan ephemerovirus, Obodhiang ephemerovirus, Yata ephemerovirus*; the genus of *hapavirus* includes: *Flanders hapavirus*, Gray Lodge *hapavirus*, Hart Park *hapavirus, Joinjakaka hapavirus, Kamese hapavirus, La Joya hapavirus, Landjia hapavirus, Manitoba hapavirus, Marco hapavirus, Mosqueiro hapavirus, Mossuril hapavirus, Ngaingan hapavirus, Ord River hapavirus, Parry Creek hapavirus, Wongabel hapavirus*; the genus of *ledantevirus* includes: *Barur ledantevirus, Fikirini ledantevirus, Fukuoka ledantevirus, Kanyawara ledantevirus, Kern Canyon ledantevirus, Keuraliba ledantevirus, Kolente ledantevirus, Kumasi ledantevirus, Le Dantec ledantevirus, Mount Elgon bat ledantevirus, Nishimuro ledantevirus, Nkolbisson ledantevirus, Oita ledantevirus, Wuhan ledantevirus, Yongjia ledantevirus*; the genus of *lyssavirus* includes: *Aravan lyssavirus*, Australian bat *lyssavirus*, Bokeloh bat *lyssavirus, Duvenhage lyssavirus*, European bat 1 *lyssavirus*, European bat 2 *lyssavirus*, Gannoruwa bat *lyssavirus, Ikoma lyssavirus, Irkut lyssavirus, Khujand lyssavirus*, Lagos bat *lyssavirus*, Lleida bat *lyssavirus*, Mokola *lyssavirus*, Rabies *lyssavirus*, Shimoni bat *lyssavirus*, West Caucasian bat *lyssavirus*; the genus of *novirhabdovirus* includes: *Hirame novirhabdovirus, Piscine novirhabdovirus, Salmonid novirhabdovirus, Snakehead novirhabdovirus*; the genus of *nucleorhabdovirus* includes: Datura yellow vein *nucleorhabdovirus*, Eggplant mottled dwarf *nucleorhabdovirus*, Maize fine streak *nucleorhabdovirus*, Maize Iranian mosaic *nucleorhabdovirus*, Maize mosaic *nucleorhabdovirus*, Potato yellow dwarf *nucleorhabdovirus*, Rice yellow stunt *nucleorhabdovirus, Sonchus* yellow net *nucleorhabdovirus*, Sowthistle yellow vein *nucleorhabdovirus*, Taro vein chlorosis *nucleorhabdovirus*; the genus of *perhabdovirus* includes: *Anguillid perhabdovirus, Perch perhabdovirus, Sea trout perhabdovirus*; the genus of *sigmavirus* includes: *Drosophila affinis sigmavirus, Drosophila ananassae sigmavirus, Drosophila immigrans sigmavirus, Drosophila melanogaster sigmavirus, Drosophila obscura sigmavirus, Drosophila tristis sigmavirus, Muscina stabulans sigmavirus*; the genus of *sprivivirus* includes: *Carp sprivivirus, Pike fry sprivivirus*; the genus of *Sripuvirus* includes: *Almpiwar sripuvirus, Chaco sripuvirus, Niakha sripuvirus, Sena Madureira sripuvirus, Sripur sripuvirus*; the genus of *tibrovirus* includes: *Bas-Congo tibrovirus, Beatrice Hill tibrovirus, Coastal Plains tibrovirus, Ekpoma* 1 *tibrovirus*, Ekpoma 2 *tibrovirus, Sweetwater Branch tibrovirus, Tibrogargan tibrovirus*; the genus of *tupavirus* includes: *Durham tupavirus, Klamath tupavirus, Tupaia tupavirus*; the genus of *varicosavirus* includes: Lettuce big-vein associated *varicosavirus*; the genus of *vesiculovirus* includes: *Alagoas vesiculovirus*, American bat *vesiculovirus, Carajas vesiculovirus, Chandipura vesiculovirus, Cocal vesiculovirus, Indiana vesiculovirus, Isfahan vesiculovirus, Jurona vesiculovirus, Malpais Spring vesiculovirus, Maraba vesiculovirus, Morreton vesiculovirus, New Jersey vesiculovirus, Perinet vesiculovirus, Piry vesiculovirus, Radi vesiculovirus, Yug Bogdanovac vesiculovirus*, or *Moussa virus*.

Preferably, the recombinant rhabdovirus of the invention is anoncolytic rhabdovirus. In this respect, oncolytic has its regular meaning known in the art and refers to the ability of a rhabdovirus to infect and lyse (break down) cancer cells but not normal cells (to any significant extend). Preferably, the oncolytic rhabdovirus is capable of replication within cancer cells. Oncolytic activity may be tested in different assay systems known to the skilled artisan (an exemplary in vitro assay is described by Muik et al., Cancer Res., 74(13), 3567-78, 2014). It is to be understood that an oncolytic rhabdovirus may infect and lyse only specific types of cancer cells. Also, the oncolytic effect may vary depending on the type of cancer cells.

In a preferred embodiment, the rhabdovirus belongs to the genus of *vesiculovirus*. *Vesiculovirus* species have been defined primarily by serological means coupled with phylogenetic analysis of the genomes. Biological characteristics such as host range and mechanisms of transmission are also used to distinguish viral species within the genus. As such, the genus of *vesiculovirus* form a distinct monophyletic group well-supported by Maximum Likelihood trees inferred from complete L sequences.

Viruses assigned to different species within the genus *vesiculovirus* may have one or more of the following characteristics: A) a minimum amino acid sequence divergence of 20% in L; B) a minimum amino acid sequence divergence of 10% in N; C) a minimum amino acid sequence divergence of 15% in G; D) can be distinguished in serological tests; and E) occupy different ecological niches as evidenced by differences in hosts and or arthropod vectors.

Preferred is the vesicular stomatitis virus (VSV) and in particular the VSV-GP (recombinant with GP of LCMV). Advantageous properties of the VSV-GP include one or more of the following: very potent and fast killer (<8 h); oncolytic virus; systemic application possible; reduced neurotropism/neurotoxicity; it reproduces lytically and induces immunogenic cell death; does not replicate in healthy human cells, due to interferon (IFN) response; strong activation of innate immunity; about 3 kb space for immunomodulatory cargos and antigens; recombinant with an arenavirus glycoprotein from the Lympho-Chorio-Meningitis-Virus (LCMV); favorable safety features in terms of reduced neurotoxicity and less sensitive to neutralizing antibody responses and complement destruction as compared to the wild type VSV (VSV-G); specifically replicates in tumor cells, which have lost the ability to mount and respond to anti-viral innate immune responses (e.g. type-I IFN signaling); abortive replication in "healthy cells" so is rapidly excluded from normal tissues; viral replication in tumor cells leads to the induction of immunogenic cell death, release of tumor associated antigens, local inflammation and the induction of anti-tumor immunity.

The invention is further embodied by a recombinant vesicular stomatitis virus, encoding in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, preferably comprising the human CD80 extracellular domain.

In a preferred embodiment the recombinant vesicular stomatitis virus encodes in its genome at least for a vesicular stomatitis virus nucleoprotein (N) comprising an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, a phosphoprotein (P) comprising an amino acid sequence as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, a large protein (L) comprising an amino acid sequence as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and a matrix protein (M) comprising an amino acid sequence as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

It is understood by the skilled artisan that modifications to the vesicular stomatitis virus nucleoprotein (N), large protein (L), phosphoprotein (P), matrix protein (M), or glycoprotein (G) sequence can be made without losing the basic functions of those proteins. Such functional variants as used herein retain all or part of their basic function or activity. The protein L for example is the polymerase and has an essential function during transcription and replication of the virus. A functional variant thereof must retain at least part of this ability. A good indication for retention of basic functionality or activity is the successful production of viruses, including these functional variants, that are still capable to replicate and infect tumor cells. Production of viruses and testing for infection and replication in tumor cells may be tested in different assay systems known to the skilled artisan (an exemplary in vitro assay is described by Muik et al., Cancer Res., 74(13), 3567-78, 2014).

In a preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the large protein (L) comprises an amino acid sequence having a sequence identity ≥80% of SEQ ID NO:9.

In a preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the nucleoprotein (N) comprises an amino acid sequence having a sequence identity ≥90% of SEQ ID NO:7.

In a further preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the large protein (L) comprises an amino acid sequence having a sequence identity equal or greater 80% of SEQ ID NO:9 and the nucleoprotein (N) comprises an amino acid sequence having a sequence identity ≥90% of SEQ ID NO:7.

In a preferred embodiment of the invention the RNA genome of the recombinant rhabdovirus of the invention comprises or consists of a sequence as shown in SEQ ID NO: 24. Furthermore, the RNA genome of the recombinant rhabdovirus of the invention may also consist of or comprise those sequences, wherein nucleic acids of the RNA genome are exchanged according to the degeneration of the genetic code, without leading to an alteration of respective amino acid sequence. In a further preferred embodiment, the RNA genome of the recombinant rhabdovirus of the invention comprises or consists of a coding sequence identical or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24.

It is to be understood that a recombinant rhabdovirus of the invention may encode in its genome further cargos, such as tumor antigens, further chemokines, cytokines or other immunomodulatory elements.

In a further embodiment the recombinant rhabdovirus of the invention additionally encodes in its genome a sodium iodide symporter protein (NIS). Expression of NIS and co-incubation with e.g. $^{125}$I allows the use of NIS as imaging reporter (Carlson et al., Current Gene Therapy, 12, 33-47, 2012).

Recombinant Rhabdovirus

It is known that certain wildtype rhabdovirus strains such as wildtype VSV strains are considered to be neurotoxic. It is also reported that infected individuals are able to rapidly mount a strong humoral response with high antibody titers directed mainly against the glycoprotein. Neutralizing antibodies targeting the glycoprotein G of rhabdoviruses in general and VSV specifically are able to limit virus spread and thereby mediate protection of individuals from virus re-infection. Virus neutralization, however, limits repeated application of the rhabdovirus to the cancer patient.

To eliminate these drawbacks the rhabdovirus wildtype glycoprotein G may be replaced with the glycoprotein from another virus. In this respect replacing the glycoprotein refers to (i) replacement of the gene coding for the wild type glycoprotein G with the gene coding for the glycoprotein GP of another virus, and/or (ii) replacement of the wild type glycoprotein G with the glycoprotein GP of another virus.

In a preferred embodiment the rhabdovirus glycoprotein G is replaced with the glycoprotein GP of the lymphocytic choriomeningitis virus (LCMV), preferably with the strain WE-HPI. In an even more preferred embodiment, the rhabdovirus is a vesicular stomatitis virus with the glycoprotein GP of the lymphocytic choriomeningitis virus (LCMV), preferably with the strain WE-HPI. Such VSV is for example described in WO2010/040526 and named VSV-GP. Advantages offered are (i) the loss of VSV-G mediated neurotoxicity and (ii) a lack of vector neutralization by antibodies (as shown in mice).

The glycoprotein GP of the lymphocytic choriomeningitis virus (LCMV) may be GP1 or GP2. The invention includes glycoproteins from different LCMV strains. In particular, LCMV-GP can be derived from LCMV wild-type or LCMV strains LCMV-WE, LCMV-WE-HPI, LCMV-WE-HPI opt. In a preferred embodiment, the gene coding for the glycoprotein GP of the LCMV encodes for a protein with an amino acid sequence as shown in SEQ ID NO:11 or an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:11 while the functional properties of the recombinant rhabdovirus comprising a glycoprotein GP encoding an amino acid sequence as shown in SEQ ID NO:11 are maintained.

In another embodiment the recombinant rhabdovirus glycoprotein G is replaced with the glycoprotein GP of the Dandenong virus (DANDV) or Mopeia (MOPV) virus. In a more preferred embodiment, the recombinant rhabdovirus is a vesicular stomatitis virus wherein the glycoprotein G is replaced with the glycoprotein GP of the Dandenong virus (DANDV) or Mopeia (MOPV) virus. Advantages offered are (i) the loss of VSV-G mediated neurotoxicity and (ii) a lack of vector neutralization by antibodies (as shown in mice).

The Dandenong virus (DANDV) is an old world arenavirus. To date, there is only a single strain known to the person skilled in the art, which comprise a glycoprotein GP and which may be employed within the present invention as donor of the glycoprotein GP comprised in the recombinant rhabdovirus of the invention. The DANDV glycoprotein GP comprised in the recombinant rhabdovirus of the invention has more than 6 glycosylation sites, in particular 7 glycosylation sites. An exemplary preferred glycoprotein GP is that as comprised in DANDV as accessible under Genbank number EU136038. In one embodiment, the gene coding for the glycoprotein GP of the DNADV encodes for an amino acid sequence as shown in SEQ ID NO:12 or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:12 while the functional properties of the recombinant rhabdovirus comprising a glycoprotein GP encoding an amino acid sequence as shown in SEQ ID NO:12 are maintained.

The Mopeia virus (MOPV) is an old world arenavirus. There are several strains known to the person skilled in the art, which comprise a glycoprotein GP and which may be employed within the present invention as donor of the glycoprotein GP comprised in the recombinant rhabdovirus of the invention. The MOPV glycoprotein GP comprised in the recombinant rhabdovirus of the invention has more than 6 glycosylation sites, in particular 7 glycosylation sites. An exemplary preferred glycoprotein GP is that as comprised in Mopeia virus as accessible under Genbank number AY772170. In one embodiment, the gene coding for glycoprotein GP of the MOPV encodes for an amino acid sequence as shown in SEQ ID NO:13 or a sequence having at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:13 while the functional properties of the recombinant rhabdovirus comprising a glycoprotein GP encoding an amino acid sequence as shown in SEQ ID NO:13 are maintained.

CD80 Extracellular Domain Fc-Fusion Protein

CD80, also known as B7-1, is a 60 kD single chain type I glycoprotein belonging to the immunoglobulin superfamily. CD80 is expressed on activated/mature antigen-presenting cells, such as dendritic cells. CD80 binds to CD28 and CD152 (CTLA-4). Along with CD86 (B7-2), CD80 plays a critical role in the regulation of T-cell activation. The interaction of CD80 with CD28 provides a co-stimulatory signal for T-cell activation in the complex of TCR engagement. Its interaction with CTLA-4 (e.g. expressed on regulatory T-cells), which has a higher affinity for CD80 than CD28 and acts as a decoy receptor for CD80, rather than functioning as a suppressive signaling receptor, deprives T-cells of the crucial co-stimulatory CD28 signal.

In the past it was proposed that oncolytic viruses and in particular VSV-GP can induce tumor cell lysis combined with immunogenic cell death and stimulation of innate immune cells in the tumor microenvironment. It was further proposed that immune modulatory proteins may be encoded into the genome of oncolytic viruses and that the expression of said immune modulatory proteins may support the oncolytic effect of the virus by local immune stimulating activities.

One of the challenges of expressing immune-promoting molecules from a viral backbone, such as chemokines and/or cytokines, is that not only potentiation of anti-tumor immunity must be achieved but at the same time an anti-viral immunity response by the immune-promoting molecule is to be avoided. Care has to be taken that the additional immune-promoting molecule does not restrict the oncolytic potential of the virus to a degree where the potential benefit gained by expression of the therapeutic cargo is overruled by the loss of oncolytic potency.

The inventors hypothesized that a CD80 extracellular domain Fc-fusion protein on the one side may provide efficient T-cell co-stimulation in the context of T-cell receptor engagement and on the other side would not activate natural killer cells (activated by e.g. IL2, IL15, CD137), which would limit viral replication and/or persistence at an early stage. The CD80 extracellular domain Fc-fusion protein is a potent co-stimulatory molecule, active in priming and re-activation of antigen-specific T-cells. This stimulus is crucial as T-cell co-stimulatory signals are often underrepresented in tumors, leading to clonal T-cell anergy, loss of effector function and T-cell death.

By providing a recombinant rhabdovirus according to the invention tumor-restricted replication of a CD80 extracellular domain Fc-fusion protein may lead to the local expression of the T-cell co-stimulating fusion protein, which further enhances anti-tumor T-cell immunity by providing activating signals to T-cells in the context of T-cell receptor engagement (e.g. tumor cell recognition) in an FcγR-dependent manner.

The inventors surprisingly found that a recombinant rhabdovirus according to the invention encoding for a CD80 extracellular domain Fc-fusion protein was able to induce tumor cell lysis combined with immunogenic cell death and stimulation of innate immune cells in the tumor microenvironment. Further, prolonged survival rates were observed in an established mouse tumor model treated with such a recombinant rhabdovirus armed with a CD80 extracellular domain Fc-fusion protein.

Unexpectedly, infection with the recombinant rhabdovirus according to the invention encoding for a CD80 extracellular domain Fc-fusion protein lead to a strong increase of FcγR expression within the infected tumors. It was shown by the inventors that optimal biological activity of the CD80 extracellular domain Fc-fusion protein is strongly dependent on the FcγR.

Without wishing to be bound by theory, it is believed that the strong anti-tumoral effects obtained by the recombinant rhabdovirus according to the invention encoding for a CD80 extracellular domain Fc-fusion protein is based at least in part on the FcγR-dependent activity of the CD80 extracellular domain Fc-fusion protein, which activity is potentiated by the increased expression of FcγRs in infected tumors after infection with recombinant rhabdovirus according to the invention.

Alternatively, in this context provision of a CD86 (B7-2) fusion protein is also contemplated, i.e. a recombinant rhabdovirus encoding for a CD86 extracellular domain Fc-fusion protein and in particular a VSV-GP encoding for a CD86 extracellular domain Fc-fusion protein, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

A "CD80 extracellular domain Fc-fusion protein" as used herein refers to a fusion protein or a functional variant thereof comprising or consisting of a CD80 extracellular domain which is fused to the Fc domain of an IgG.

The "CD80 extracellular domain" comprises or consists of naturally occurring polypeptides, such as different isoforms, as well as functional variants thereof, preferably the human CD80 extracellular domain.

In one aspect, the recombinant rhabdovirus encoding in its genome at least one CD80 extracellular domain Fc-fusion protein or a functional variant thereof is able to enhance recruitment of T-cells and dendritic cells to the tumor environment.

In another aspect, expression of the at least one CD80 extracellular domain Fc-fusion protein or a functional variant thereof from the genome of the recombinant rhabdovirus provides a therapeutic option for patients with cold tumors and a low mutational burden to boost the T-cell mediated anti-tumor T-cell response against poorly immunogenic tumors.

In another aspect, expression of the at least one CD80 extracellular domain Fc-fusion protein or a functional variant thereof from the genome of the recombinant rhabdovirus does not induce additional natural killer cells (beyond the effects of the parental VSV-GP virus) and selectively activates antigen-specific T-cells.

In another aspect, expression of the at least one CD80 extracellular domain Fc-fusion protein or a functional variant thereof from the genome of the recombinant rhabdovirus does not induce superagonism.

In another aspect, expression of the at least one CD80 extracellular domain Fc-fusion protein or a functional variant thereof from the genome of the recombinant rhabdovirus does not increase early anti-viral immunity to the recombinant rhabdovirus.

In yet another aspect, in addition to local expression in the tumor due to its solubility the CD80 extracellular domain Fc-fusion protein may also reach tumor-draining lymphatics (e.g. lymph nodes).

Human CD80 protein (UniProtKB—P33681|CD80_HUMAN T-lymphocyte activation antigen CD80) comprises or consists of 288 amino acids total and contains a signal peptide, an extracellular domain and a transmembrane/topological domain:

```
                                            (SEQ ID NO: 6)
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTKQEHFPDNLLPSWAIT

LISVNGIFVICCLTYCFAPRCRERRRNERLRRESVRPV.
```

In one embodiment, the CD80 extracellular domain of the CD80 extracellular domain Fc-fusion protein comprises or consists of amino acids 1-242 of SEQ ID NO:6 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 1-242 of SEQ ID NO:6.

In another embodiment the CD80 extracellular domain of the CD80 extracellular domain Fc-fusion protein comprises or consists of the following sequence:

```
                                            (SEQ ID NO: 1)
VIHVTKEVKEVATLSCGHNVSVEELAQTRIYWQKEKKMVLTMMSGDMNIW

PEYKNRTIFDITNNLSIVILALRPSDEGTYECVVLKYEKDAFKREHLAEV

TLSVKADFPTPSISDFEIPTSNIRRIICSTSGGFPEPHLSWLENGEELNA

INTTVSQDPETELYAVSSKLDFNMTTNHSFMCLIKYGHLRVNQTFNWNTT

KQEHFPDN
``` or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1.

In one embodiment, the CD80 extracellular domain Fc-fusion protein comprises a signal peptide sequence. In another embodiment, the CD80 extracellular domain Fc-fusion does not comprise a signal peptide sequence.

The term "signal peptide" or "signal peptide sequence" describes a peptide sequence usually 10 to 30 amino acids in length and present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed. In particular, the signal peptide may be capable of directing the polypeptide into a cell's secretory pathway.

It is to be understood that for the present invention other (i.e., other than the wild-type) signal peptide sequences may be used together with the CD80 extracellular domain Fc-fusion protein. Such other signal peptide sequences may replace the original wild-type signal peptide sequence. A signal peptide includes peptides that direct newly synthesized protein in the ribosome to the ER and further to the Golgi complex for transport to the plasma membrane or out of the cell. They generally include a string of hydrophobic amino acids and include immunoglobulin leader sequences as well as others known to those skilled in the art. Signal peptides include in particular peptides capable of being acted upon by signal peptidase, a specific protease located on the cisternal face of the endoplasmic reticulum. Signal peptides are well understood by those of skill in the art and may include any known signal peptide. The signal peptide is incorporated at the N-terminus of the protein and processing of the CD80 extracellular domain Fc-fusion protein by signal peptidase produces the active biological form.

In one embodiment, the CD80 extracellular domain Fc-fusion protein comprises the wild-type CD80 signal peptide sequence. In a preferred embodiment, the CD80 extracellular domain Fc-fusion protein comprises the wild-type human CD80 signal peptide sequence which is amino acids 1-34 of SEQ ID NO:6 or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 1-34 of SEQ ID NO:6.

In another embodiment, the CD80 extracellular domain Fc-fusion protein comprises a signal peptide sequence having the following sequence:

MGWSCIILFLVATATGVHS (SEQ ID NO:5)

or a signal peptide sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5.

In a related embodiment the CD80 extracellular domain of the CD80 extracellular domain Fc-fusion protein comprises or consists of SEQ ID NO:1 or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1 and further comprises a signal peptide sequence according to SEQ ID NO:5 or a signal peptide sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5

A CD80 extracellular domain Fc-fusion protein may also include a fusion protein with a truncated signal peptide sequence. In this context truncated refers to a signal peptide sequence that is shorter than the original signal peptide sequence but still retains at least a portion of its functionality to act as a signal peptide. For example, the human CD80 signal peptide sequence comprises or consists of amino acids 1-34 of SEQ ID NO:6. A CD80 extracellular domain Fc-fusion protein with a truncated signal peptide sequence could have 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 of the amino acids 1-34 of SEQ ID NO:6. In a further example, the signal peptide could comprise or consist of the sequence as shown in SEQ ID NO:5. A CD80 extracellular domain Fc-fusion protein with a truncated signal peptide sequence could have 18, 17, 16, 15, 14, 13, 12, 11, 10, 9, 8, 7, 6, 5, 4, 3, 2 or 1 of the amino acids 1-18 of SEQ ID NO:5.

A CD80 extracellular domain Fc-fusion protein with a truncated signal peptide sequence could also be a protein comprising SEQ ID No: 1 or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1 and in addition a signal peptide sequence that is shorter than the original signal peptide sequence. Again, by way of example signal peptide sequence could have 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 of the amino acids 1-34 of SEQ ID NO:6 or in a further example, the signal peptide could comprise or consist of the sequence as shown in SEQ ID NO:5. A CD80 extracellular domain Fc-fusion protein with a truncated signal peptide sequence could have 18, 17, 16, 15, 14, 13, 12, 11, 10, 9, 8, 7, 6, 5, 4, 3, 2 or 1 of the amino acids 1-18 of SEQ ID NO:5.

The CD80 extracellular domain can be of any origin including from mouse and rat. Preferably, the CD80 extracellular domain protein is from human origin.

The Fc domain of an IgG may be fused covalently to the N- or C-terminal part of the CD80 extracellular domain or at an internal position. In some embodiments, the Fc domain of an IgG molecule may be fused to the CD80 extracellular domain through a linker peptide, such as a GS linker. Preferably, the Fc domain is fused to the C-terminal part of the CD80 extracellular domain.

In some embodiments, the Fc domain has a wild-type sequence. In other embodiments, the Fc domain is either a natural or engineered variant. In some embodiments, the Fc domain comprises one or more mutations, substitutions and/or deletions compared to its wild-type sequence. In some embodiments, an Fc domain is chosen that has altered interactions of the Fc with one or more Fc gamma receptors (FcγRI, FcγRIIA, FcγRIIB, FcγRIIIA, FcγRIIIB). Preferably, the Fc domain is derived from a human IgG such as IgG1, IgG2, IgG3 or IgG4. More preferably, the Fc domain is derived of a human IgG1.

In an preferred embodiment the Fc domain of the CD80 extracellular domain Fc-fusion protein comprises or consists of the following sequence:

(SEQ ID NO: 2)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:2.

In a preferred embodiment the CD80 extracellular domain Fc-fusion protein comprises or consists of the following sequence:

(SEQ ID NO: 4)
VIHVTKEVKEVATLSCGHNVSVEELAQTRIYWQKEKKMVLTMMSGDMNIW

PEYKNRTIFDITNNLSIVILALRPSDEGTYECVVLKYEKDAFKREHLAEV

TLSVKADFPTPSISDFEIPTSNIRRIICSTSGGFPEPHLSWLENGEELNA

INTTVSQDPETELYAVSSKLDFNMTTNHSFMCLIKYGHLRVNQTFNWNTT

KQEHFPDDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQV

-continued

SLTCLVKGFYPSDIAVEWESNGQPENNYKTTPPVLDSDGSFFLYSKLTVD

KSRWQQGNVFSCSVMHEALHNHYTQKSLSLSPG or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:4.

In a further preferred embodiment, the CD80 extracellular domain Fc-fusion protein comprises or consists of a CD80 extracellular domain fused to the Fc domain of an IgG1, wherein the CD80 extracellular domain comprises or consists of amino acids 1-207 of SEQ ID NO:4 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 1-207 of SEQ ID NO:4 and the Fc domain comprises or consists of amino acids 208-433 of SEQ ID NO:4 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 208-433 of SEQ ID NO:4

In a further preferred embodiment the CD80 extracellular domain Fc-fusion protein comprises or consists of the following sequence:

(SEQ ID NO: 3)
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTKQEHFPDDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPG or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:3.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Functional variants of a CD80 extracellular domain Fc-fusion protein include biologically active variants and biologically active fragments of the foregoing described CD80 extracellular domain Fc-fusion proteins. The functional variants may either have variations in the CD80 extracellular domain, the Fc-domain and/or in both domains. By way of example, some CD80 extracellular domain functional variants have been described in WO2017181152. In another example, functional variants of the Fc-domain have been described in WO17079117 and comprise e.g. human IgG1 Fc domains with L234F, L235E, and/or P331S amino acid substitutions.

For example, variants may have one or more different amino acids in a position of a specifically described CD80 extracellular domain or Fc-domain protein. Variants can share at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid identity with such a CD80 extracellular domain or Fc domain. Fragments have the same amino acids as a given specifically described CD80 extracellular domain or Fc domain protein but may lack a specific portion or area of the CD80 extracellular domain or Fc domain protein.

Functional variants of the CD80 extracellular domain Fc-fusion protein only include variants and fragments of CD80 extracellular domain Fc-fusion protein that are biologically active. For the invention, the biological activity of the CD80 extracellular domain Fc-fusion protein variant or the CD80 extracellular domain Fc-fusion protein fragment—which is encoded in the genome of a recombinant rhabdovirus—is determined after its expression in a respective cell or tumor cell. This means that the biological activity is determined in the context of a recombinant rhabdovirus encoding for the CD80 extracellular domain Fc-fusion protein variant or the CD80 extracellular domain Fc-fusion protein fragment (e.g. in a Transwell assay or in vitro tumor model). Preferably, the biological activity is determined with a *vesiculovirus* encoding for the CD80 extracellular domain Fc-fusion protein variant or the CD80 extracellular domain Fc-fusion protein fragment. More preferably, the biological activity is determined with a VSV-GP encoding for the CD80 extracellular domain Fc-fusion protein variant or the CD80 extracellular domain Fc-fusion protein fragment.

Biological activity can include one or more of the following abilities: chemoattractant activity, anti-tumor activity, modulation of cytokine expression such as increase in the expression of Interferon-gamma (IFN-gamma) polypeptides or decrease in the expression of transforming growth factor-beta (TGF-beta) polypeptides in a population of syngeneic mammalian cells including CD8 positive T cells, CD4 positive T cells, antigen presenting cells and tumor cells. Testing for biological activity may be done without limitation for example according to the protocol as shown in the Examples. For the purpose of the invention the functional variant or fragment of the CD80 extracellular domain Fc-fusion protein is biologically active if it shows at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% of the activity of a CD80 extracellular domain Fc-fusion protein with the sequence as shown in SEQ ID NO:3 or 4 (respectively with or without signal peptide sequence) if tested in the same assay and under the same conditions.

Rhabdoviruses have negative sense single-stranded RNA (ssRNA) as their genetic material (genome). Negative sense ssRNA viruses need RNA polymerase to form a positive sense RNA. The positive-sense RNA acts as a viral mRNA, which is translated into proteins for the production of new virus materials. With the newly formed virus, more negative sense RNA molecules are produced.

A typical rhabdovirus genome encodes for at least five structural proteins in the order of 3'-N-P-M-G-L-S'. The genome might contain further short intergenic regions or additional genes between the structural proteins and therefore might vary in length and organization.

According to the invention the CD80 extracellular domain Fc-fusion protein gene can be introduced into any location of the rhabdovirus genome. Depending on the insertion site the transcription efficiency of the CD80 extracellular domain Fc-fusion protein gene can be influenced. In general, transcription efficiency of the CD80 extracellular domain Fc-fusion protein gene decreases from 3' insertion to 5' prime insertion. The CD80 extracellular domain Fc-fusion protein gene may be inserted into the following genome locations: 3'-CD80 extracellular domain Fc-fusion protein-N-P-M-G-L-5',3'-N-CD80 extracellular domain Fc-fusion protein-P-M-G-L-5', 3'-N-P-CD80 extracellular domain Fc-fusion protein-M-G-L-5',3'-N-P-M-CD80 extracellular domain Fc-fusion protein-G-L-5',3'-N-P-M-G-CD80 extracellular domain Fc-fusion protein-L-5' or 3'-N-P-M-G-L-CD80 extracellular domain Fc-fusion protein-5'. In a preferred embodiment the CD80 extracellular domain Fc-fusion protein gene is inserted between the G protein and the L protein.

After infection of tumor cells the CD80 extracellular domain Fc-fusion protein gene encoded in the genome of the recombinant rhabdovirus is transcribed into positive sense RNA and then translated into CD80 extracellular domain Fc-fusion protein by the tumor cell. The term "encoding" or "coding" refers to the inherent property of specific sequences of nucleotides in a nucleic acid to serve as templates for synthesis of other polymers and macromolecules in biological processes having a defined sequence of nucleotides (e.g. RNA molecules) or amino acids and the biological properties resulting therefrom. Accordingly, a gene codes for a protein if the desired protein is produced in a cell or another biological system by transcription and subsequent translation of the mRNA. Both the coding strand, the nucleotide sequence of which is identical to the mRNA sequence and the non-coding strand may serve as the template for the transcription of a gene and can be referred to as encoding the protein or other product of that gene. Nucleic acids and nucleotide sequences that encode proteins may include introns.

The transcription of the CD80 extracellular domain Fc-fusion protein gene is preferably not under the control of its own promoter and only strictly linked to viral replication ensuring thereby targeted expression of CD80 extracellular domain Fc-fusion protein to the location of viral replication and spread (tumor). Thus, the transcription of the CD80 extracellular domain Fc-fusion protein gene is not controlled by additional elements such as promoters or inducible gene expression elements.

The translated CD80 extracellular domain Fc-fusion protein typically exists in solution as a dimeric fusion protein comprising two identical monomeric mature CD80 extracellular domain Fc-fusion proteins. In this instance, each monomeric CD80 extracellular domain Fc-fusion protein comprises a CD80 extracellular domain fused at its C-terminus to the N-terminus of an IgG Fc domain. The two CD80 extracellular domain Fc-fusion monomers are covalently linked together by disulfide bonds formed between cysteine residues in each monomer, thereby forming the CD80 extracellular domain Fc-fusion protein dimer.

It will be appreciated that a nucleic acid sequence may be varied with or without changing the primary sequence of the encoded polypeptide. A nucleic acid that encodes a protein includes any nucleic acids that have different nucleotide sequences but encode the same amino acid sequence of the protein due to the degeneracy of the genetic code. It is within the knowledge of the skilled artisan to choose a nucleic acid sequence that will result in the expression of a CD80 extracellular domain Fc-fusion protein and in particular to any specific CD80 extracellular domain Fc-fusion protein proteins as disclosed herein. Nucleic acid molecules encoding amino acid sequences of CD80 extracellular domain Fc-fusion protein are prepared by a variety of methods known in the art. These methods include, but are not limited to, isolation from a natural source or preparation by oligonucleotide-mediated (or site-directed) mutagenesis, PCR mutagenesis, and cassette mutagenesis of an earlier prepared CD80 extracellular domain Fc-fusion protein.

Pharmaceutical Compositions

The actual pharmaceutically effective amount or therapeutic dosage will of course depend on factors known by those skilled in the art such as age and weight of the patient, route of administration and severity of disease. In any case the recombinant rhabdovirus will be administered at dosages and in a manner which allows a pharmaceutically effective amount to be delivered based upon patient's unique condition.

Generally, for the treatment and/or alleviation of the diseases, disorders and conditions mentioned herein and depending on the specific disease, disorder or condition to be treated, the potency of the specific recombinant rhabdovirus of the invention to be used, the specific route of administration and the specific pharmaceutical formulation or composition used, the recombinant rhabdovirus of the invention will generally be administered for example, twice a week, weekly, or in monthly doses, but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

To be used in therapy, the recombinant rhabdovirus of the invention is formulated into pharmaceutical compositions appropriate to facilitate administration to animals or humans. Typical formulations can be prepared by mixing the recombinant virus with physiologically acceptable carriers, excipients or stabilizers, in the form of aqueous solutions or aqueous or non-aqueous suspensions. Carriers, excipients, modifiers or stabilizers are nontoxic at the dosages and concentrations employed. They include buffer systems such as phosphate, citrate, acetate and other inorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. The excipients may also have a release-modifying or absorption-modifying function.

In one embodiment the recombinant rhabdovirus of the invention is formulated into a pharmaceutical composition comprising Tris, arginine and optionally citrate. Tris is preferably used in a concentration of about 1 mM to about 100 mM. Arginine is preferably used in a concentration of about 1 mM to about 100 mM. Citrate may be present in a concentration up to 100 mM. A preferred formulation comprises about 50 mM Tris and 50 mM arginine.

The pharmaceutical composition may be provided as a liquid, a frozen liquid or in a lyophilized form. The frozen liquid may be stored at temperatures between about 0° C. and about −85° C. including temperatures between −70° C. and −85° C. and of about −15° C., −16° C., −17° C., −18° C., −19° C., −20° C., −21° C., −22° C., −23° C., −24° C. or about −25° C.

The recombinant rhabdovirus or pharmaceutical composition of the invention need not be, but is optionally, formulated with one or more agents currently used to prevent or treat the disorder in question. The effective amount of such other agents depends on the amount of recombinant antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the recombinant rhabodvirus or pharmaceutical composition of the invention (when used alone or in combination with one or more other additional therapeutic agents) will depend on the type of disease to be treated, the type of recombinant rhabdovirus, the severity and course of the disease, whether the recombinant rhabdovirus is administered for preventive or therapeutic purposes, previous therapy, the patient's clinical history and response to the recombinant rhabdovirus, and the discretion of the attending physician. The recombinant rhabdovirus or pharmaceutical composition of the invention suitably administered to the patient at one time or over a series of treatments.

Depending on the type and severity of the disease, about $10^8$ to $10^{13}$ infectious particles measured by $TCID_{50}$ of the recombinant rhabdovirus can be an initial candidate dosage for administration to the patient, whether, for example, by one or more separate administrations, or by continuous infusion. For repeated administrations over several days or longer, depending on the condition, the treatment would generally be sustained until a desired suppression of disease symptoms occurs. One exemplary dosage of the recombinant rhabdovirus would be in the range from about $10^8$ to $10^{13}$ infectious particles measured by $TCID_{50}$. Thus, one or more doses of about $10^8$, $10^9$, $10^{10}$, $10^{11}$, $10^{12}$, or $10^{13}$ infectious particles measured by $TCID_{50}$ (or any combination thereof) may be administered to the patient. Such doses may be administered intermittently, e.g. every week or every three weeks (e.g. such that the patient receives from about two to about twenty, or e.g. about six doses of the recombinant rhabdovirus). An initial higher loading dose, followed by one or more lower doses or vice versa may be administered. However, other dosage regimens may be useful. The progress of this therapy is easily monitored by conventional techniques and assays.

The efficacy of the recombinant rhabdovirus of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

The actual pharmaceutically effective amount or therapeutic dosage will of course depend on factors known by those skilled in the art such as age and weight of the patient, route of administration and severity of disease. In any case the recombinant rhabdovirus of the invention will be administered at dosages and in a manner which allows a pharmaceutically effective amount to be delivered based upon patient's unique condition.

Alternatively, the recombinant rhabdovirus or pharmaceutical composition of the invention may be delivered in a volume of from about 50 µl to about 100 ml including all numbers within the range, depending on the size of the area to be treated, the viral titer used, the route of administration, and the desired effect of the method.

For intratumoral administration the volume is preferably between about 50 µl to about 5 ml including volumes of about 100 µl, 200 µl, 300 µl, 400 µl, 500 µl, 600 µl, 700 µl, 800 µl, 900 µl, 1000 µl, 1100 µl, 1200 µl, 1300 µl, 1400 µl, 1500 µl, 1600 µl, 1700 µl, 1800 µl, 1900 µl, 2000 µl, 2500 µl, 3000 µl, 3500 µl, 4000 µl, or about 4500 µl. In a preferred embodiment the volume is about 1000 µl.

For systemic administration, e.g. by infusion of the recombinant rhabdovirus the volumes may be naturally higher. Alternatively, a concentrated solution of the recombinant rhabdovirus could be diluted in a larger volume of infusion solution directly before infusion.

In particular for intravenous administration the volume is preferably between 1 ml and 100 ml including volumes of about 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 25 ml, 30 ml, 35 ml, 40 ml, 45 ml, 50 ml, 55 ml, 60 ml, 70 ml, 75 ml, 80 ml, 85 ml, 90 ml, 95 ml, or about 100 ml. In a preferred embodiment the volume is between about 5 ml and 15 ml, more preferably the volume is about 6 ml, 7 ml, 8 ml, 9 ml, 10 ml, 11 ml, 12 ml, 13 ml, or about 14 ml.

Preferably the same formulation is used for intratumoral administration and intravenous administration. The doses and/or volume ratio between intratumoral and intravenous administration may be about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or about 1:20. For example, a doses and/or volume ratio of 1:1 means that the same doses and/or volume is administered intratumorally as well as intravenously, whereas e.g. a doses and/or volume ratio of about 1:20 means an intravenous administration dose and/or volume that is twenty times higher than the intratumoral administration dose and/or volume. Preferably, the doses and/or volume ratio between intratumoral and intravenous administration is about 1:9.

An effective concentration of a recombinant rhabdovirus desirably ranges between about $10^8$ and $10^{14}$ vector genomes per milliliter (vg/mL). The infectious units may be measured as described in McLaughlin et al., J Virol.; 62(6):1963-73 (1988). Preferably, the concentration is from about $1.5 \times 10^9$ to about $1.5 \times 10^{13}$, and more preferably from about $1.5 \times 10^9$ to about $1.5 \times 10^{11}$. In one embodiment, the effective concentration is about $1.5 \times 10^9$. In another embodiment, the effective concentration is about $1.5 \times 10^{10}$. In another embodiment, the effective concentration is about $1.5 \times 10^{11}$. In yet another embodiment, the effective concentration is about $1.5 \times 10^{12}$. In another embodiment, the effective concentration is about $1.5 \times 10^{13}$. In another embodiment, the effective concentration is about $1.5 \times 10^{14}$. It may be desirable to use the lowest effective concentration in order to reduce the risk of undesirable effects. Still other dosages in these ranges may be selected by the attending physician, taking into account the physical state of the subject, preferably human, being treated, the age of the subject, the particular type of cancer and the degree to which the cancer, if progressive, has developed.

An effective target concentration of a recombinant rhabdovirus may be expressed with the $TCID_{50}$. The $TCID_{50}$ can be determined for example by using the method of Spearman-Karber. Desirably ranges include an effective target concentration between $1 \times 10^8$/ml and $1 \times 10^{14}$/ml $TCID_{50}$. Preferably, the effective target concentration is from about $1 \times 10^9$ to about $1 \times 10^{12}$/ml, and more preferably from about $1 \times 10^9$ to about $1 \times 10^{11}$/ml. In one embodiment, the effective target concentration is about $1 \times 10^{19}$/ml. In a preferred embodiment the target concentration is $5 \times 10^{10}$/ml. In another embodiment, the effective target concentration is about $1.5 \times 10^{11}$/ml. In one embodiment, the effective target concentration is about $1 \times 10^{12}$/ml. In another embodiment, the effective target concentration is about $1.5 \times 10^{13}$/ml.

An effective target dose of a recombinant rhabdovirus may also be expressed with the $TCID_{50}$. Desirably ranges include a target dose between $1 \times 10^8$ and $1 \times 10^{14}$ $TCID_{50}$. Preferably, the target dose is from about $1 \times 10^9$ to about $1 \times 10^{13}$, and more preferably from about $1 \times 10^9$ to about $1 \times 10^{12}$. In one embodiment, the effective concentration is about $1 \times 10^{10}$. In a preferred embodiment, the effective concentration is about $1 \times 10^{11}$. In one embodiment, the effective concentration is about $1 \times 10^{12}$. In another embodiment, the effective concentration is about $1 \times 10^{13}$.

In another aspect, a kit or kit-of-parts containing materials useful for the treatment, prevention and/or diagnosis of the disorders described herein is provided. The kit or kit-of-parts comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is the recombinant rhabdovirus or pharmaceutical composition of the invention. The label or package insert indicates that the composition is used for treating the condition of choice.

Moreover, the kit or kit-of-parts may comprise (a) a first container with a composition contained therein, wherein the composition comprises the recombinant rhabdovirus or pharmaceutical composition of the invention; and (b) a second container with a composition contained therein, wherein the composition comprises a further cytotoxic or otherwise therapeutic agent, such as a PD-1 pathway inhibitor or SMAC mimetic. The kit or kit-of-parts in this embodiment of the invention may further comprise a package insert indicating that the compositions can be used to treat a particular condition, in particular cancer. Alternatively, or additionally, the kit or kit-of-parts may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In a further aspect, a recombinant rhabdovirus of the invention is used in combination with a device useful for the administration of the recombinant rhabdovirus, such as a syringe, injector pen, micropump, or other device. Preferably, a recombinant rhabdovirus of the invention is comprised in a kit of parts, for example also including a package insert with instructions for the use of the recombinant rhabdovirus.

Medical Uses

A further aspect of the invention provides a recombinant rhabdovirus encoding in its genome at least one CD80 extracellular domain Fc-fusion protein or a functional variant thereof for use in medicine.

The recombinant rhabdovirus of the invention efficiently induces tumor cell lysis combined with immunogenic cell death and stimulation of innate immune cells in the tumor microenvironment. Accordingly, the recombinant rhabdovirus of the invention are useful for the treatment and/or prevention of cancer.

In a further aspect, the recombinant rhabdovirus of the invention can be used in a method for treating and/or preventing cancer, comprising administering a therapeutically effective amount of a recombinant rhabdovirus to an individual suffering from cancer, thereby ameliorating one or more symptoms of cancer.

In yet a further aspect the invention further provides for the use of a recombinant rhabdovirus according to the invention for the manufacture of a medicament for treatment and/or prevention of cancer.

In yet a further aspect, the recombinant rhabdovirus of the invention can be used in a method for treating and/or preventing gastrointestinal cancer, lung cancer or head & neck cancer, comprising administering a therapeutically effective amount of a recombinant rhabdovirus to an individual suffering from gastrointestinal cancer, lung cancer or head & neck cancer, thereby ameliorating one or more symptoms of gastrointestinal cancer, lung cancer or head & neck cancer.

For the prevention or treatment of a disease, the appropriate dosage of recombinant rhabdovirus will depend on a variety of factors such as the type of disease to be treated, as defined above, the severity and course of the disease, whether the recombinant rhabdovirus is administered for preventive or therapeutic purposes, previous therapy, the patient's clinical history and response to the recombinant rhabdovirus, and the discretion of the attending physician. The recombinant rhabdovirus is suitably administered to the patient at one time or over a series of treatments.

In one aspect, the cancer is a solid cancer. The solid cancer may be brain cancer, endometrial cancer, vaginal cancer, anal cancer, colorectal cancer, oropharyngeal squamous cell carcinoma, gastric cancer, gastroesophageal junction adenocarcinoma, esophageal carcinoma, hepatocellular carcinoma, pancreatic adenocarcinoma, cholangiocarcinoma, bladder urothelial carcinoma, metastatic melanoma, prostate carcinoma, breast carcinoma, ovarian cancer, a head and neck squamous-cell carcinoma (HNSCC), glioblastoma, non-small cell lung cancer, brain tumor or small cell lung cancer. Preferred is the treatment of gastrointestinal cancer, lung cancer and head & neck cancer.

The recombinant rhabdovirus is administered by any suitable means, including oral, parenteral, subcutaneous, intratumoral, intravenous, intradermal, intraperitoneal, intrapulmonary, and intranasal. Parenteral infusions include intramuscular, intravenous, intraarterial, intraperitoneal, or subcutaneous administration. In addition, the recombinant rhabdovirus is suitably administered by pulse infusion. In one aspect, the dosing is given by injections, most preferably intravenous or subcutaneous injections, depending in part on whether the administration is brief or chronic.

Depending on the specific recombinant rhabdovirus of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The treatment schedule may include various regimens and in typical will require multiple doses administered to the patient over a period of one, two, three or four weeks optionally followed by one or more further rounds of treatment. In one aspect, the recombinant rhabdovirus of the invention is administered to the patient in up to 1, 2, 3, 4, 5, or 6 doses within a given period of time. Preferably, the first round of treatment(s) is concluded within three weeks. During the course of the three week treatment the recombinant rhabdovirus may be administered to the patient as described in the following schemes: (i) once on day 0 (ii) on day 0 and day 3; (iii) on day 0, day 3 and day 6; (iv) on day 0, day 3, day 6, and day 9; (v) on day 0 and day 5; (vi) on day 0, day 5 and day 10; (vii) on day 0, day 5, day 10 and day 15. These regimens may be repeated and a second or third round of treatment may be needed depending on the outcome of the first round of treatment. Calculated on the basis of the first round of treatments the second round of treatment preferably includes further treatments on day 21, day 42 and day 63. In a preferred embodiment the recombinant rhabdovirus of the invention is administered to the patient according the following scheme: on day 0, day 3, day 21, day 42 and day 63.

The term "suppression" is used herein in the same context as "amelioration" and "alleviation" to mean a lessening or diminishing of one or more characteristics of the disease. The recombinant rhabdovirus or pharmaceutical composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the recombinant rhabdovirus to be administered will be governed by such considerations, and is the minimum amount necessary to prevent, ameliorate, or treat clinical symptoms of cancer, in particular the minimum amount which is effective to these disorders.

In another aspect the recombinant rhabdovirus of the invention can be administered multiple times and in several doses. In one aspect, the first dose of the recombinant rhabdovirus is administered intratumorally and subsequent doses of the recombinant rhabdovirus are administered intravenously. In a further aspect, the first dose and at least one or more following doses of the recombinant rhabdovirus is/are administered intratumorally and subsequent doses of the recombinant rhabdovirus are administered intravenously. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

In another aspect, the first dose of the recombinant rhabdovirus is administered intravenously and subsequent doses of the recombinant rhabdovirus are administered intratumorally. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intravenous administration.

In another aspect, the recombinant rhabdovirus is administered intravenously and subsequent doses of the recombinant rhabdovirus are administered intratumorally.

In another aspect, the recombinant rhabdovirus is administered at each time point intravenously and intratumorally.

As stated above, the recombinant rhabdovirus of the invention have much utility for stimulating an immune response against cancer cells. The strong immune activating potential was observed to be restricted to the tumor microenvironment. Thus, in a preferred aspect, the recombinant rhabdovirus of the invention may be administered systemically to a patient. Systemic applicability is a crucial attribute, as many cancers are highly metastasized and it will permit the treatment of difficult to access as well as non-accesible tumor leasions. Due to this unique immune stimulating properties the recombinant rhabdovirus according to the invention are especially useful for treatment of metastasizing tumors.

Some patients develop resistance to checkpoint inhibitor therapy and it was observed that such patients seem to accumulate mutations in the IFN pathway. Therefore in one aspect, the recombinant rhabdovirus of the invention and in particular the recombinant vesicular stomatitis virus of the invention is useful for the treatment of patients who developed a resistance to checkpoint inhibitor therapy. Due to the unique immune promoting properties of the recombinant rhabdovirus and in particular the recombinant vesicular stomatitis virus of the invention such treated patients may become eligible for continuation of checkpoint inhibitor therapy.

In a preferred embodiment, the recombinant rhabdovirus of the invention and in particular the recombinant vesicular stomatitis virus of the invention is useful for the treatment of patients with non-small cell lung cancer which have completed checkpoint inhibitor therapy with either a PD-1 or PD-L1 inhibitor, e.g. antagonistic antibodies to PD-1 or PD-L1.

It is understood that any of the above pharmaceutical formulations or therapeutic methods may be carried out using any one of the inventive recombinant rhabdovirus or pharmaceutical compositions.

Combinations

The present invention also provide combination treatments/methods providing certain advantages compared to treatments/methods currently used and/or known in the prior art. These advantages may include in vivo efficacy (e.g. improved clinical response, extend of the response, increase of the rate of response, duration of response, disease stabilization rate, duration of stabilization, time to disease progression, progression free survival (PFS) and/or overall survival (OS), later occurrence of resistance and the like), safe and well tolerated administration and reduced frequency and severity of adverse events.

The recombinant rhabdovirus of the invention may be used in combination with other pharmacologically active ingredients, such as state-of-the-art or standard-of-care compounds, such as e.g. cytostatic or cytotoxic substances, cell proliferation inhibitors, anti-angiogenic substances, steroids, immune modulators/checkpoint inhibitors, and the like. The recombinant rhabdovirus of the invention may also be used in combination with radiotherapy.

Cytostatic and/or cytotoxic active substances which may be administered in combination with recombinant rhabdovirus of the invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF)), inhibitors are for example (anti-) growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g. PTK2/FAK inhibitors), protein protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; Flt3L as well as Flt3-stimulating antibodies or ligand mimetics; SIRPalpha & CD47 blocking therapeutics; and/or cyclin-dependent kinase 9 inhibitors.

Furthermore, the potential conversion of immunological "cold" into "hot" tumors, myeloid/dendritic cell activation in conjunction with CD80-Fc mediated T-cell activation further favourably interacts with therapeutic modalities, such as T-cell engagers. Thus, in one embodiment the recombinant rhabdovirus of the invention can be used in combination treatment with T-cell engagers, such as e.g. bispecific DLL3/CD3 binders, which provide T-cell receptor stimulation, but no co-stimulation. Additionally, potential clinical combination partners may also include tumor-vasculature modulating agents. Thus, in another embodiment the recombinant rhabdovirus of the invention can be used in combination treatment with tumor vasculature modulating agents, such as e.g. bispecific VEGF/ANG2 binders.

The recombinant rhabdovirus of the invention can be used in combination treatment with either a PD-1 pathway inhibitor or a SMACm/IAP antagonist. Such a combined treatment may be given as a non-fixed (e.g. free) combination of the substances or in the form of a fixed combination, including kit-of-parts.

In this context, "combination" or "combined" within the meaning of this invention includes, without being limited, a product that results from the mixing or combining of more than one active agent and includes both fixed and non-fixed (e.g. free) combinations (including kits) and uses, such as e.g. the simultaneous, concurrent, sequential, successive, alternate or separate use of the components or agents. The term "fixed combination" means that the active agents are both administered to a patient simultaneously in the form of a single entity or dosage. The term "non-fixed combination" means that the active agents are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active agents.

The invention provides for a recombinant rhabdovirus in combination with a PD-1 pathway inhibitor or a SMACm/IAP antagonist for use in the treatment of cancers as described herein, preferably for the treatment of solid cancers.

The invention also provides for the use of a recombinant rhabdovirus in combination with a PD-1 pathway inhibitor or a SMACm/IAP antagonist for the manufacture of a medicament for treatment and/or prevention of cancers as described herein, preferably for the treatment of solid cancers.

The invention further provides for a method for treating and/or preventing cancer, comprising administering a therapeutically effective amount of a recombinant rhabdovirus of the invention, and a PD-1 pathway inhibitor or a SMACm/IAP antagonist to an individual suffering from cancer, thereby ameliorating one or more symptoms of cancer. The recombinant rhabdovirus of the invention and the PD-1 pathway inhibitor or the SMACm/IAP antagonist may be administered concomitantly, sequentially or alternately.

The recombinant rhabdovirus of the invention and the PD-1 pathway inhibitor or a SMACm/IAP antagonist may be administered by the same administration routes or via different administration routes. Preferably, the PD-1 pathway inhibitor or SMACm/IAP antagonist is administered intravenously and the recombinant rhabdovirus of the invention is administered intratumorally. In another embodiment, the PD-1 pathway inhibitor or the SMACm/IAP antagonist is administered intravenously and the recombinant rhabdovirus of the invention is administered at least once intratumorally and subsequent doses of the recombinant rhabdovirus are administered intravenously. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration. In a preferred embodiment the PD-1 pathway inhibitor or the SMACm/IAP antagonists is administered 21 days after the initial intratumoral administration.

Particularly preferred are treatments with the recombinant rhabdovirus of the invention in combination with:
 (i) SMAC mimetica (SMACm)/IAP antagonists,
 (ii) immunotherapeutic agents, including anti-PD-1 and anti-PD-L1 agents and anti LAG3 agents, such as pembrolizumab and nivolumab and antibodies as disclosed in WO2017/198741.

A combination as herein provided comprises (i) a recombinant rhabdovirus of the invention and (iia) a PD-1 pathway inhibitor, preferably an antagonistic antibody which is directed against PD-1 or PD-L1 or (iib) a SMACm/IAP antagonists. Further provided is the use of such a combination comprising (i) and (iia) or (i) and (iib) for the treatment of cancers as described herein.

In another aspect a combination treatment is provided comprising the use of (i) a recombinant rhabdovirus of the invention and (iia) a PD-1 pathway inhibitor or (iib) a SMACm/IAP antagonists. In such combination treatment the recombinant rhabdovirus of the invention may be administered concomitantly, sequentially or alternately with the PD-1 pathway inhibitor or SMACm/IAP antagonists.

For example, "concomitant" administration includes administering the active agents within the same general time period, for example on the same day(s) but not necessarily at the same time. Alternate administration includes administration of one agent during a time period, for example over the course of a few days or a week, followed by administration of the other agent during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent during a second time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Sequential treatment schedules include administration of the recombinant rhabdovirus of the invention followed by administration of the PD-1 pathway inhibitor or the SMACm/IAP antagonists. Sequential treatment schedules also include administration of the PD-1 pathway inhibitor or the SMACm/IAP antagonists followed by administration of the recombinant rhabdovirus of the invention. Sequential treatment schedules may include administrations 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after each other.

A PD-1 pathway inhibitor within the meaning of this invention and all of its embodiments is a compound that inhibits the interaction of PD-1 with its receptor(s). A PD-1 pathway inhibitor is capable to impair the PD-1 pathway signaling, preferably mediated by the PD-1 receptor. The PD-1 inhibitor may be any inhibitor directed against any member of the PD-1 pathway capable of antagonizing PD-1 pathway signaling. The inhibitor may be an antagonistic antibody targeting any member of the PD-1 pathway, preferably directed against PD-1 receptor, PD-L1 or PD-L2.

Also, the PD-1 pathway inhibitor may be a fragment of the PD-1 receptor or the PD-1 receptor blocking the activity of PD1 ligands.

PD-1 antagonists are well-known in the art, e.g. reviewed by Li et al., Int. J. Mol. Sci. 2016, 17, 1151 (incorporated herein by reference). Any PD-1 antagonist, especially antibodies, such as those disclosed by Li et al. as well as the further antibodies disclosed herein below, can be used according to the invention. Preferably, the PD-1 antagonist of this invention and all its embodiments is selected from the group consisting of the following antibodies:

- pembrolizumab (anti-PD-1 antibody);
- nivolumab (anti-PD-1 antibody);
- pidilizumab (anti-PD-1 antibody);
- PDR-001 (anti-PD-1 antibody);
- PD1-1, PD1-2, PD1-3, PD1-4, and PD1-5 as disclosed herein below (anti-PD-1 antibodies)
- atezolizumab (anti-PD-L1 antibody);
- avelumab (anti-PD-L1 antibody);
- durvalumab (anti-PD-L1 antibody).

Pembrolizumab (formerly also known as lambrolizumab; trade name Keytruda; also known as MK-3475) disclosed e.g. in Hamid, O. et al. (2013) New England Journal of Medicine 369(2):134-44, is a humanized IgG4 monoclonal antibody that binds to PD-1; it contains a mutation at C228P designed to prevent Fc-mediated cytotoxicity. Pembrolizumab is e.g. disclosed in U.S. Pat. No. 8,354,509 and WO2009/114335. It is approved by the FDA for the treatment of patients suffering from unresectable or metastatic melanoma and patients with metastatic NSCLC.

Nivolumab (CAS Registry Number: 946414-94-4; BMS-936558 or MDX1106b) is a fully human IgG4 monoclonal antibody which specifically blocks PD-1, lacking detectable antibody-dependent cellular toxicity (ADCC). Nivolumab is e.g. disclosed in U.S. Pat. No. 8,008,449 and WO2006/121168. It has been approved by the FDA for the treatment of patients suffering from unresectable or metastatic melanoma, metastatic NSCLC and advanced renal cell carcinoma.

Pidilizumab (CT-011; Cure Tech) is a humanized IgG1k monoclonal antibody that binds to PD-1. Pidilizumab is e.g. disclosed in WO2009/101611.

PDR-001 or PDR001 is a high-affinity, ligand-blocking, humanized anti-PD-1 IgG4 antibody that blocks the binding of PD-L1 and PD-L2 to PD-1. PDR-001 is disclosed in WO2015/112900 and WO2017/019896.

Antibodies PD1-1 to PD1-5 are antibody molecules defined by the sequences as shown in Table 1, wherein HC denotes the (full length) heavy chain and LC denotes the (full length) light chain:

TABLE 1

| SEQ ID NO | Sequence name | Amino acid sequence |
|---|---|---|
| 14 | HC of PD1-1 | EVMLVESGGGLVQPGGSLRLSCTASGFTFSASAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 15 | LC of PD1-1 | EIVLTQSPATLSLSPGERATMSCRASENIDTSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 16 | HC of PD1-2 | EVMLVESGGGLVQPGGSLRLSCTASGFTFSASAMSWVRQAPGKGLEWVAYI SGGGGDTYYSSSVKGRFTISRDNAKNSLYLQMNSLRAEDTAVYYCARHSNP NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 17 | LC of PD1-2 | EIVLTQSPATLSLSPGERATMSCRASENIDTSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 18 | HC of PD1-3 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |

TABLE 1-continued

| SEQ ID NO | Sequence name | Amino acid sequence |
|---|---|---|
| 19 | LC of PD1-3 | EIVLTQSPATLSLSPGERATMSCRASENIDVSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 20 | HC of PD1-4 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 21 | LC of PD1-4 | EIVLTQSPATLSLSPGERATMSCRASENIDVSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 22 | HC of PD1-5 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 23 | LC of PD1-5 | EIVLTQSPATLSLSPGERATMSCRASENIDVSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |

Specifically, the anti-PD-1 antibody molecule described herein above has:

(PD1-1:) a heavy chain comprising the amino acid sequence of SEQ ID NO:14 and a light chain comprising the amino acid sequence of SEQ ID NO:15; or (PD1-2:) a heavy chain comprising the amino acid sequence of SEQ ID NO:16 and a light chain comprising the amino acid sequence of SEQ ID NO:17; or (PD1-3:) a heavy chain comprising the amino acid sequence of SEQ ID NO:18 and a light chain comprising the amino acid sequence of SEQ ID NO:19; or (PD1-4:) a heavy chain comprising the amino acid sequence of SEQ ID NO:20 and a light chain comprising the amino acid sequence of SEQ ID NO:21; or (PD1-5:) a heavy chain comprising the amino acid sequence of SEQ ID NO:22 and a light chain comprising the amino acid sequence of SEQ ID NO:23.

Atezolizumab (Tecentriq, also known as MPDL3280A) is a phage-derived human IgG1k monoclonal antibody targeting PD-L1 and is described e.g. in Deng et al. mAbs 2016; 8:593-603. It has been approved by the FDA for the treatment of patients suffering from urothelial carcinoma.

Avelumab is a fully human anti-PD-L1 IgG1 monoclonal antibody and described in e.g. Boyerinas et al. Cancer Immunol. Res. 2015; 3:1148-1157.

Durvalumab (MED14736) is a human IgG1k monoclonal antibody with high specificity to PD-L1 and described in e.g. Stewart et al. Cancer Immunol. Res. 2015; 3:1052-1062 or in Ibrahim et al. Semin. Oncol. 2015; 42:474-483.

Further PD-1 antagonists disclosed by Li et al. (supra), or known to be in clinical trials, such as AMP-224, MED10680 (AMP-514), REGN2810, BMS-936559, JS001-PD-1, SHR-1210, BMS-936559, TSR-042, JNJ-63723283, MED14736, MPDL3280A, and MSB0010718C, may be used as alternative or in addition to the above mentioned antagonists.

The INNs as used herein are meant to also encompass all biosimilar antibodies having the same, or substantially the same, amino acid sequences as the originator antibody, including but not limited to those biosimilar antibodies authorized under 42 USC § 262 subsection (k) in the US and equivalent regulations in other jurisdictions.

PD-1 antagonists listed above are known in the art with their respective manufacture, therapeutic use and properties.

In one embodiment the PD-1 antagonist is pembrolizumab.

In another embodiment the PD-1 antagonist is nivolumab.

In another embodiment the PD-1 antagonist is pidilizumab.

In another embodiment the PD-1 antagonist is atezolizumab.

In another embodiment the PD-1 antagonist is avelumab.

In another embodiment the PD-1 antagonist is durvalumab.

In another embodiment the PD-1 antagonist is PDR-001.
In another embodiment the PD-1 antagonist is PD1-1.
In another embodiment the PD-1 antagonist is PD1-2.
In another embodiment the PD-1 antagonist is PD1-3.
In another embodiment the PD-1 antagonist is PD1-4.
In another embodiment the PD-1 antagonist is PD1-5.

The SMAC mimetic within the meaning of this invention and all its embodiments is a compound which binds to IAP proteins and induces their degradation. Preferably, the SMAC mimetic within this invention and all its embodiments is selected from the group consisting of the following (A0):

- a SMAC mimetic (i.e. a compound) as (generically and/or specifically) disclosed in WO 2013/127729, or a pharmaceutically acceptable salt thereof;
- a SMAC mimetic (i.e. a compound) as (generically and/or specifically) disclosed in WO 2015/025018, or a pharmaceutically acceptable salt thereof;
- a SMAC mimetic (i.e. a compound) as (generically and/or specifically) disclosed in WO 2015/025019, or a pharmaceutically acceptable salt thereof;
- a SMAC mimetic (i.e. a compound) as (generically and/or specifically) disclosed in WO 2016/023858, or a pharmaceutically acceptable salt thereof;
- a SMAC mimetic (i.e. a compound) as (generically and/or specifically) disclosed in WO 2008/0016893, or a pharmaceutically acceptable salt thereof;
- LCL161, i.e. compound A in example 1 of WO 2008/016893 (page 28/29; [122]), or a pharmaceutically acceptable salt thereof;
- the SMAC mimetic known as Debio-1143, or a pharmaceutically acceptable salt thereof;
- the SMAC mimetic known as birinapant, or a pharmaceutically acceptable salt thereof;
- the SMAC mimetic known as ASTX-660, or a pharmaceutically acceptable salt thereof;
- the SMAC mimetic known as CUDC-427, or a pharmaceutically acceptable salt thereof;
- any one of the SMAC mimetics 1 to 26 in table 2 or a pharmaceutically acceptable salt thereof:

TABLE 2

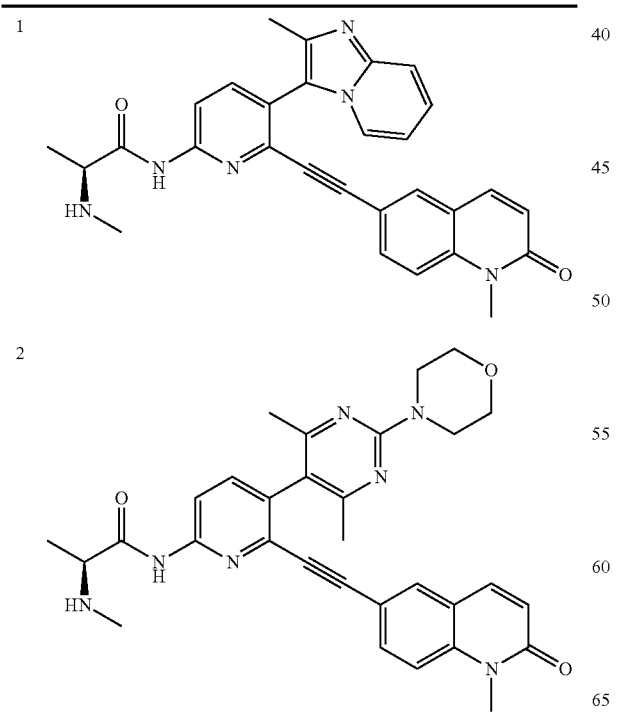

TABLE 2-continued

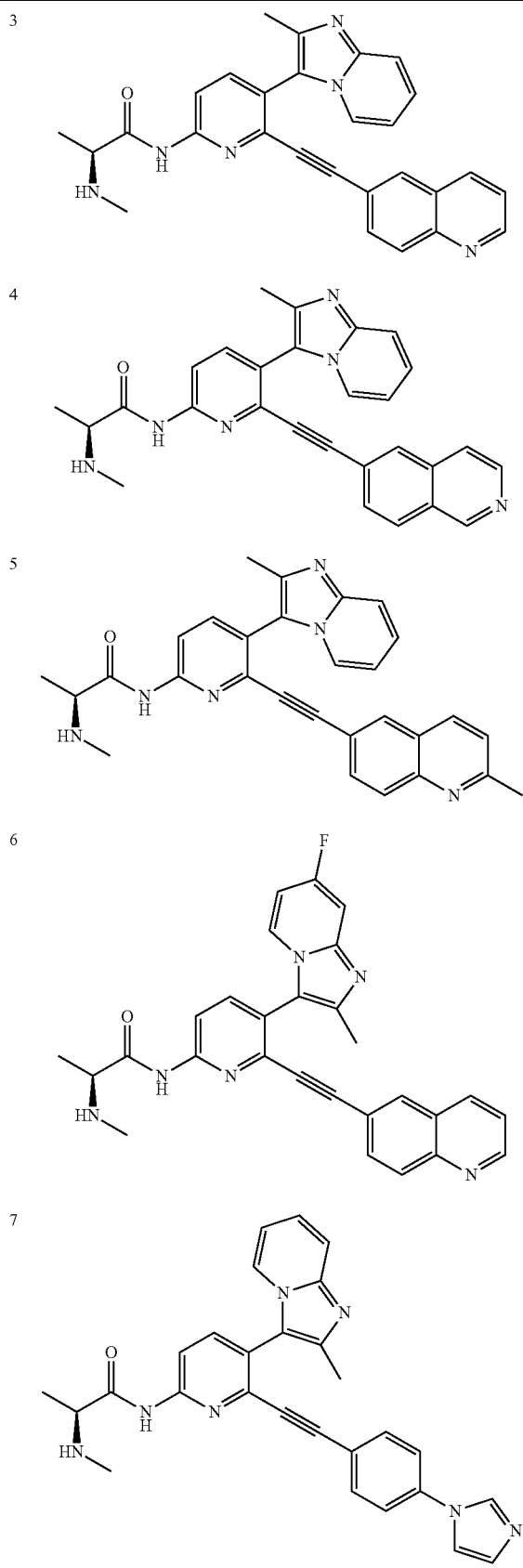

TABLE 2-continued
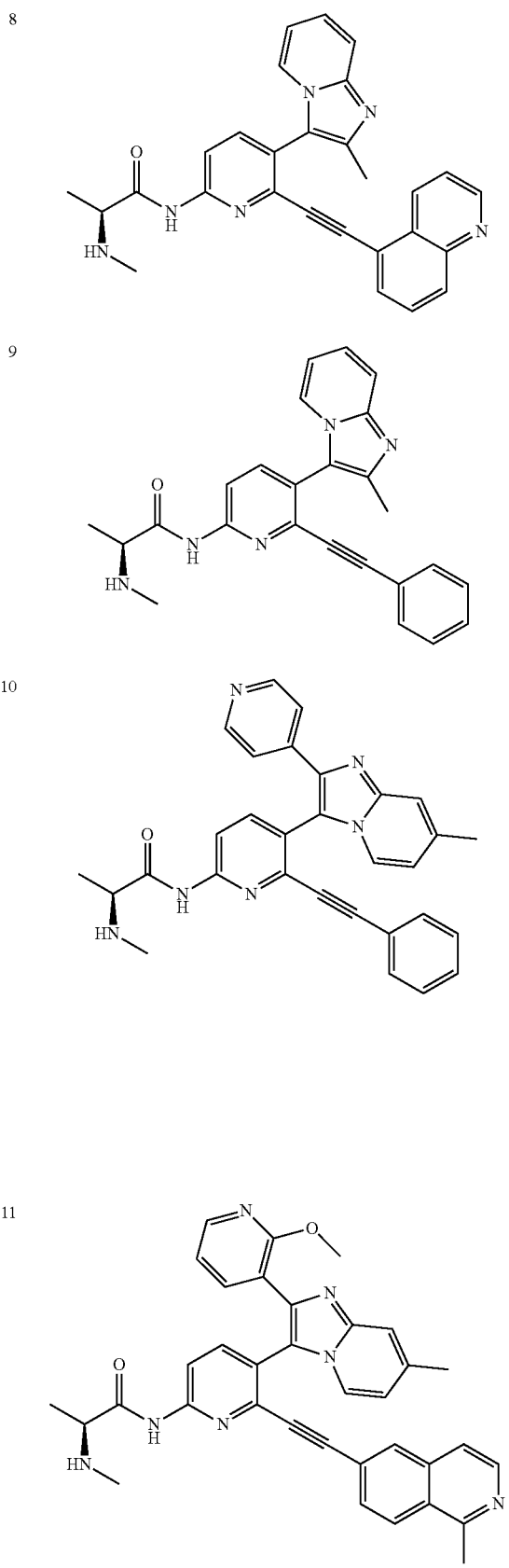
TABLE 2-continued
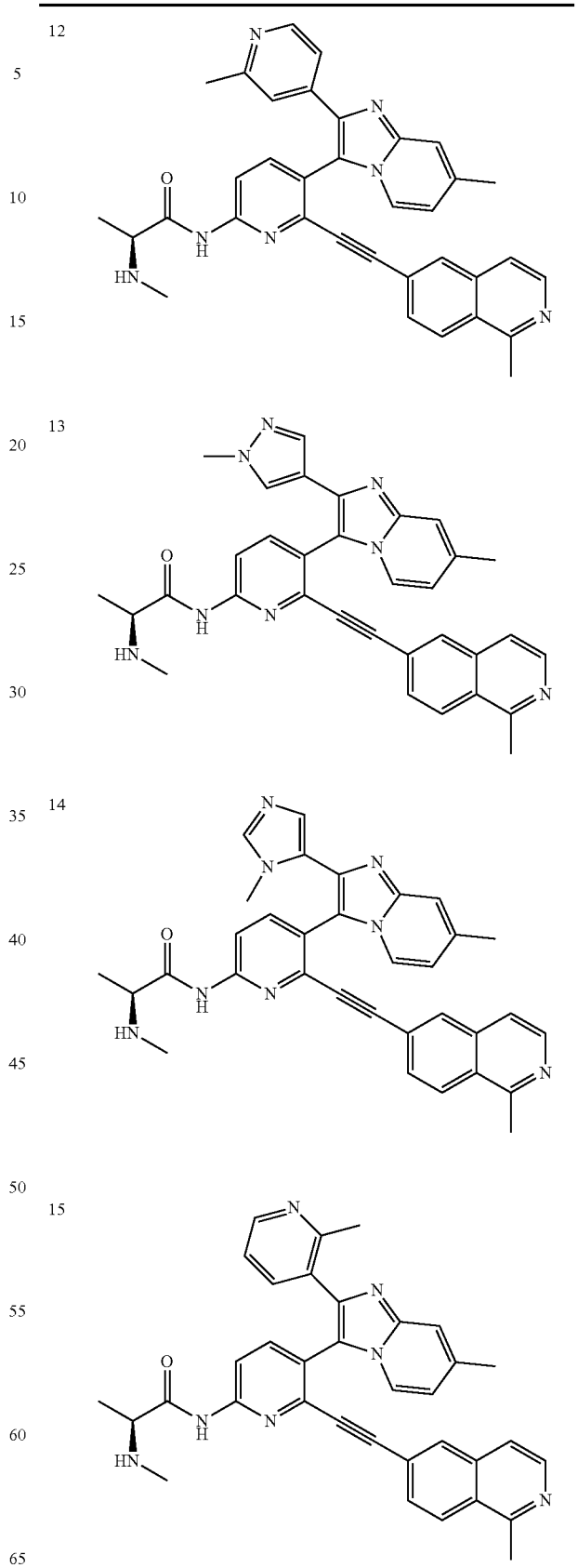

TABLE 2-continued
16 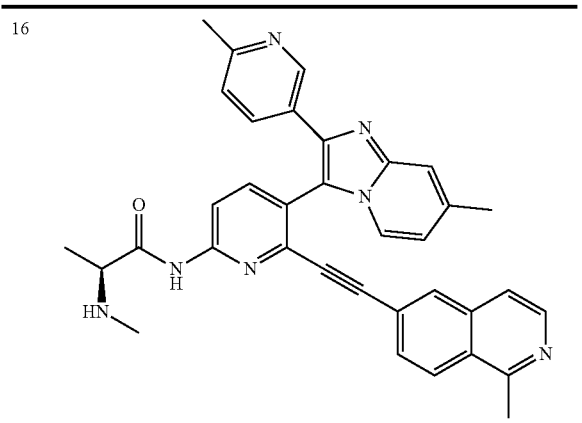
17 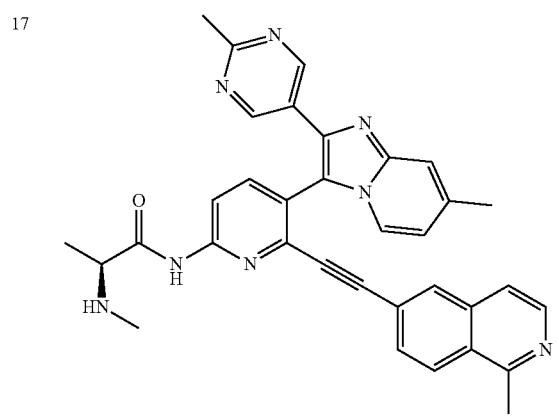
18 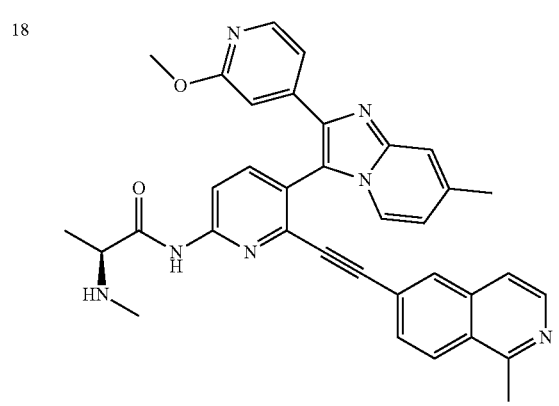
19 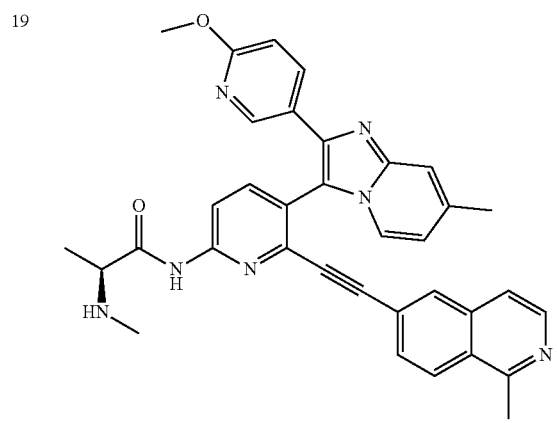
TABLE 2-continued
20 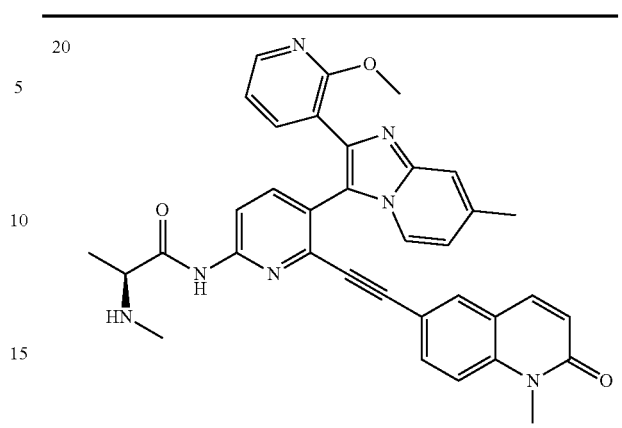
21 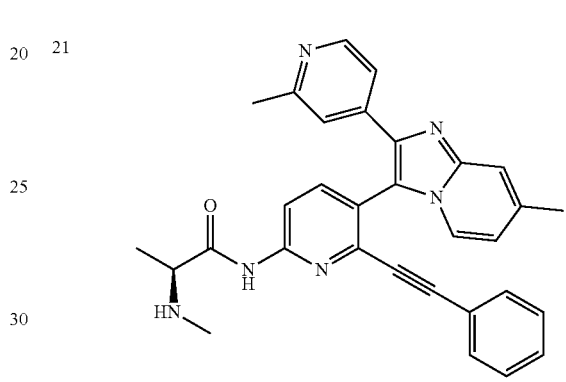
22 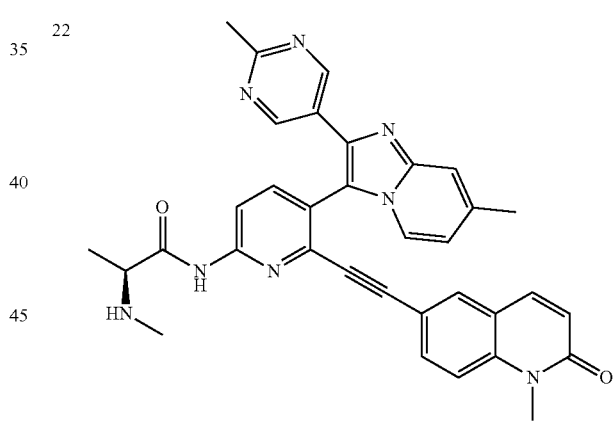
23 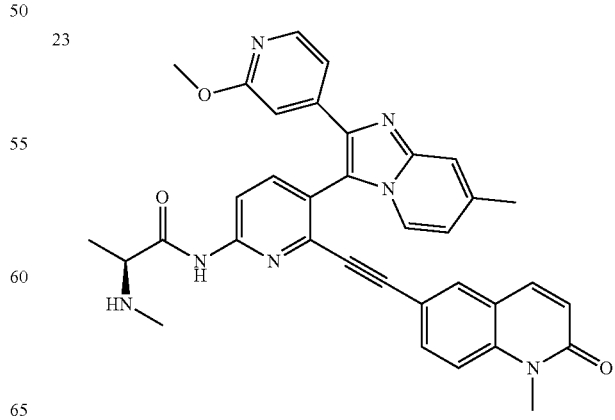

TABLE 2-continued

24 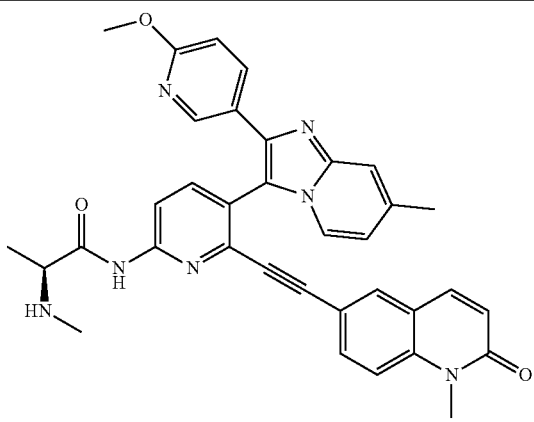

25 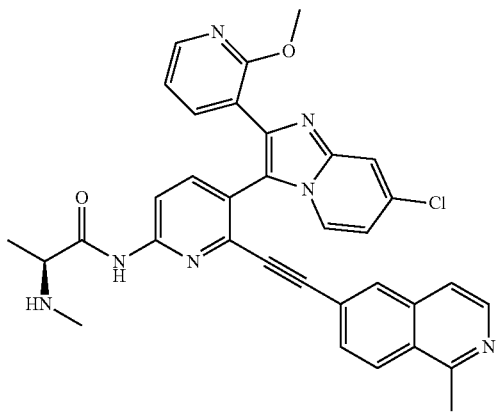 [SMILES: CN[C@@H](C)C(=O)Nc1ccc(-c2c(-c3cccnc3OC)nc3cc(Cl)ccn23)c(C#Cc2ccc3c(C)nccc3c2)n1]

26 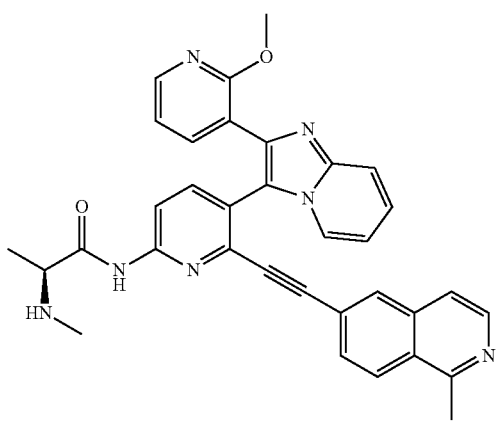 [SMILES: CN[C@@H](C)C(=O)Nc1ccc(-c2c(-c3cccnc3OC)nc3ccccn23)c(C#Cc2ccc3c(C)nccc3c2)n1]

Example compounds 1 to 10 in Table 2 are disclosed in WO 2013/127729. Example compounds 11 to 26 in Table 2 are disclosed in WO 2016/023858.

The term "SMAC mimetic/IAP antagonist" as used herein also includes the SMAC mimetics listed above in the form of a tautomer, of a pharmaceutically acceptable salt, of a hydrate or of a solvate (including a hydrate or solvate of a pharmaceutically acceptable salt). It also includes the SMAC mimetic in all its solid, preferably crystalline, forms and in all the crystalline forms of its pharmaceutically acceptable salts, hydrates and solvates (including hydrates and solvates of pharmaceutically acceptable salts).

All SMAC mimetics listed above are known in the art with the respective synthesis and properties. All patent applications referred to above are incorporated by reference in their entirety.

In one embodiment the SMAC mimetic is LCL161 or a pharmaceutically acceptable salt thereof (A1).

In another embodiment the SMAC mimetic is compound 1 in table 2 or a pharmaceutically acceptable salt thereof (A2).

In another embodiment the SMAC mimetic is compound 2 in table 2 or a pharmaceutically acceptable salt thereof (A3).

In another embodiment the SMAC mimetic is compound 3 in table 2 or a pharmaceutically acceptable salt thereof (A4).

In another embodiment the SMAC mimetic is compound 4 in table 2 or a pharmaceutically acceptable salt thereof (A5).

In another embodiment the SMAC mimetic is compound 5 in table 2 or a pharmaceutically acceptable salt thereof (A6).

In another embodiment the SMAC mimetic is compound 6 in table 2 or a pharmaceutically acceptable salt thereof (A7).

In another embodiment the SMAC mimetic is compound 7 in table 2 or a pharmaceutically acceptable salt thereof (A8).

In another embodiment the SMAC mimetic is compound 8 in table 2 or a pharmaceutically acceptable salt thereof (A9).

In another embodiment the SMAC mimetic is compound 9 in table 2 or a pharmaceutically acceptable salt thereof (A10).

In another embodiment the SMAC mimetic is compound 10 in table 2 or a pharmaceutically acceptable salt thereof (A11).

In another embodiment the SMAC mimetic is compound 11 in table 2 or a pharmaceutically acceptable salt thereof (A12).

In another embodiment the SMAC mimetic is compound 12 in table 2 or a pharmaceutically acceptable salt thereof (A13).

In another embodiment the SMAC mimetic is compound 13 in table 2 or a pharmaceutically acceptable salt thereof (A14).

In another embodiment the SMAC mimetic is compound 14 in table 2 or a pharmaceutically acceptable salt thereof (A15).

In another embodiment the SMAC mimetic is compound 15 in table 2 or a pharmaceutically acceptable salt thereof (A16).

In another embodiment the SMAC mimetic is compound 16 in table 2 or a pharmaceutically acceptable salt thereof (A17).

In another embodiment the SMAC mimetic is compound 17 in table 2 or a pharmaceutically acceptable salt thereof (A18).

In another embodiment the SMAC mimetic is compound 18 in table 2 or a pharmaceutically acceptable salt thereof (A19).

In another embodiment the SMAC mimetic is compound 19 in table 2 or a pharmaceutically acceptable salt thereof (A20).

In another embodiment the SMAC mimetic is compound 20 in table 2 or a pharmaceutically acceptable salt thereof (A21).

In another embodiment the SMAC mimetic is compound 21 in table 2 or a pharmaceutically acceptable salt thereof (A22).

In another embodiment the SMAC mimetic is compound 22 in table 2 or a pharmaceutically acceptable salt thereof (A23).

In another embodiment the SMAC mimetic is compound 23 in table 2 or a pharmaceutically acceptable salt thereof (A24).

In another embodiment the SMAC mimetic is compound 24 in table 2 or a pharmaceutically acceptable salt thereof (A25).

In another embodiment the SMAC mimetic is compound 25 in table 2 or a pharmaceutically acceptable salt thereof (A26).

In another embodiment the SMAC mimetic is compound 26 in table 2 or a pharmaceutically acceptable salt thereof (A27).

All embodiments (A1) to (A27) are preferred embodiments of embodiment (A0) in respect of the nature of the SMAC mimetic.

In a preferred embodiment relating to the combination treatments the recombinant rhabdovirus is a recombinant vesicular stomatitis virus encoding in its genome at least one CD80 extracellular domain Fc-fusion protein or a functional variant thereof, preferably human CD80 extracellular domain, selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

In a further preferred embodiment relating to the combination treatment the recombinant rhabdovirus is a recombinant vesicular stomatitis virus encoding in its genome a vesicular stomatitis virus nucleoprotein (N), large protein (L), phosphoprotein (P), matrix protein (M), glycoprotein (G) and at least one CD80 extracellular domain Fc-fusion protein or a functional variant thereof, preferably human CD80 extracellular domain, wherein the CD80 extracellular domain Fc-fusion protein or functional variant thereof is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3, wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a more preferred embodiment relating to the combination treatments the recombinant rhabdovirus is a recombinant vesicular stomatitis virus encoding in its genome at least one CD80 extracellular domain Fc-fusion protein or a functional variant thereof, preferably human CD80 extracellular domain, wherein the CD80 extracellular domain Fc-fusion protein or functional variant thereof comprises or consists of SEQ ID NO:3 or has at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:3, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

Virus Generation, Production and Virus Producing Cell

The invention also provides a virus producing cell, characterized in that the cell produces a recombinant rhabdovirus or recombinant vesicular stomatitis virus according to the invention.

The cell may be of any origin and may be present as isolated cell or as a cell comprised in a cell population. It is preferred that the cell producing a recombinant rhabdovirus or recombinant vesicular stomatitis virus is a mammalian cell. In a more preferred embodiment, the virus producing cell of the invention is characterized in that the mammalian cell is a multipotent adult progenitor cell (MAPC), a neural stem cell (NSC), a mesenchymal stem cell (MSC), a HeLa cell, a HEK cell, any HEK293 cell (e.g. HEK293F or HEK293T), a Chinese hamster ovary cell (CHO), a baby hamster kidney (BHK) cell or a Vero cell or a bone marrow derived tumor infiltrating cell (BM-TIC).

Alternatively, the virus producing cell may be a human cell, monkey cell, mouse cell or hamster cell. The skilled person is aware of methods suitable for use in testing whether a given cell produces a virus and, thus, whether a particular cell falls within the scope of this invention. In this respect, the amount of virus produced by the cell of the invention is not particularly limited. Preferred viral titers are $\geq 1\times10^7$ TCID$_{50}$/ml or $\geq 1\times10^8$ genome copies/ml in the crude supernatants of the given cell culture after infection without further downstream processing.

In a particular embodiment, the virus producing cell of the invention is characterized in that the cell comprises one or more expression cassettes for the expression of at least one of the genes selected from the group consisting of genes n, l, p and m coding for proteins N, L, P and M of the VSV and a gene gp coding for LCMV-GP, Dandenong-GP or Mopeia-GP glycoprotein.

Virus producing cells in the meaning of the invention include classical packaging cells for the production of recombinant rhabdovirus from non-replicable vectors as well as producer cells for the production of recombinant rhabdovirus from vectors capable of reproduction. Packaging cells usually comprise one or more plasmids for the expression of essential genes which lack in the respective vector to be packaged and/or are necessary for the production of virus. Such cells are known to the skilled person who can select appropriate cell lines suitable for the desired purpose.

Recombinant rhabdovirus of the invention can be produced according to methods known to the skilled artisan and include without limitation (1) using cDNAs transfected into a cell or (2) a combination of cDNAs transfected into a helper cell, or (3) cDNAs transfected into a cell, which is further infected with a helper/minivirus providing in trans the remaining components or activities needed to produce either an infectious or non-infectious recombinant rhabdovirus. Using any of these methods (e.g., helper/minivirus, helper cell line, or cDNA transfection only), the minimum components required are a DNA molecule containing the cis-acting signals for (1) encapsidation of the genomic (or antigenomic) RNA by the Rhabdovirus N protein, P protein and L protein and (2) replication of a genomic or antigenomic (replicative intermediate) RNA equivalent.

A replicating element or replicon is a strand of RNA minimally containing at the 5' and 3' ends the leader sequence and the trailer sequence of a rhabdovirus. In the genomic sense, the leader is at the 3' end and the trailer is at the 5' end. Any RNA-placed between these two replication signals will in turn be replicated. The leader and trailer regions further must contain the minimal cis-acting elements for purposes of encapsidation by the N protein and for polymerase binding which are necessary to initiate transcription and replication. For preparing recombinant rhabdovirus a minivirus containing the G gene would also contain a leader region, a trailer region and a G gene with the appropriate initiation and termination signals for producing a G protein mRNA. If the minivirus further comprises an M gene, the appropriate initiation and termination signals for producing the M protein mRNA must also present.

For any gene contained within the recombinant rhabdovirus genome, the gene would be flanked by the appropriate transcription initiation and termination signals which will allow expression of those genes and production of the protein products (Schnell et al., Journal of Virology, p. 2318-2323, 1996). To produce "non-infectious" recombinant rhabdovirus, the recombinant rhabdovirus must have the minimal replicon elements and the N, P, and L proteins and it must contain the M gene. This produces virus particles that are budded from the cell but are non-infectious particles. To produce "infectious" particles, the virus particles must additionally comprise proteins that can mediate virus particle binding and fusion, such as through the use of an attachment protein or receptor ligand. The native receptor ligand of rhabdoviruses is the G protein.

Any cell that would permit assembly of the recombinant rhabdovirus can be used. One method to prepare infectious virus particles comprises an appropriate cell line infected with a plasmid encoding for a T7 RNA polymerase or other suitable bacteriophage polymerase such as the T3 or SP6 polymerases. The cells may then be transfected with individual cDNA containing the genes encoding the G, N, P, L and M rhabdovirus proteins. These cDNAs will provide the proteins for building a recombinant rhabdovirus particle. Cells can be transfected by any method known in the art.

Also transfected into the cell line is a "polycistronic cDNA" containing the rhabdovirus genomic RNA equivalent. If the infectious, recombinant rhabdovirus particle is intended to be lytic in an infected cell, then the genes encoding for the N, P, M and L proteins must be present as well as any heterologous nucleic acid segment. If the infectious, recombinant rhabdovirus particle is not intended to be lytic, then the gene encoding the M protein is not included in the polycistronic DNA. By "polycistronic cDNA" it is meant a cDNA comprising at least transcription units containing the genes which encode the N, P and L proteins. The recombinant rhabdovirus polycistronic DNA may also contain a gene encoding a protein variant or polypeptide fragment thereof, or a therapeutic nucleic acid or protein. Alternatively, any protein to be initially associated with the viral particle first produced or fragment thereof may be supplied in trans.

Also contemplated is a polycistronic cDNA comprising a gene encoding for a CD80 extracellular domain Fc-fusion protein. The polycistronic cDNA contemplated may contain a gene encoding a protein variant, a gene encoding a reporter, a therapeutic nucleic acid, and/or either the N-P-L genes or the N-P-L-M genes. The first step in generating a recombinant rhabdovirus is expression of an RNA that is a genomic or antigenomic equivalent from a cDNA. Then that RNA is packaged by the N protein and then replicated by the P/L proteins. The recombinant virus thus produced can be recovered. If the G protein is absent from the recombinant RNA genome, then it is typically supplied in trans. If both the G and the M proteins are absent, then both are supplied in trans. For preparing "non-infectious rhabdovirus" particles, the procedure may be the same as above, except that the polycistronic cDNA transfected into the cells would contain the N, P and L genes of the rhabdovirus only. The polycistronic cDNA of non-infectious rhabdovirus particles may additionally contain a gene encoding a protein.

Transfected cells are usually incubated for at least 24 hr at the desired temperature, usually about 37 degrees. For non-infectious virus particles, the supernatant is collected and the virus particles isolated. For infectious virus particles, the supernatant containing virus is harvested and transferred to fresh cells. The fresh cells are incubated for approximately 48 hours, and the supernatant is collected.

Other features and advantages of the present invention will become apparent from the following more detailed Examples which illustrate, by way of example, the principles of the invention.

EXAMPLES

Example 1

Generation of VSV-GP-huCD80-Fc (IgG1)—Viral Rescue

The genome of the oncolytic virus VSV-GP was engineered to encode for the CD80-Fc gene to locally express the CD80-Fc fusion protein at the tumor site during viral replication. Replication competent VSV-GP-CD80-Fc virus variants were generated by means of reverse genetics (cloning the gene of interest (GOI), virus rescue and repeated plaque purification) from bacterial plasmids that contain the cDNA for the complete viral genome of VSV-GP and human CD80-Fc. pVSV-GP-CD80-Fc plasmids were based on the plasmid pVSV-XN1 (Schnell et al.], which contains the complete cDNA genome of VSV Indiana serotype under the control of the T7 promoter. In order to generate pVSV-GP-CD80-Fc variants, the whole sequence for the VSV G envelope protein was substituted by the codon optimized sequence of GP envelope protein from Lymphocytic choriomeningitis virus (LCMV, WE-HPI strain). Additionally, a synthetic nucleic acid coding for a CD80-Fc gene was inserted between the glycoprotein GP and the viral polymerase L by Gibson assembly. Transcription of the CD80-Fc gene in the context of viral infection is ensured by an extra VSV start signal sequence at the 3' end and of an additional stop signal sequence at the 5' end of the CD80-Fc open reading frame.

Infectious viruses were recovered (or rescued) from the plasmid cDNAs by transfection of HEK293T or any other VSV permissive cell line by standard transfection methods (e.g. $CaPO_4$ precipitation, liposomal DNA delivery). Briefly, HEK293T cells were transfected with pSF-CAG-amp-based expression plasmids encoding the VSV proteins N, P, and L as well as a codon-optimized T7-polymerase. Additionally, the plasmid coding the viral genomic cDNA of VSV-GP, VSV-GP-CD80-Fc or a variant thereof was co-transfected. In a first step of the rescue process, the T7 polymerase transcribes the virus RNA genome from the plasmid coded virus cDNA. In a second step, VSV-L and -P proteins, which are exogenously expressed from the co-transfected plasmids, further amplify the viral RNA genomes. The viral RNA genomes are co-transcriptionally encapsulated by the VSV-N protein. Additionally, the P/L polymerase complex allows transcription of the full set of viral gene products N, P, M, GP and L as well as the inserted CD80-Fc variants. The viral RNA genomes are subsequently packaged into infectious VSV particles containing the ribonucleoprotein, the matrix protein and the viral envelope GP. Virus particles are released from the cells by budding.

Rescued viruses were initially passaged on permissive cell lines such as e.g. HEK293T. Several rounds of plaque purification were performed before generation of a virus seed stock by standard methods. Briefly, HEK293T cells were infected with serial ten-fold dilutions of the rescued pre-seeds. After approximately two hours, cell monolayers were washed twice and overlaid with media containing 0.8% of low melt agarose. 24 h to 48 h post infection, plaques were picked and virus was used for an additional round of plaque-purification or virus seed stocks were generated.

Example 2

Validation of Viral Fitness—$TCID_{50}$/Cell Killing

FIG. 3A-B

Figure 3:
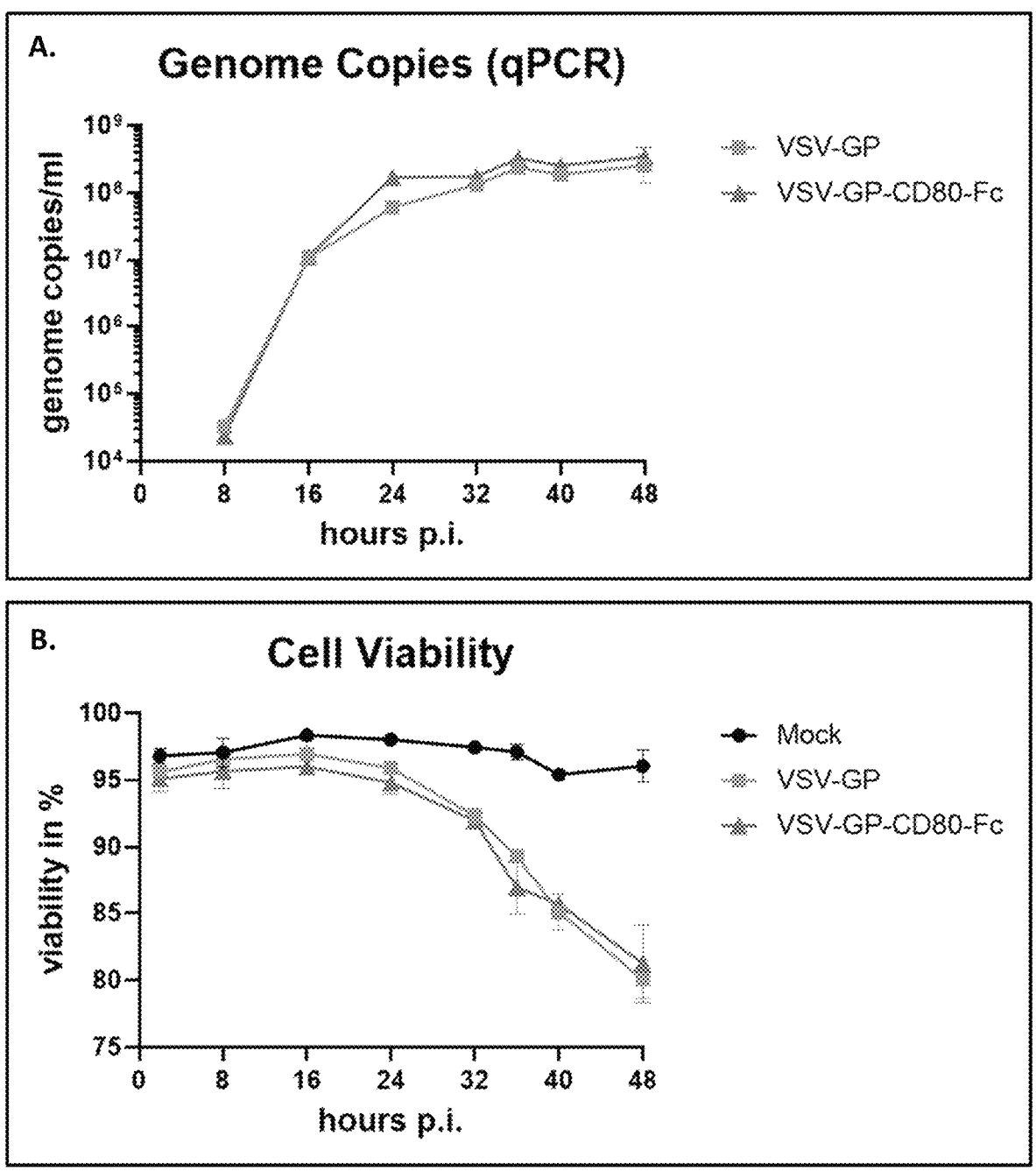
FIG. 3A-B Replication (A) and Viability (B) of VSV-GP-CD80-Fc relative to the parental virus VSV-GP were compared. HEK293F cells were infected with either VSV-GP or VSV-GP-CD80-Fc. Y-axis shows cell viability in percent or genome copies per ml. Both cell viability and replication were monitored for up to 48 h after infection (x-axis: hours post infection).
Figure 4:
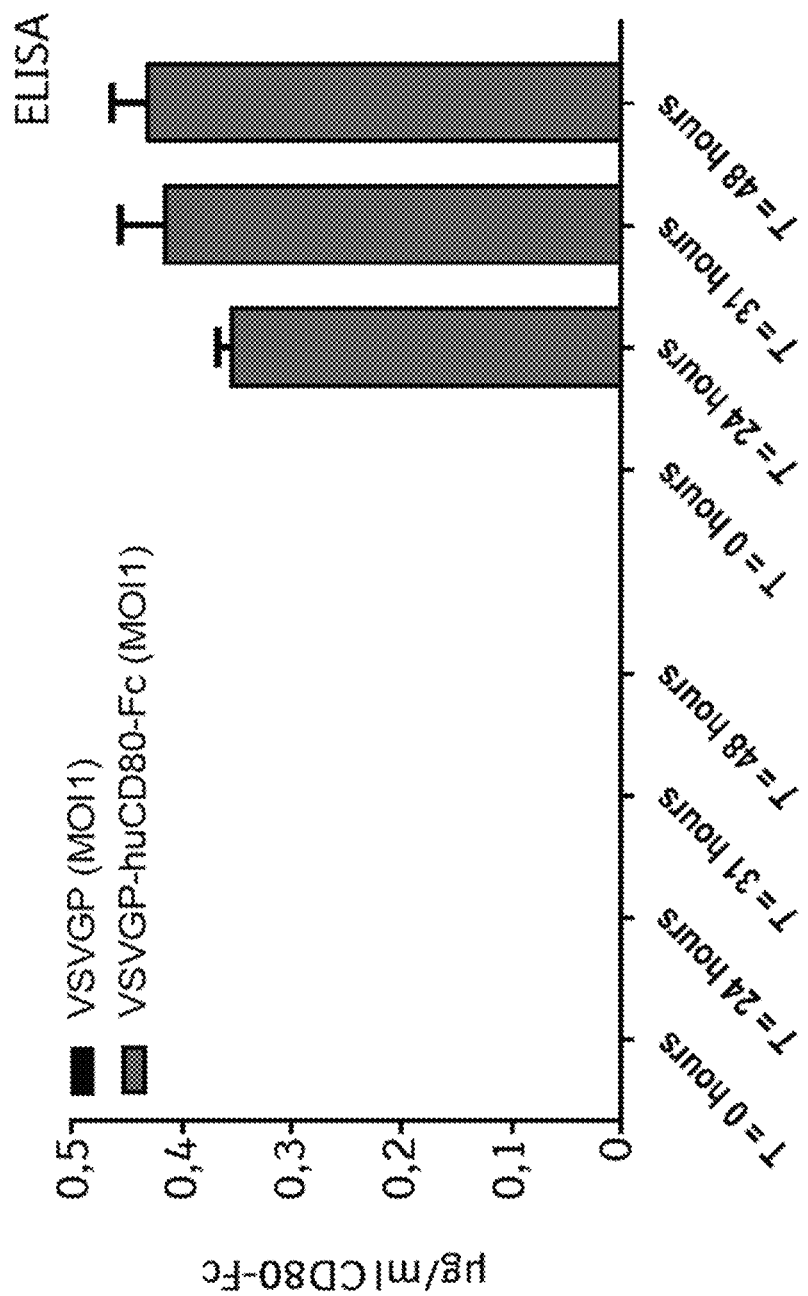
FIG. 4 Soluble CD80-Fc detection by ELISA in tissue culture supernatants from HEK293 cells infected with VSV-GP or VSV-GP-CD80-Fc each with a mulplicity of infection of 1 (MOI 1). CD80-Fc expression (y-axis in µg/ml) was determined for different time points after infection for up to 48 hours (x-axis).

HEK293F cells grown in suspension culture (media Freestyle™ 293 Expression Medium (ThermoFisher Scientific)) were infected with a low MOI (0.0005) of either VSV-GP or VSV-GP-CD80-Fc. On the day of infection, the cells had a confluence of 60-70%. One well was counted (Countess™ cell counter, Invitrogen) before infecting the other wells with 0.005 MOI of one of the virus constructs VSV-GP (GP) or VSV-GP-CD80-Fc. Culture supernatants (3 mL total volume) were harvested and samples were analyzed 8 h, 16 h, 24 h, 32 h, 40 h and 48 h post infection for viral replication and cell killing. Viral replication was assessed using detection of viral genomes by qPCR in the supernatant of the cultures at the indicated timepoints (FIG. 3A). Virus induced cell killing was assessed by counting the viable cells in culture samples at the indicated time points (FIG. 3B). Both viruses behave the same way indicating that addition of the human CD80-Fc transgene does not affect the viral fitness.

Example 3

Cargo Expression—ELISA

FIG. 4

Supernatants from VSV-GP-CD80-Fc infected HEK293 cells were analyzed at different time points following viral infection using an ELISA. Expression of the virally encoded CD80-Fc fusion protein by infected, mammalian cells was validated by infecting HEK293 cells with the parental virus VSV-GP or the CD80-Fc encoding, new virus VSV-GP-CD80-Fc, both at an MOI1. Expression of the CD80-Fc transgene, as measured by ELISA in tissue culture supernatants, was readily detectable at 24, 31 and 48 hours post infection of the cells.

Example 4

VSV-GP-huCD80-Fc (In Vivo)—CT26.CL25-IFNARKO Tumor Model (High Cargo Expression)

FIG. 5A-B

Using the CT26.CL25-IFARKO tumor model, which has been engineered to lack the interferon alpha receptor (IFNAR), to better reflect the human patient situation and allow for improved virus replication as well as cargo expression in the murine system, the parental virus VSV-GP and the CD80-Fc encoding, new virus VSV-GP-CD80-Fc were compared back-to-back. For this purpose the two viruses were administered intravenously (i.v.) at a dose of $2 \times 10^7$ $TCID_{50}$ on day 0 and day 3 (survival graph) in mice with established tumors. As depicted in panel (A) the parental virus VSV-GP did not demonstrate a significantly improved survival of tumor bearing animals at this low viral dose, while treatment with the cargo-armed, new virus VSV-GP-CD80-Fc resulted in a pronounced survival benefit as compared to the control and VSV-GP treated animals. Furthermore, treatment with the CD80-Fc encoding virus did not result in an increased body weight loss as compared to the control and VSV-GP treated animals (B), arguing for the safety of this novel virus.

Example 5

VSV-GP-huCD80-Fc (In Vivo)—B16-F1-OVA & EMT-6 Tumor Models (Low Cargo Expression)
FIG. 6A-C and FIG. 7A-B The lowly permissive tumor models B16-F1-OVA (FIG. 6A-C) and EMT-6 (FIG. 7A-B), which only allow for minimal viral replication and accordingly cargo (CD80-Fc) expression were treated with two intra tumoral (i.t.) injections of the parental virus VSV-GP or the CD80-Fc encoding, new virus VSV-GP-CD80-Fc on day 0 and day 3. Only mice with well-established tumors were used for the injections. Treatment of the B16-F1-OVA tumor models with VSV-GP-CD80-Fc resulted in an improved tumor growth delay as compared to control and VSV-GP. In the EMT-6 tumor model treatment with VSV-GP-CD80-Fc resulted in an improved tumor clearance rate (33% of treated animals) as compared to control (0% of treated animals) and VSV-GP (8% of treated animals) treated mice. These results argue for an upside potential of the cargo-armed novel virus VSV-GP-CD80-Fc over the parental virus VSV-GP even in tumors with a low level of virus replication and cargo expression, which is intimately linked to the ability of the virus to replicate.

Example 6

Figure 8:
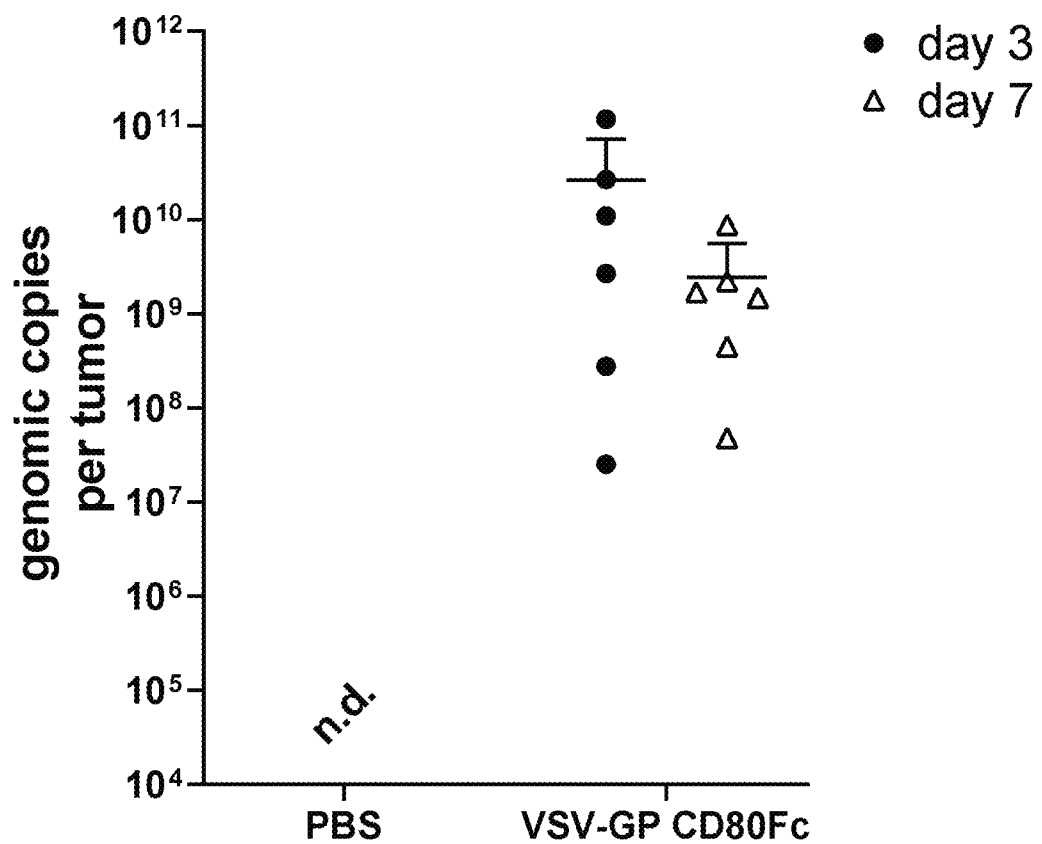
FIG. 8 VSV-GP-CD80-Fc replication within infected CT26.CL25-IFNARKO tumors taken from treated mice as determined by viral genome copy quantification using qPCR on day 3 & 7 post infection. Mice were treated either with PBS or $10^8$ $TCID_{50}$ VSV-GP-CD80-Fc and the viral genome copies per tumor (y-axis) were determined after 3 or 7 days respectively.
Figure 9:
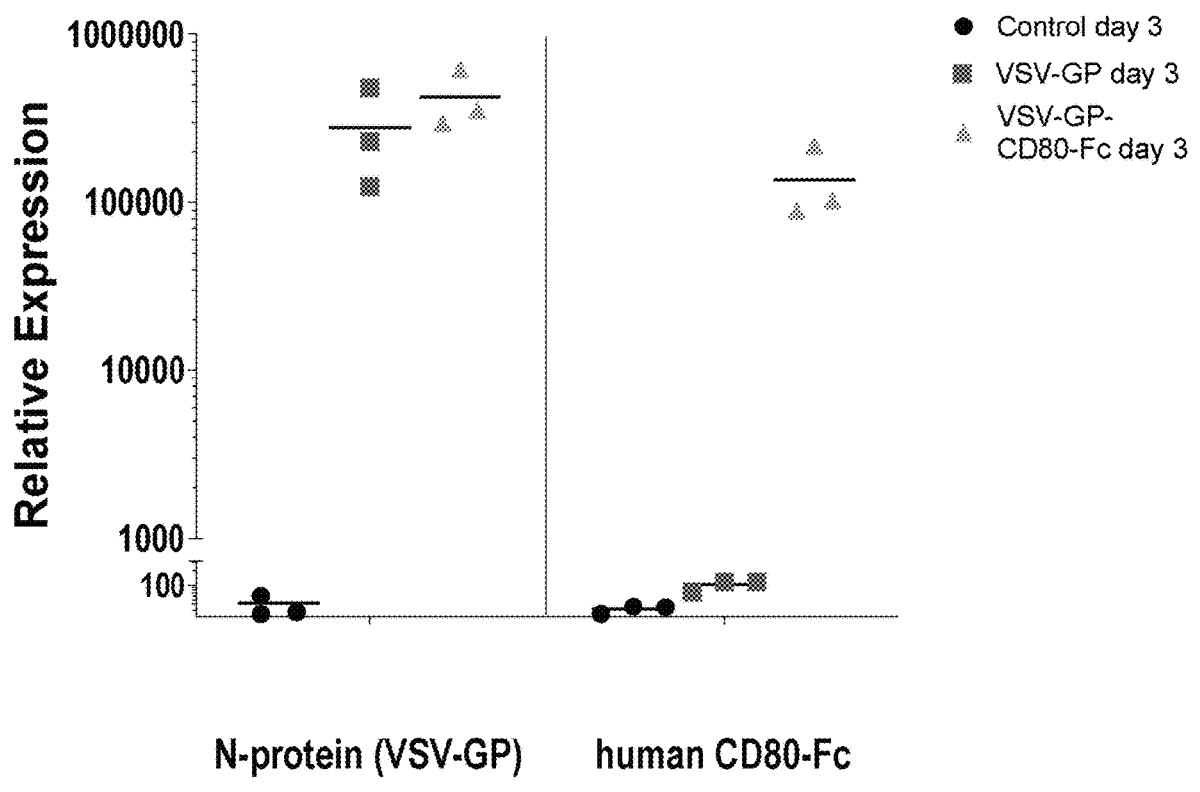
Figure 10:
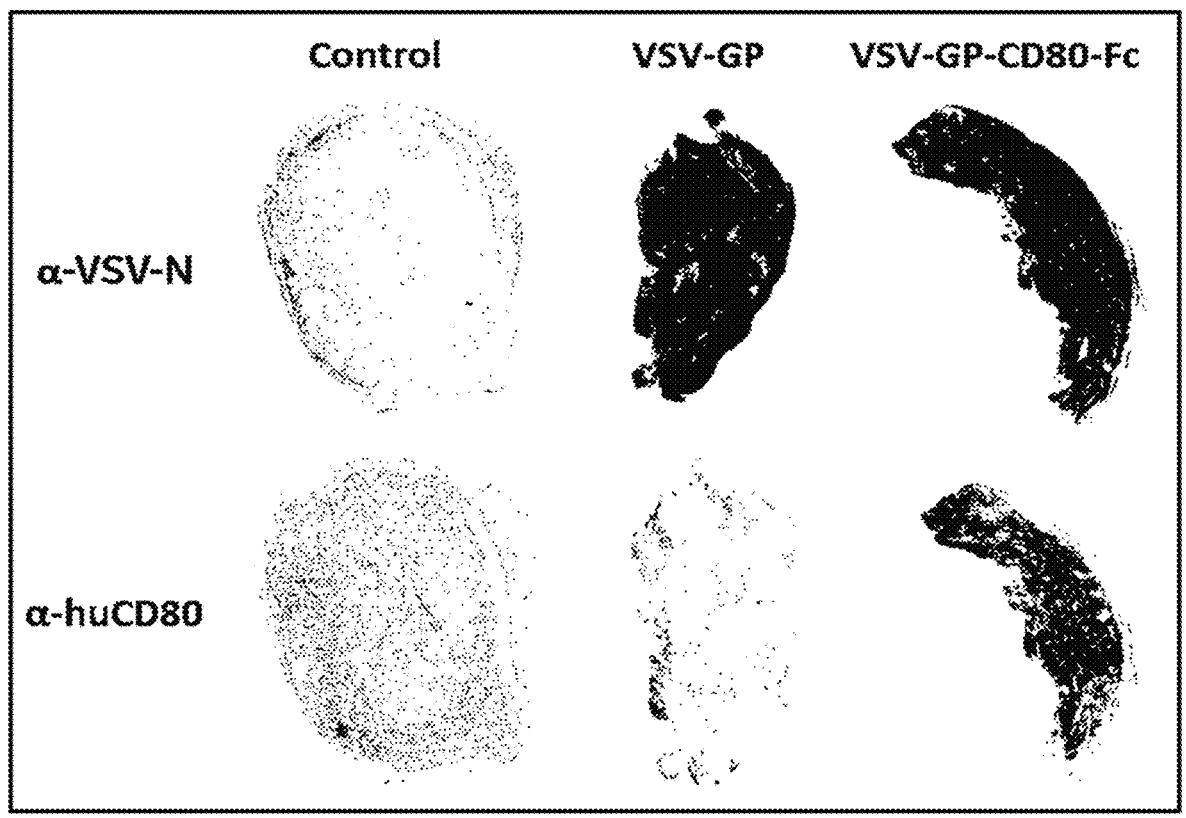
FIG. 10 IHC-based detection of the VSV-GP N-protein as well as CD80-Fc cargo (protein) in control, VSV-GP or VSV-GP-CD80-Fc infected LLC-IFNARKO tumors taken from treated mice. Mice were treated as in FIG. 9 and IHC was performed using standard protocols on day 3 post treatment.
Figure 11:
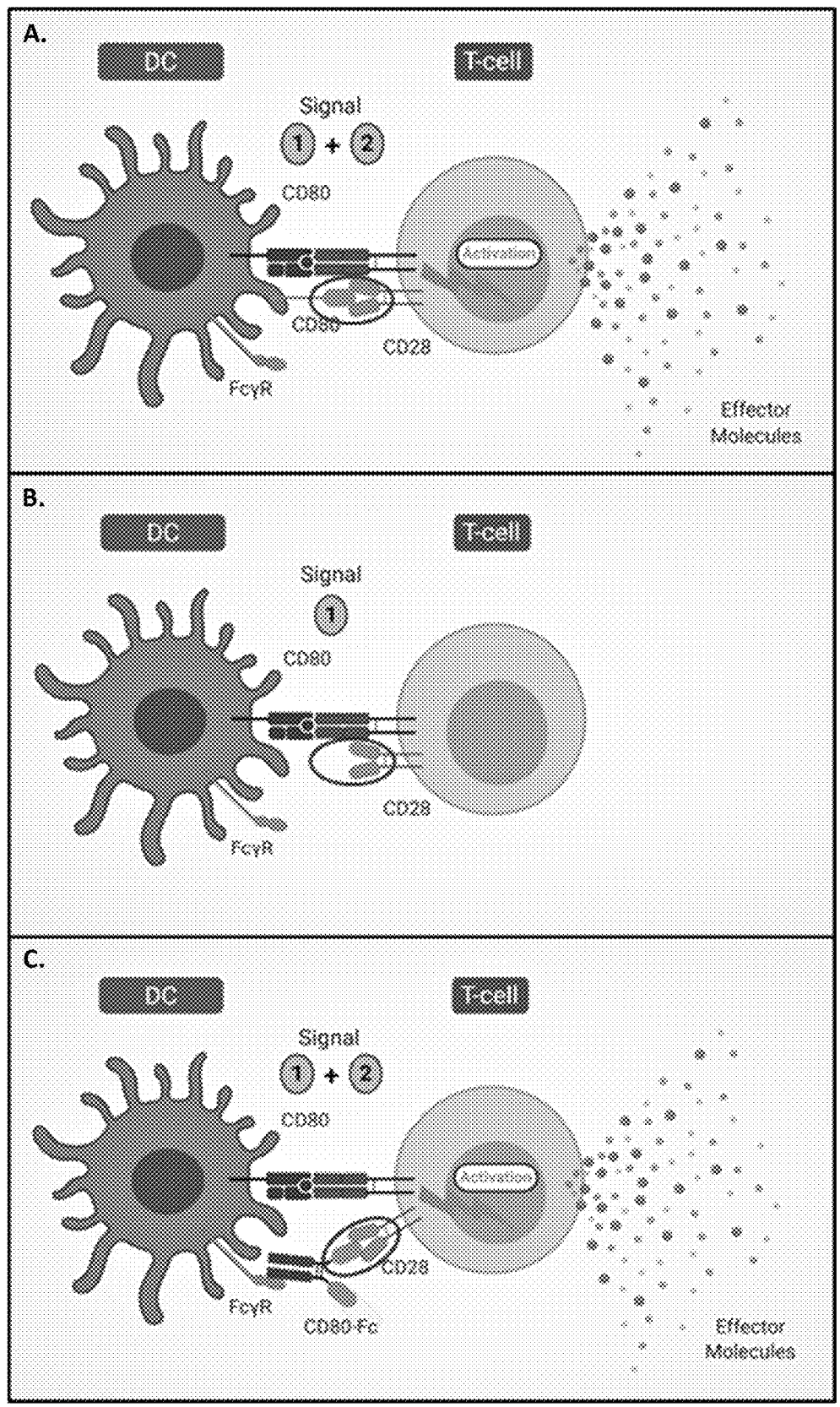
FIG. 11A-C Cartoon depicting CD80-Fc mode of action (MoA) in tumors. Hot tumors (A) with mature, activated DCs, which provide efficient T-cell co-stimulation. Cold tumors (B) lacking DCs and/or dominated by immature, tolerogenic DC subsets. The absence of DCs or immature tolerogenic DC subsets results in poor T-cell immunity, clonal anergy, T-cell dysfunction & cell death. CD80-Fc converting cold tumors into hot tumors (C) by compensating for the lack of potent T-cell co-stimulation.

In Vivo Viral Persistence & Replication as Well as Cargo Expression
FIG. 8-10

Balb/c mice with established CT26.CL25-IFNARKO (CT26.CL25 tumor cells deleted for the interferon alpha receptor) tumors were used as controls or treated with a single i.v. injection of $1 \times 10^8$ TCID$_{50}$ of VSV-GP-CD80-Fc. Three and seven days post treatment tumors were resected; whole RNA was extracted and analyzed using qPCR primers specific for the VSV n gene (FIG. 8). C57BL/6 mice with established LLC1-IFNARKO (LLC1 tumor cells deleted for the interferon alpha receptor) tumors were used as controls or treated with a single i.v. injection of $1 \times 10^8$ TCID$_{50}$ of VSV-GP or VSV-GP-CD80-Fc. Three days post treatment, tumors were resected, and RNA analyzed using the "Pan Cancer Immune Profiling Panel" from NanoString, combined with virus and cargo specific probes (spike-in) according to the manufacturer's instructions (FIG. 9). Taken together the results show active replication of VSV-GP-CD80-Fc in treated animals and mRNA expression of the cargo in the tumor. Peak replication was observed around day three. The virus also persists up to day seven. C57BL/6 mice with established LLC1-IFNARKO tumors were used as controls or treated with a single i.v. injection of $1 \times 10^8$ TCID$_{50}$ of VSV-GP or VSV-GP-CD80-Fc. Three days post treatment, tumors were resected, formalin fixed and paraffin embedded. Thin sections were stained with specific antibodies to the VSV-N protein or the human CD80 protein (FIG. 10). N protein staining was similar for both VSV-GP and VSV-GP-CD80-Fc, while the human CD80 was specifically detected only for the latter.

Example 7

Figure 12:
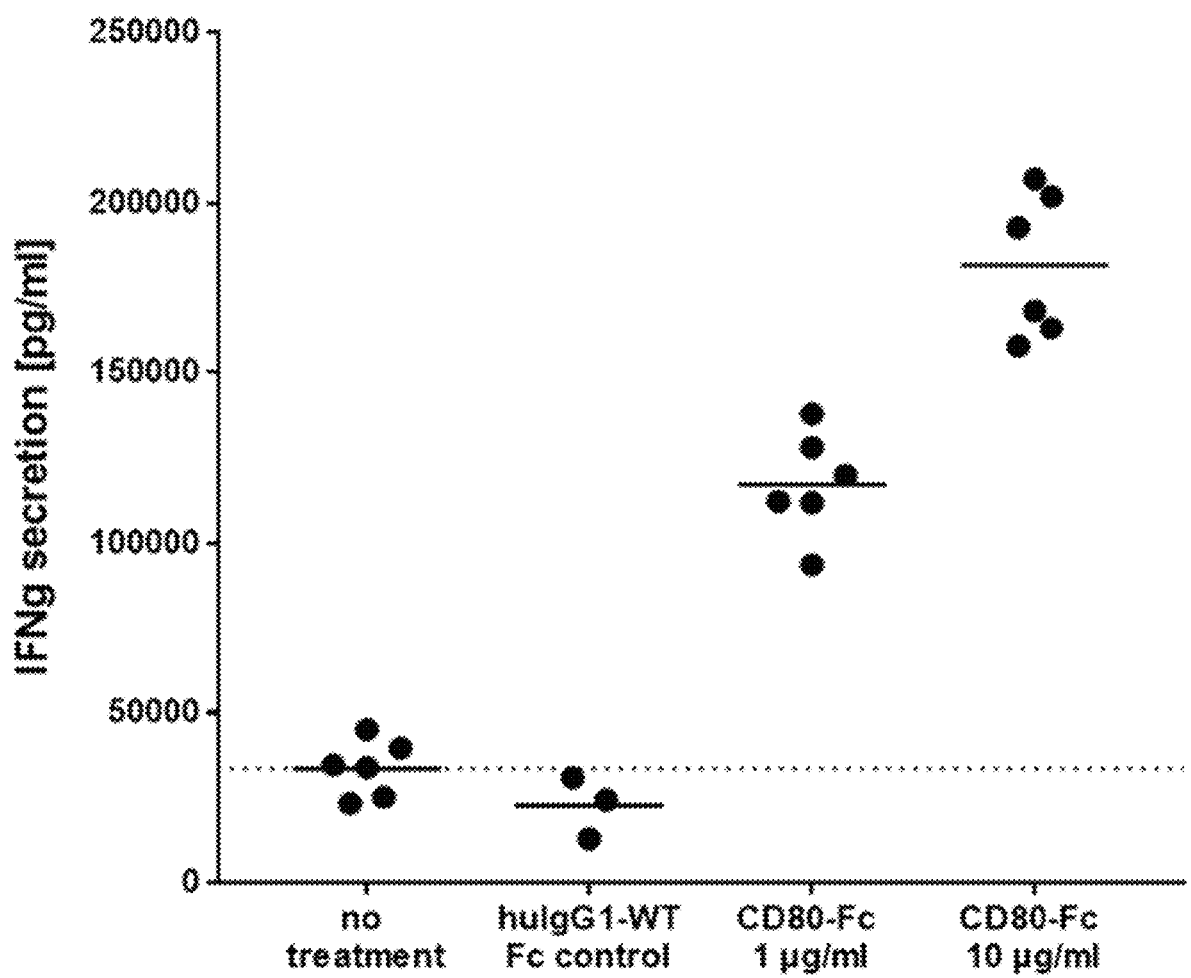
FIG. 12 A human Mixed-Leukocyte culture (T-cells and immature dendritic cells from two genetically different individuals are co-cultured resulting in allogenic T-cell stimulation) was used to evaluate T-cell co-stimulation by recombinant CD80-Fc. To this end cultures were stimulated with increasing amounts of a recombinant CD80-Fc protein using IFNs secretion as readout.
Figure 15:
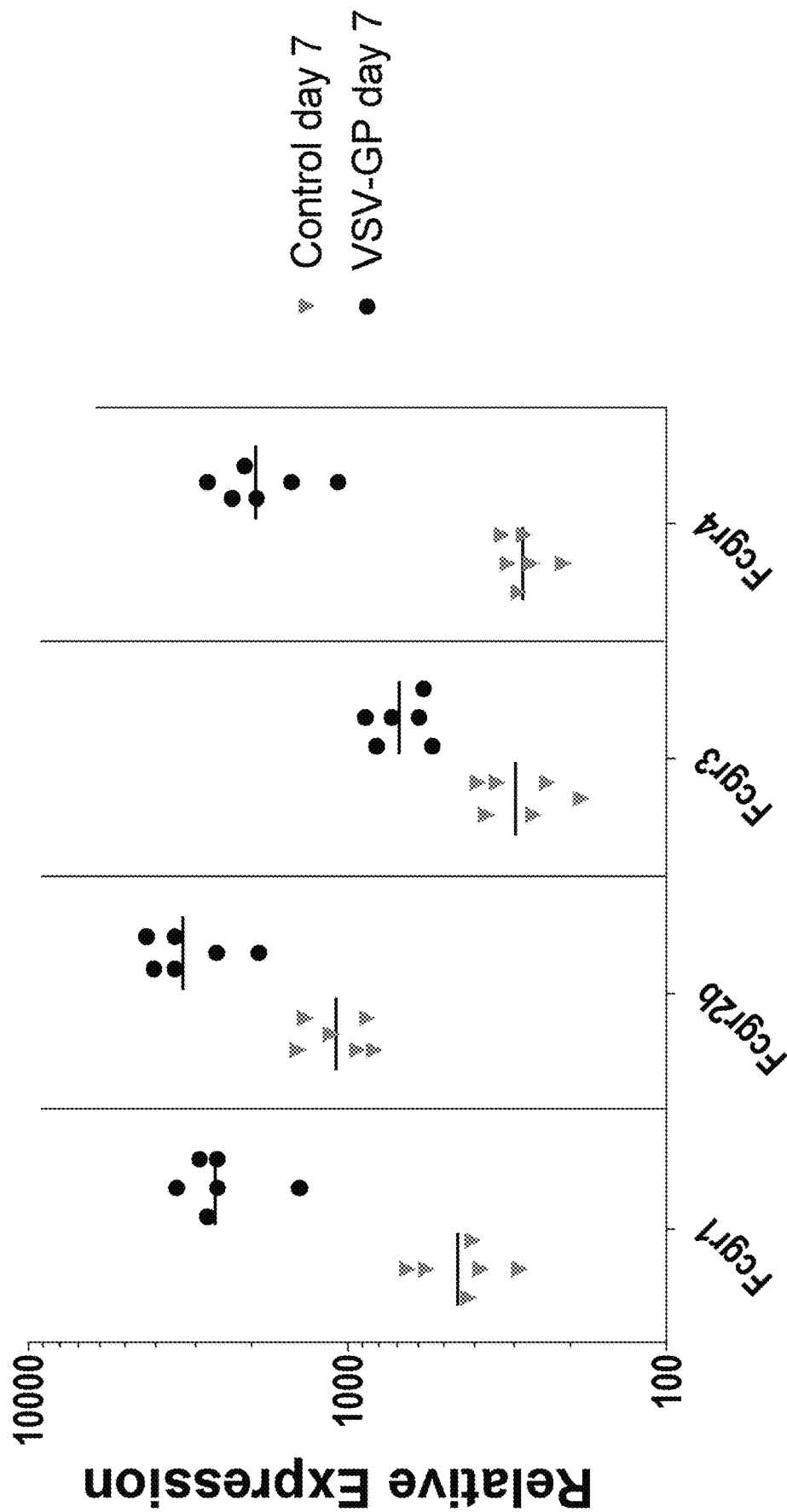
FIG. 15 NanoString-based measurement of FcγRs in control or VSV-GP infected LLC1-IFNARKO tumors at day 7 post infection. Mice were left either untreated or were infected with a viral dose of $10^8$ $TCID_{50}$ VSV-GP. X-axis shows the measurements for the different FcγRs (1, 2b, 3 or 4) and the Y-axis the relative expression after 7 days.
Figure 17:
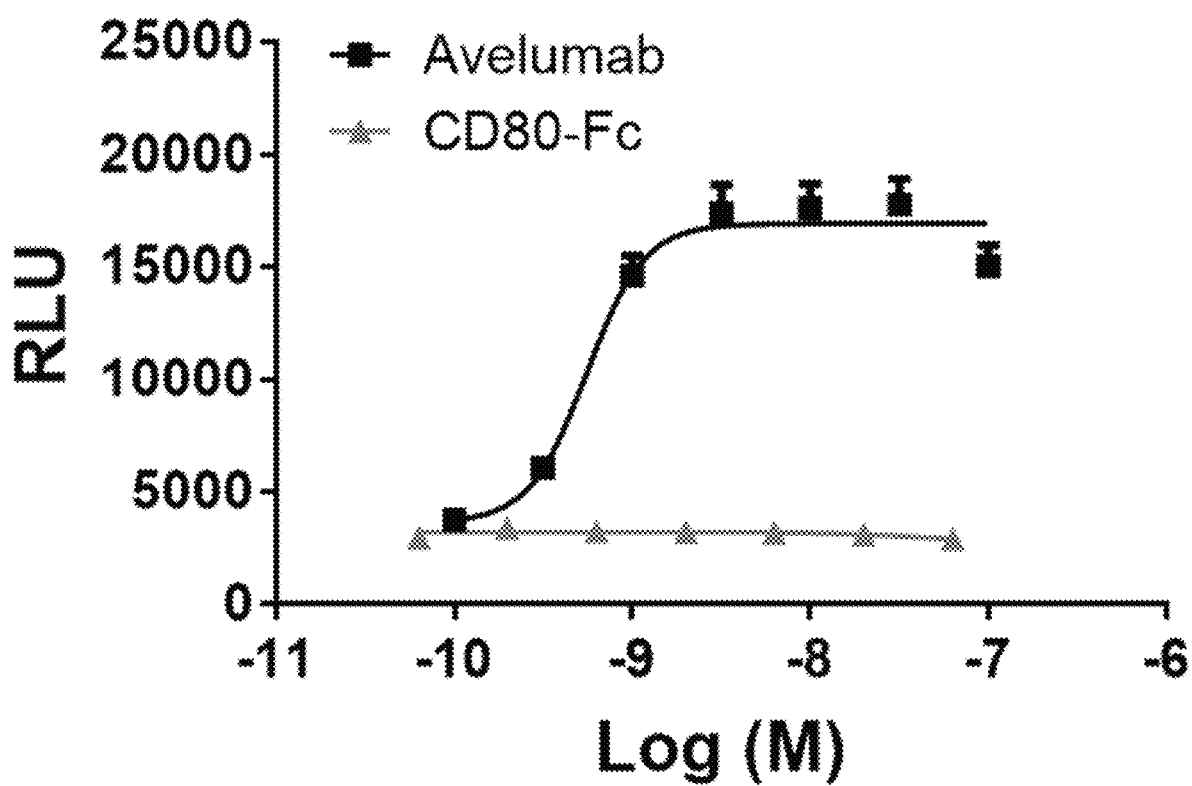
FIG. 17 Luminescence based readout: Co-culture Jurkat PD-1 reporter cells & CHO-K1-α-CD3/-PDL1. CD80-Fc, as opposed to the anti-PDL1 antibody Avelumab, is not able to prevent PD1:PDL1-mediated suppression of the Jurkat reporter cell line.

CD80-Fc Provides T-Cell Co-Stimulation in Human Mixed-Leukocyte Culture. FcγR Blockade Diminishes T-Cell Activation, Essential Role of Fc
FIG. 12 & FIG. 13A-D A human Mixed-Leukocyte culture (selected leukocyte populations from two genetically different individuals are co-cultured resulting in allogenic T-cell stimulation) was used to evaluate the T-cell co-stimulatory potential of recombinant CD80-Fc (FIGS. 12&13) as well as the contribution of the wild type human IgG1 Fc for T-cell co-stimulation (FIG. 13). To this end cultures in FIG. 12 were stimulated with increasing amounts of recombinant CD80-Fc using IFNγ as readout. IFNγ secretion was strongly improved by addition of CD80-Fc to the cultures in a dose-dependent manner validating its T-cell co-stimulatory potential. Building on these data and aiming at elucidating the contribution of the Fc in the CD80-Fc fusion protein human Mixed-Leukocyte cultures were again stimulated with recombinant CD80-Fc protein (10 µg/ml) with or without the addition of FcγR-block (in the absence of human serum), using IFNγ as readout (FIG. 13). The different sub-figures (A-D) depict different donor pairs. CD80-Fc-mediated T-cell stimulation was strongly reduced by the addition of the FcγR-block, indicating that FcγR interaction and FcγR-mediated clustering is crucial for the activity of CD80-Fc.

Example 8

FcγR Dependence of T-Cell Activation by CD80-Fc in CD3 Activated PBMCs (F(ab)2 & IgG4)
FIG. 14A-F Human PBMC cultures were stimulated with or without low doses of anti-CD3 (clone OKT3; 10 ng/ml) and increasing concentrations of recombinant CD80-Fc proteins using IFNγ (FIG. 14A-C) or IL2 (FIG. 14D-F) as readouts, which were detected by standard ELISA. To confirm the T-cell co-stimulatory potential of recombinant CD80-Fc as well as the contribution of the wild type human IgG1 Fc for T-cell co-stimulation and validate Fc-selection the following recombinant CD80-Fc variants were compared back-to-back: CD80-Fc (recombinant version of the viral cargo with wild type human IgG1 Fc, FIG. 14C and F)); CD80 FAB (a F(ab)$_2$ variant of CD80-Fc, which lacks the Fc but retains bivalency, FIG. 14A and D) and CD80 IgG4 (like CD80-Fc but with a human IgG4 Fc, FIG. 14B and E). While CD80-Fc on its own did not significantly stimulate PBMCs the combination of CD80-Fc and the stimulating anti-CD3 antibody resulted in a dose dependent increase in T-cell stimulation as evidenced by IFNγ and IL2 secretion (FIG. 14C and F). On the contrary the Fc-lacking F(ab)$_2$ variant of CD80-Fc was not active and did not result in an improved T-cell stimulation, neither alone, nor in combination with anti-CD3 stimulation (FIG. 14A and D). The IgG4-based CD80 fusion (FIG. 14B and E) displayed T-cell co-stimulatory potential, but to a much lower degree than the IgG1-based CD80 fusion construct (FIG. 14B and F), which resembles the viral cargo engineered into the novel virus VSV-GP-CD80-Fc. These results again confirm the FcγR dependency of CD80-Fc as well as selection of the human IgG1 Fc. Furthermore, the lack of CD80-Fc activity without concomitant TCR stimulation argues for it favorable safety profile.

Example 9

VSV-GP Induces a Local Increase in FcγRs within Infected Tumors Supporting the CD80-Fc MoA

FIG. 15

Given the FcγR-dependency of the viral CD80-Fc cargo for T-cell co-stimulation the impact of VSV-GP infection on FcγR expression was explored in tumors. To this end NanoString-based measurements of FcγR expression in control or VSV-GP infected LLC1-IFNARKO tumors were performed at day 7 post infection. Mice were left either untreated or were infected with a viral dose of $10^8$ TCID$_{50}$ VSV-GP. X-axis shows the measurements for the different FcγRs (1, 2b, 3 or 4) and the Y-axis the relative expression. As the data clearly illustrate VSV-GP infected tumors unexpectedly display a strong upregulation of expression for all four analyzed FcγRs. These data provide a mechanistic basis for the favorable therapeutic interacting of the oncolytic virus VSV-GP and the FcγR-dependent, virally encoded cargo CD80-Fc, which benefits form the virus mediated FcγR upregulation within infected tumors.

Example 10

VSV-GP-CD80-Fc Induces Superior Tumor-Specific T-Cell Immunity as Compared to the Parental Virus VSV-GP

FIG. 16A-C

The impact of the virally encoded CD80-Fc cargo on tumor-antigen specific T-cell immunity was elucidated using the CT26.CL25-IFNARKO tumor model, which was treated with either the parental virus VSV-GP or the new virus VSV-GP-CD80-Fc. Gp70/tumor specific T-cells were detected in spleen and blood of mice treated as depicted in FIG. 16C by ELISPOT (FIG. 16A) and FACS-based Dextramer staining (FIG. 16B) respectively. The significant increase in the frequency of tumor-antigen specific T-cells in the VSV-GP-CD80-Fc group vs. the VSV-GP group illustrates the upside potential of the novel, cargo-armed virus vs. the parental virus and furthermore provides an immunological/mechanistic basis for the improved anti-tumor activity of the novel oncolytic virus VSV-GP-CD80-Fc.

Example 11

CD80-Fc does not Interact with PD-L1

FIG. 17

It has been claimed that CD80 may be able to directly interact with Programmed cell death 1 ligand 1 (PD-L1), thereby blocking the inhibitory interaction of PD-L1 with it's receptor Programmed cell death 1 (PD-1) on activated T-cells. To determine whether the CD80-Fc fusion protein encoded in VSV-GP-CD80-Fc does directly interact with PD-L1 we performed a binding study on CHO-K1 cells stable transfected with human PD-L1. The PD-L1 specific antibody Avelumab was used as a positive control. While Avelumab readily bound to PD-L1 on the surface of the CHO-K1-PD-L1 cells the recombinant CD80-Fc protein failed to bind PD-L1 at all tested dose levels. It was therefore concluded that CD80-Fc does not directly bind to PD-L1.

Example 12

α-PD-1 and CD80-Fc Improve T-Cell Stimulation in an Additive Manner

FIG. 18A-B

To address the question whether CD80-Fc-mediated T-cell co-stimulation combined with antibody-mediated PD-1 inhibition is able to provide an additional benefit vs. the monotherapy treatments we employed a T-cell reporter system, where stably PD-1 expressing Jurkat T-cells do respond to T-cell receptor (TCR) stimulation by upregulating a luciferase activity, which is biochemically detectable. Here Jurkat-PD-1 reporter cells were co-cultured with FcγR positive THP1-PD-L1 cells (as opposed to the FcγR negative CHO-K1 cells), stably expressing PD-L1. The interaction of PD-L1 and PD-1 result in inhibition of Jurkat T-cell activation, comparable to the T-cell inhibition, which is observed in cancer patients. TCR stimulation is achieved by addition of a bi-specific BiTE molecule, which connects CD33 on the THP1 cells with CD3 on the Jurkat T-cells. As can be seen from FIG. 18A the PD-1 blocking antibody Pembrolizumab is able to restore CD3×CD33 BiTE-mediated T-cell stimulation in a dose-dependent manner by blocking the inhibitory PD-1:PD-L1 interaction. At the same time and quiet unexpected CD80-Fc on its own is able to provide T-cell co-stimulation and improve Jurkat T-cell activation in a dose-dependent manner despite the inhibitory PD-1:PD-L1 interaction. A Digitonin (Dig) specific antibody was used as isotype control. In FIG. 18B a fixed anti-PD-1 concentration (10 nM, in saturation) was combined with increasing concentrations of recombinant CD80-Fc. Addition of CD80-Fc on-top of the anti-PD-1 antibody resulted in superior T-cell activation providing clear evidence for the favorable interaction of these different therapeutic modalities, driven by their complementary mode of actions.

Example 13

VSV-GP-muCD80-Fc (In Vivo)—CT26.CL25-IFNARKO Tumor Model (High Cargo Expression)

FIG. 19A-C

Using again the CT26.CL25-IFNARKO tumor model, this study compares the in vivo efficacy of recombinant murine CD80Fc, VSV-GP or VSV-GP-muCD80Fc. For this purpose, mice with established tumors were treated i.v. on day 0 & 3 with a viral dose of $1 \times 10^8$ TCID$_{50}$ and on day 0, 3 and 6 with 1 mg/kg recombinant murine CD80-Fc, respectively.

As depicted in FIG. 19 panel (A) survival curves showed an improved therapeutic outcome in the VSV-GP-muCD80Fc treated groups. A significant survival benefit above recombinant CD80Fc protein or VSV-GP could be shown by $1 \times 10^8$ TCID$_{50}$ VSV-GP-muCD80Fc (Log-rank (Mantel-Cox) test; P value 0.0394).

The mean tumor sizes depicted in FIG. 19 panel (B) summarize single tumor growth curves and reflect a potent tumor-growth suppression after treatment with VSV-GP-muCD80Fc (dose $1 \times 10^8$ TCID$_{50}$) which outperformed VSV-GP as well as 1 mg/kg of recombinant CD80Fc protein by a far margin.

A drop in body weight was observed after first injection of both viruses (FIG. 19 panel (C)), however, recovery took place immediately, was not affected by the following injection of substances and did not significantly differ between the parental virus (VSV-GP) and the muCD80-Fc encoding virus (VSV-GP-muCD80Fc).

In summary, this study compared in particular the in vivo effects of recombinant murine CD80Fc or VSV-GP with VSV-GP-muCD80Fc. It was shown that by implementing muCD80Fc in the virus backbone a synergistic effect on tumor growth as well as overall survival was achieved.

The invention claimed is:

1. A recombinant vesicular stomatitis virus encoding in its genome at least one CD80 extracellular domain Fc-fusion protein, wherein the CD80 extracellular domain Fc-fusion protein comprises the extracellular domain of CD80 and further comprises the Fc domain of an IgG wherein the CD80 extracellular domain Fc-fusion protein comprises SEQ ID NO: 4; and the gene coding for the wild-type glycoprotein G of the recombinant vesicular stomatitis virus is replaced by the gene coding for the glycoprotein G (GP) of Lymphocyte choriomeningitis virus (LCMV), and/or the wild-type glycoprotein G is replaced by the glycoprotein G (GP) of LCMV.

2. The recombinant vesicular stomatitis virus according to claim 1, wherein the vesicular stomatitis virus is replication-competent.

3. The recombinant vesicular stomatitis virus according to claim 1, wherein said CD80 extracellular domain Fc-fusion protein further comprises a signal peptide sequence operably linked to said CD80 extracellular domain Fc-fusion protein.

4. The recombinant vesicular stomatitis virus according to claim 3, wherein said CD80 extracellular domain Fc-fusion protein consists of SEQ ID NO:3.

5. The recombinant vesicular stomatitis virus according to claim 1, encoding a vesicular stomatitis virus nucleoprotein (N) wherein the nucleoprotein (N) comprises an amino acid sequence as set forth in SEQ ID NO:7 or a functional variant at least 98% identical to SEQ ID NO:7.

6. The recombinant vesicular stomatitis virus according to claim 1, encoding a vesicular stomatitis virus phosphoprotein (P) wherein the phosphoprotein (P) comprises an amino acid sequence as set forth in SEQ ID NO:8 or a functional variant at least 98% identical to SEQ ID NO:8.

7. The recombinant vesicular stomatitis virus according to claim 1, encoding a vesicular stomatitis virus large protein (L) wherein the large protein (L) comprises an amino acid sequence as set forth in SEQ ID NO:9 or a functional variant at least 98% identical to SEQ ID NO:9.

8. The recombinant vesicular stomatitis virus according to claim 1, encoding a vesicular stomatitis virus matrix protein (M) wherein the matrix protein (M) comprises an amino acid sequence as set forth in SEQ ID NO:10 or a functional variant at least 98% identical to SEQ ID NO:10.

9. The recombinant vesicular stomatitis virus according to claim 1, encoding:
the vesicular stomatitis virus nucleoprotein (N) comprising an amino acid sequence as set forth in SEQ ID NO:7 or a functional variant at least 98% identical to SEQ ID NO:7,
the phosphoprotein (P) comprising an amino acid sequence as set forth in SEQ ID NO:8 or a functional variant at least 98% identical to SEQ ID NO:8,
the large protein (L) comprising an amino acid sequence as set forth in SEQ ID NO: 9 or a functional variant at least 98% identical to SEQ ID NO:9, and
the matrix protein (M) comprising an amino acid sequence as set forth in SEQ ID NO:10 or a functional variant at 98% identical to SEQ ID NO:10.

10. The recombinant vesicular stomatitis virus according to claim 9, which is replication-competent.

11. A pharmaceutical composition, characterized in that the composition comprises a recombinant vesicular stomatitis virus according to claim 1.

12. A recombinant vesicular stomatitis virus encoding in its genome a vesicular stomatitis virus nucleoprotein (N), large protein (L), phosphoprotein (P), matrix protein (M), glycoprotein (G) and at least one CD80 extracellular domain Fc-fusion protein, wherein the CD80 extracellular domain Fc-fusion protein comprises
a CD80 extracellular domain Fc-fusion protein, comprising SEQ ID NO:4, wherein, the gene coding for the wild-type glycoprotein G of the vesicular stomatitis virus is replaced by the gene coding for the glycoprotein G (GP) of lymphocyte choriomeningitis virus (LCMV), and/or the wild-type glycoprotein G is replaced by the glycoprotein G (GP) of LCMV, and wherein
the nucleoprotein (N) comprising an amino acid as set forth in SEQ ID NO:7 or a functional variant at least 98% identical to SEQ ID NO:7,
the phosphoprotein (P) comprising an amino acid as set forth in SEQ ID NO: 8 or a functional variant at least 98% identical to SEQ ID NO:8,
the large protein (L) comprising an amino acid as set forth in SEQ ID NO:9 or a functional variant at least 98% o identical to SEQ ID NO:9, and
the matrix protein (M) comprising an amino acid as set forth in SEQ ID NO: 10 or a functional variant at least 98% identical to SEQ ID NO:10.

13. The recombinant vesicular stomatitis virus of claim 12, wherein the CD80 extracellular domain Fc-fusion protein further comprises a signal peptide sequence operably linked to said CD80 extracellular domain Fc-fusion protein.

14. The recombinant vesicular stomatitis virus according to claim 13, wherein said CD80 extracellular domain Fc-fusion protein consists of SEQ ID NO:3.

15. A recombinant rhabdovirus encoding in its RNA genome at least one CD80 extracellular domain Fc-fusion protein or a functional variant thereof, wherein the CD80 extracellular domain Fc-fusion protein comprises the extracellular domain of CD80 and further comprises the Fc domain of an IgG, wherein the RNA genome of the recombinant rhabdovirus comprises or consists of a coding sequence identical or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24.

* * * * *

SEQUENCE LISTING

<160> NUMBER OF SEQ ID NOS: 24

<210> SEQ ID NO 1
<211> LENGTH: 208
<212> TYPE: PRT
<213> ORGANISM: Homo sapiens

<400> SEQUENCE: 1

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 2
<211> LENGTH: 232
<212> TYPE: PRT
<213> ORGANISM: Homo sapiens

<400> SEQUENCE: 2

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
```

```
            115                 120                 125
Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 3
<211> LENGTH: 467
<212> TYPE: PRT
<213> ORGANISM: Homo sapiens

<400> SEQUENCE: 3

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asp Lys Thr His Thr Cys Pro Pro Cys Pro Ala Pro Glu Leu Leu
                245                 250                 255
```

```
Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                    325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                    405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly
465

<210> SEQ ID NO 4
<211> LENGTH: 433
<212> TYPE: PRT
<213> ORGANISM: Homo sapiens

<400> SEQUENCE: 4

Val Ile His Val Thr Lys Glu Val Lys Glu Val Ala Thr Leu Ser Cys
1                   5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                    85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160
```

```
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
            180                 185                 190
Gln Thr Phe Asn Trp Asn Thr Thr Lys Gln Glu His Phe Pro Asp Asp
        195                 200                 205
Lys Thr His Thr Cys Pro Pro Cys Pro Ala Pro Glu Leu Leu Gly Gly
    210                 215                 220
Pro Ser Val Phe Leu Phe Pro Pro Lys Pro Lys Asp Thr Leu Met Ile
225                 230                 235                 240
Ser Arg Thr Pro Glu Val Thr Cys Val Val Asp Val Ser His Glu
                245                 250                 255
Asp Pro Glu Val Lys Phe Asn Trp Tyr Val Asp Gly Val Glu Val His
            260                 265                 270
Asn Ala Lys Thr Lys Pro Arg Glu Glu Gln Tyr Asn Ser Thr Tyr Arg
        275                 280                 285
Val Val Ser Val Leu Thr Val Leu His Gln Asp Trp Leu Asn Gly Lys
    290                 295                 300
Glu Tyr Lys Cys Lys Val Ser Asn Lys Ala Leu Pro Ala Pro Ile Glu
305                 310                 315                 320
Lys Thr Ile Ser Lys Ala Lys Gly Gln Pro Arg Glu Pro Gln Val Tyr
                325                 330                 335
Thr Leu Pro Pro Ser Arg Glu Glu Met Thr Lys Asn Gln Val Ser Leu
            340                 345                 350
Thr Cys Leu Val Lys Gly Phe Tyr Pro Ser Asp Ile Ala Val Glu Trp
        355                 360                 365
Glu Ser Asn Gly Gln Pro Glu Asn Asn Tyr Lys Thr Thr Pro Pro Val
    370                 375                 380
Leu Asp Ser Asp Gly Ser Phe Phe Leu Tyr Ser Lys Leu Thr Val Asp
385                 390                 395                 400
Lys Ser Arg Trp Gln Gln Gly Asn Val Phe Ser Cys Ser Val Met His
                405                 410                 415
Glu Ala Leu His Asn His Tyr Thr Gln Lys Ser Leu Ser Leu Ser Pro
            420                 425                 430
Gly

<210> SEQ ID NO 5
<211> LENGTH: 19
<212> TYPE: PRT
<213> ORGANISM: Mus musculus

<400> SEQUENCE: 5

Met Gly Trp Ser Cys Ile Ile Leu Phe Leu Val Ala Thr Ala Thr Gly
1               5                   10                  15

Val His Ser

<210> SEQ ID NO 6
<211> LENGTH: 288
<212> TYPE: PRT
<213> ORGANISM: Homo sapiens

<400> SEQUENCE: 6

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
```

```
            20                  25                  30
Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
            50                  55                  60

Tyr Trp Gln Lys Glu Lys Met Val Leu Thr Met Met Ser Gly Asp
65                  70                  75                  80

Met Asn Ile Trp Pro Glu Tyr Lys Asn Arg Thr Ile Phe Asp Ile Thr
                    85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
                115                 120                 125

Glu His Leu Ala Glu Val Thr Leu Ser Val Lys Ala Asp Phe Pro Thr
            130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                    165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
            210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                    245                 250                 255

Ile Phe Val Ile Cys Cys Leu Thr Tyr Cys Phe Ala Pro Arg Cys Arg
                    260                 265                 270

Glu Arg Arg Arg Asn Glu Arg Leu Arg Arg Glu Ser Val Arg Pro Val
            275                 280                 285

<210> SEQ ID NO 7
<211> LENGTH: 422
<212> TYPE: PRT
<213> ORGANISM: Vesicular stomatitis virus

<400> SEQUENCE: 7

Met Ser Val Thr Val Lys Arg Ile Ile Asp Asn Thr Val Val Val Pro
1               5                   10                  15

Lys Leu Pro Ala Asn Glu Asp Pro Val Glu Tyr Pro Ala Asp Tyr Phe
            20                  25                  30

Arg Lys Ser Lys Glu Ile Pro Leu Tyr Ile Asn Thr Thr Lys Ser Leu
            35                  40                  45

Ser Asp Leu Arg Gly Tyr Val Tyr Gln Gly Leu Lys Ser Gly Asn Val
        50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                    85                  90                  95

Lys Ala Gly Asp Thr Ile Gly Ile Phe Asp Leu Val Ser Leu Lys Ala
                100                 105                 110
```

```
Leu Asp Gly Val Leu Pro Asp Gly Val Ser Asp Ala Ser Arg Thr Ser
            115                 120                 125

Ala Asp Asp Lys Trp Leu Pro Leu Tyr Leu Leu Gly Leu Tyr Arg Val
130                 135                 140

Gly Arg Thr Gln Met Pro Glu Tyr Arg Lys Lys Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
        195                 200                 205

Glu Cys Ala Ser Phe Arg Tyr Gly Thr Ile Val Ser Arg Phe Lys Asp
    210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
                245                 250                 255

Glu Met Val Gln Met Met Leu Pro Gly Gln Glu Ile Asp Lys Ala Asp
            260                 265                 270

Ser Tyr Met Pro Tyr Leu Ile Asp Phe Gly Leu Ser Ser Lys Ser Pro
        275                 280                 285

Tyr Ser Ser Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Cys Val Gly Asp
            340                 345                 350

Asn Lys Tyr Thr Pro Asp Asp Ser Thr Gly Gly Leu Thr Thr Asn Ala
        355                 360                 365

Pro Pro Gln Gly Arg Asp Val Val Glu Trp Leu Gly Trp Phe Glu Asp
370                 375                 380

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
                405                 410                 415

Lys Ser Glu Phe Asp Lys
            420

<210> SEQ ID NO 8
<211> LENGTH: 265
<212> TYPE: PRT
<213> ORGANISM: Vesicular stomatitis virus

<400> SEQUENCE: 8

Met Asp Asn Leu Thr Lys Val Arg Glu Tyr Leu Lys Ser Tyr Ser Arg
1               5                   10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Lys Pro Ser Tyr Phe Gln Ala Ala Asp Asp Ser Asp Thr Glu Ser
    50                  55                  60
```

```
Glu Pro Glu Ile Glu Asp Asn Gln Gly Leu Tyr Ala Pro Asp Pro Glu
 65                  70                  75                  80

Ala Glu Gln Val Glu Gly Phe Ile Gln Gly Pro Leu Asp Asp Tyr Ala
             85                  90                  95

Asp Glu Glu Val Asp Val Val Phe Thr Ser Asp Trp Lys Gln Pro Glu
            100                 105                 110

Leu Glu Ser Asp Glu His Gly Lys Thr Leu Arg Leu Thr Ser Pro Glu
            115                 120                 125

Gly Leu Ser Gly Glu Gln Lys Ser Gln Trp Leu Ser Thr Ile Lys Ala
130                 135                 140

Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
            195                 200                 205

Pro Lys Lys Ala Ser Leu Gln Pro Leu Thr Ile Ser Leu Asp Glu Leu
            210                 215                 220

Phe Ser Ser Arg Gly Glu Phe Ile Ser Val Gly Gly Asp Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265

<210> SEQ ID NO 9
<211> LENGTH: 2109
<212> TYPE: PRT
<213> ORGANISM: Vesicular stomatitis virus

<400> SEQUENCE: 9

Met Glu Val His Asp Phe Glu Thr Asp Glu Phe Asn Asp Phe Asn Glu
 1               5                  10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
         35                  40                  45

Asp Ile Asp Asn Leu Ile Arg Lys Phe Asn Ser Leu Pro Ile Pro Ser
 50                  55                  60

Met Trp Asp Ser Lys Asn Trp Asp Gly Val Leu Glu Met Leu Thr Ser
 65                  70                  75                  80

Cys Gln Ala Asn Pro Ile Pro Thr Ser Gln Met His Lys Trp Met Gly
             85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
            115                 120                 125

Thr Phe Ile Arg Gly Trp Gly Asn Lys Pro Ile Glu Tyr Ile Lys Lys
130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
```

-continued

```
                165                 170                 175
Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
    290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
                325                 330                 335

Asp Gln Ile Met Ser Val Lys Thr Val Asp Leu Thr Leu Val Ile Tyr
            340                 345                 350

Gly Ser Phe Arg His Trp Gly His Pro Phe Ile Asp Tyr Tyr Thr Gly
        355                 360                 365

Leu Glu Lys Leu His Ser Gln Val Thr Met Lys Lys Asp Ile Asp Val
    370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
                405                 410                 415

Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
        435                 440                 445

Leu Ile Lys Cys Phe Glu Ile Pro Asp Leu Leu Asp Pro Ser Ile Ile
    450                 455                 460

Tyr Ser Asp Lys Ser His Ser Met Asn Arg Ser Glu Val Leu Lys His
465                 470                 475                 480

Val Arg Met Asn Pro Asn Thr Pro Ile Pro Ser Lys Lys Val Leu Gln
                485                 490                 495

Thr Met Leu Asp Thr Lys Ala Thr Asn Trp Lys Glu Phe Leu Lys Glu
            500                 505                 510

Ile Asp Glu Lys Gly Leu Asp Asp Asp Leu Ile Ile Gly Leu Lys
        515                 520                 525

Gly Lys Glu Arg Glu Leu Lys Leu Ala Gly Arg Phe Phe Ser Leu Met
    530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
                565                 570                 575

Thr Ala Val Ile Lys Lys Met Leu Asp Ser Ser Ser Gly Gln Gly Leu
            580                 585                 590
```

-continued

```
Lys Ser Tyr Glu Ala Ile Cys Ile Ala Asn His Ile Asp Tyr Glu Lys
    595                 600                 605

Trp Asn Asn His Gln Arg Lys Leu Ser Asn Gly Pro Val Phe Arg Val
    610                 615                 620

Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
                660                 665                 670

Trp Gln Gly Gln Glu Gly Gly Leu Glu Gly Leu Arg Gln Lys Gly Trp
                675                 680                 685

Ser Ile Leu Asn Leu Leu Val Ile Gln Arg Glu Ala Lys Ile Arg Asn
    690                 695                 700

Thr Ala Val Lys Val Leu Ala Gln Gly Asp Asn Gln Val Ile Cys Thr
705                 710                 715                 720

Gln Tyr Lys Thr Lys Ser Arg Asn Val Val Glu Leu Gln Gly Ala
                725                 730                 735

Leu Asn Gln Met Val Ser Asn Asn Glu Lys Ile Met Thr Ala Ile Lys
                740                 745                 750

Ile Gly Thr Gly Lys Leu Gly Leu Leu Ile Asn Asp Asp Glu Thr Met
    755                 760                 765

Gln Ser Ala Asp Tyr Leu Asn Tyr Gly Lys Ile Pro Ile Phe Arg Gly
    770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
                820                 825                 830

Met Ile Gln Tyr Asn Tyr Phe Gly Thr Phe Ala Arg Leu Leu Leu Met
    835                 840                 845

Met His Asp Pro Ala Leu Arg Gln Ser Leu Tyr Glu Val Gln Asp Lys
    850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
                900                 905                 910

Phe Ile His Val His Ala Arg Ser Glu His Leu Lys Glu Met Ser Ala
    915                 920                 925

Val Phe Gly Asn Pro Glu Ile Ala Lys Phe Arg Ile Thr His Ile Asp
    930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
                980                 985                 990

Tyr His Glu Glu Asp Arg Leu Arg Ser Phe Leu Trp Ser Ile Asn Pro
    995                 1000                1005
```

-continued

| | | | | | | | | | | | |
|---|---|---|---|---|---|---|---|---|---|---|---|
|Leu|Phe|Pro|Arg|Phe|Leu|Ser|Glu|Phe|Lys|Ser|Gly|Thr|Phe|Leu|
|   |   |   |   |1010|   |   |1015|   |   |1020|   |

Gly Val Ala Asp Gly Leu Ile Ser Leu Phe Gln Asn Ser Arg Thr
    1025              1030              1035

Ile Arg Asn Ser Phe Lys Lys Lys Tyr His Arg Glu Leu Asp Asp
    1040              1045              1050

Leu Ile Val Arg Ser Glu Val Ser Ser Leu Thr His Leu Gly Lys
    1055              1060              1065

Leu His Leu Arg Arg Gly Ser Cys Lys Met Trp Thr Cys Ser Ala
    1070              1075              1080

Thr His Ala Asp Thr Leu Arg Tyr Lys Ser Trp Gly Arg Thr Val
    1085              1090              1095

Ile Gly Thr Thr Val Pro His Pro Leu Glu Met Leu Gly Pro Gln
    1100              1105              1110

His Arg Lys Glu Thr Pro Cys Ala Pro Cys Asn Thr Ser Gly Phe
    1115              1120              1125

Asn Tyr Val Ser Val His Cys Pro Asp Gly Ile His Asp Val Phe
    1130              1135              1140

Ser Ser Arg Gly Pro Leu Pro Ala Tyr Leu Gly Ser Lys Thr Ser
    1145              1150              1155

Glu Ser Thr Ser Ile Leu Gln Pro Trp Glu Arg Glu Ser Lys Val
    1160              1165              1170

Pro Leu Ile Lys Arg Ala Thr Arg Leu Arg Asp Ala Ile Ser Trp
    1175              1180              1185

Phe Val Glu Pro Asp Ser Lys Leu Ala Met Thr Ile Leu Ser Asn
    1190              1195              1200

Ile His Ser Leu Thr Gly Glu Glu Trp Thr Lys Arg Gln His Gly
    1205              1210              1215

Phe Lys Arg Thr Gly Ser Ala Leu His Arg Phe Ser Thr Ser Arg
    1220              1225              1230

Met Ser His Gly Gly Phe Ala Ser Gln Ser Thr Ala Ala Leu Thr
    1235              1240              1245

Arg Leu Met Ala Thr Thr Asp Thr Met Arg Asp Leu Gly Asp Gln
    1250              1255              1260

Asn Phe Asp Phe Leu Phe Gln Ala Thr Leu Leu Tyr Ala Gln Ile
    1265              1270              1275

Thr Thr Thr Val Ala Arg Asp Gly Trp Ile Thr Ser Cys Thr Asp
    1280              1285              1290

His Tyr His Ile Ala Cys Lys Ser Cys Leu Arg Pro Ile Glu Glu
    1295              1300              1305

Ile Thr Leu Asp Ser Ser Met Asp Tyr Thr Pro Pro Asp Val Ser
    1310              1315              1320

His Val Leu Lys Thr Trp Arg Asn Gly Glu Gly Ser Trp Gly Gln
    1325              1330              1335

Glu Ile Lys Gln Ile Tyr Pro Leu Glu Gly Asn Trp Lys Asn Leu
    1340              1345              1350

Ala Pro Ala Glu Gln Ser Tyr Gln Val Gly Arg Cys Ile Gly Phe
    1355              1360              1365

Leu Tyr Gly Asp Leu Ala Tyr Arg Lys Ser Thr His Ala Glu Asp
    1370              1375              1380

Ser Ser Leu Phe Pro Leu Ser Ile Gln Gly Arg Ile Arg Gly Arg
    1385              1390              1395

Gly Phe Leu Lys Gly Leu Leu Asp Gly Leu Met Arg Ala Ser Cys

-continued

```
                1400                1405                1410

Cys Gln Val Ile His Arg Arg Ser Leu Ala His Leu Lys Arg Pro
    1415                1420                1425

Ala Asn Ala Val Tyr Gly Gly Leu Ile Tyr Leu Ile Asp Lys Leu
    1430                1435                1440

Ser Val Ser Pro Pro Phe Leu Ser Leu Thr Arg Ser Gly Pro Ile
    1445                1450                1455

Arg Asp Glu Leu Glu Thr Ile Pro His Lys Ile Pro Thr Ser Tyr
    1460                1465                1470

Pro Thr Ser Asn Arg Asp Met Gly Val Ile Val Arg Asn Tyr Phe
    1475                1480                1485

Lys Tyr Gln Cys Arg Leu Ile Glu Lys Gly Lys Tyr Arg Ser His
    1490                1495                1500

Tyr Ser Gln Leu Trp Leu Phe Ser Asp Val Leu Ser Ile Asp Phe
    1505                1510                1515

Ile Gly Pro Phe Ser Ile Ser Thr Thr Leu Leu Gln Ile Leu Tyr
    1520                1525                1530

Lys Pro Phe Leu Ser Gly Lys Asp Lys Asn Glu Leu Arg Glu Leu
    1535                1540                1545

Ala Asn Leu Ser Ser Leu Leu Arg Ser Gly Glu Gly Trp Glu Asp
    1550                1555                1560

Ile His Val Lys Phe Phe Thr Lys Asp Ile Leu Leu Cys Pro Glu
    1565                1570                1575

Glu Ile Arg His Ala Cys Lys Phe Gly Ile Ala Lys Asp Asn Asn
    1580                1585                1590

Lys Asp Met Ser Tyr Pro Pro Trp Gly Arg Glu Ser Arg Gly Thr
    1595                1600                1605

Ile Thr Thr Ile Pro Val Tyr Tyr Thr Thr Pro Tyr Pro Lys
    1610                1615                1620

Met Leu Glu Met Pro Pro Arg Ile Gln Asn Pro Leu Leu Ser Gly
    1625                1630                1635

Ile Arg Leu Gly Gln Leu Pro Thr Gly Ala His Tyr Lys Ile Arg
    1640                1645                1650

Ser Ile Leu His Gly Met Gly Ile His Tyr Arg Asp Phe Leu Ser
    1655                1660                1665

Cys Gly Asp Gly Ser Gly Gly Met Thr Ala Ala Leu Leu Arg Glu
    1670                1675                1680

Asn Val His Ser Arg Gly Ile Phe Asn Ser Leu Leu Glu Leu Ser
    1685                1690                1695

Gly Ser Val Met Arg Gly Ala Ser Pro Glu Pro Pro Ser Ala Leu
    1700                1705                1710

Glu Thr Leu Gly Gly Asp Lys Ser Arg Cys Val Asn Gly Glu Thr
    1715                1720                1725

Cys Trp Glu Tyr Pro Ser Asp Leu Cys Asp Pro Arg Thr Trp Asp
    1730                1735                1740

Tyr Phe Leu Arg Leu Lys Ala Gly Leu Gly Leu Gln Ile Asp Leu
    1745                1750                1755

Ile Val Met Asp Met Glu Val Arg Asp Ser Ser Thr Ser Leu Lys
    1760                1765                1770

Ile Glu Thr Asn Val Arg Asn Tyr Val His Arg Ile Leu Asp Glu
    1775                1780                1785

Gln Gly Val Leu Ile Tyr Lys Thr Tyr Gly Thr Tyr Ile Cys Glu
    1790                1795                1800
```

```
Ser Glu Lys Asn Ala Val Thr Ile Leu Gly Pro Met Phe Lys Thr
1805                1810                1815

Val Asp Leu Val Gln Thr Glu Phe Ser Ser Ser Gln Thr Ser Glu
1820                1825                1830

Val Tyr Met Val Cys Lys Gly Leu Lys Lys Leu Ile Asp Glu Pro
1835                1840                1845

Asn Pro Asp Trp Ser Ser Ile Asn Glu Ser Trp Lys Asn Leu Tyr
1850                1855                1860

Ala Phe Gln Ser Ser Glu Gln Glu Phe Ala Arg Ala Lys Lys Val
1865                1870                1875

Ser Thr Tyr Phe Thr Leu Thr Gly Ile Pro Ser Gln Phe Ile Pro
1880                1885                1890

Asp Pro Phe Val Asn Ile Glu Thr Met Leu Gln Ile Phe Gly Val
1895                1900                1905

Pro Thr Gly Val Ser His Ala Ala Leu Lys Ser Ser Asp Arg
1910                1915                1920

Pro Ala Asp Leu Leu Thr Ile Ser Leu Phe Tyr Met Ala Ile Ile
1925                1930                1935

Ser Tyr Tyr Asn Ile Asn His Ile Arg Val Gly Pro Ile Pro Pro
1940                1945                1950

Asn Pro Pro Ser Asp Gly Ile Ala Gln Asn Val Gly Ile Ala Ile
1955                1960                1965

Thr Gly Ile Ser Phe Trp Leu Ser Leu Met Glu Lys Asp Ile Pro
1970                1975                1980

Leu Tyr Gln Gln Cys Leu Ala Val Ile Gln Gln Ser Phe Pro Ile
1985                1990                1995

Arg Trp Glu Ala Val Ser Val Lys Gly Gly Tyr Lys Gln Lys Trp
2000                2005                2010

Ser Thr Arg Gly Asp Gly Leu Pro Lys Asp Thr Arg Ile Ser Asp
2015                2020                2025

Ser Leu Ala Pro Ile Gly Asn Trp Ile Arg Ser Leu Glu Leu Val
2030                2035                2040

Arg Asn Gln Val Arg Leu Asn Pro Phe Asn Glu Ile Leu Phe Asn
2045                2050                2055

Gln Leu Cys Arg Thr Val Asp Asn His Leu Lys Trp Ser Asn Leu
2060                2065                2070

Arg Arg Asn Thr Gly Met Ile Glu Trp Ile Asn Arg Arg Ile Ser
2075                2080                2085

Lys Glu Asp Arg Ser Ile Leu Met Leu Lys Ser Asp Leu His Glu
2090                2095                2100

Glu Asn Ser Trp Arg Asp
2105

<210> SEQ ID NO 10
<211> LENGTH: 229
<212> TYPE: PRT
<213> ORGANISM: Vesicular stomatitis virus

<400> SEQUENCE: 10

Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Ser
                20                  25                  30

Met Glu Tyr Ala Pro Ser Ala Pro Ile Asp Lys Ser Tyr Phe Gly Val
```

```
                35                  40                  45
Asp Glu Met Asp Thr Tyr Asp Pro Asn Gln Leu Arg Tyr Glu Lys Phe
 50                  55                  60

Phe Phe Thr Val Lys Met Thr Val Arg Ser Asn Arg Pro Phe Arg Thr
 65                  70                  75                  80

Tyr Ser Asp Val Ala Ala Val Ser His Trp Asp His Met Tyr Ile
                 85                  90                  95

Gly Met Ala Gly Lys Arg Pro Phe Tyr Lys Ile Leu Ala Phe Leu Gly
                100                 105                 110

Ser Ser Asn Leu Lys Ala Thr Pro Ala Val Leu Ala Asp Gln Gly Gln
                115                 120                 125

Pro Glu Tyr His Ala His Cys Glu Gly Arg Ala Tyr Leu Pro His Arg
                130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
                180                 185                 190

Phe Asn Ser Ser Lys Phe Ser Asp Phe Arg Glu Lys Ala Leu Met Phe
                195                 200                 205

Gly Leu Ile Val Glu Lys Lys Ala Ser Gly Ala Trp Val Leu Asp Ser
210                 215                 220

Ile Gly His Phe Lys
225

<210> SEQ ID NO 11
<211> LENGTH: 498
<212> TYPE: PRT
<213> ORGANISM: Lymphocytic choriomeningitis mammarenavirus

<400> SEQUENCE: 11

Met Gly Gln Ile Val Thr Met Phe Glu Ala Leu Pro His Ile Ile Asp
 1               5                  10                  15

Glu Val Ile Asn Ile Val Ile Val Leu Ile Ile Ile Thr Ser Ile
                 20                  25                  30

Lys Ala Val Tyr Asn Phe Ala Thr Cys Gly Ile Leu Ala Leu Val Ser
                 35                  40                  45

Phe Leu Phe Leu Ala Gly Arg Ser Cys Gly Met Tyr Gly Leu Asn Gly
 50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Ala Asn Asn
                 85                  90                  95

Ser His His Tyr Ile Ser Met Gly Ser Ser Gly Leu Glu Leu Thr Phe
                100                 105                 110

Thr Asn Asp Ser Ile Leu Asn His Asn Phe Cys Asn Leu Thr Ser Ala
                115                 120                 125

Phe Asn Lys Lys Thr Phe Asp His Thr Leu Met Ser Ile Val Ser Ser
                130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175
```

```
Pro Gln Ser Ala Ile Ser Gln Cys Arg Thr Phe Arg Gly Arg Val Leu
                180                 185                 190

Asp Met Phe Arg Thr Ala Phe Gly Gly Lys Tyr Met Arg Ser Gly Trp
            195                 200                 205

Gly Trp Ala Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg

<210> SEQ ID NO 12
<211> LENGTH: 498
<212> TYPE: PRT
<213> ORGANISM: Dandenong virus

<400> SEQUENCE: 12

Met Gly Gln Leu Ile Thr Met Phe Glu Ala Leu Pro His Ile Ile Asp
1               5                   10                  15

Glu Val Ile Asn Ile Val Ile Ile Val Leu Val Ile Ile Thr Ser Ile
                20                  25                  30

Lys Ala Val Tyr Asn Phe Ala Thr Cys Gly Ile Ile Ala Leu Ile Ser
            35                  40                  45
```

-continued

```
Phe Cys Leu Leu Ala Gly Arg Ser Cys Gly Leu Tyr Gly Val Thr Gly
 50                  55                  60

Pro Asp Ile Tyr Lys Gly Leu Tyr Gln Phe Lys Ser Val Glu Phe Asn
 65                  70                  75                  80

Met Ser Gln Leu Asn Leu Thr Met Pro Asn Ala Cys Ser Ala Asn Asn
                 85                  90                  95

Ser His His Tyr Ile Ser Met Gly Lys Ser Gly Leu Glu Leu Thr Phe
                100                 105                 110

Thr Asn Asp Ser Ile Ile Ser His Asn Phe Cys Asn Leu Thr Asp Gly
            115                 120                 125

Phe Lys Lys Lys Thr Phe Asp His Thr Leu Met Ser Ile Val Ala Ser
130                 135                 140

Leu His Leu Ser Ile Arg Gly Asn Thr Asn Tyr Lys Ala Val Ser Cys
145                 150                 155                 160

Asp Phe Asn Asn Gly Ile Thr Ile Gln Tyr Asn Leu Ser Phe Ser Asp
                165                 170                 175

Ala Gln Ser Ala Ile Asn Gln Cys Arg Thr Phe Arg Gly Arg Val Leu
            180                 185                 190

Asp Met Phe Arg Thr Ala Phe Gly Gly Lys Tyr Met Arg Ser Gly Tyr
        195                 200                 205

Gly Trp Lys Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Glu
225                 230                 235                 240

Tyr Ala Gly Pro Phe Gly Leu Ser Arg Val Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Thr Glu Asn Pro Gly Gly Tyr Cys Leu Thr Lys
        275                 280                 285

Trp Met Leu Ile Ala Ala Glu Leu Lys Cys Phe Gly Asn Thr Ala Val
    290                 295                 300

Ala Lys Cys Asn Ile Asn His Asp Glu Glu Phe Cys Asp Met Leu Arg
305                 310                 315                 320

Leu Ile Asp Tyr Asn Lys Ala Ala Leu Lys Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Val Lys Thr Gly
    370                 375                 380

Asp Thr Ser Val Pro Lys Cys Trp Leu Val Ser Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Val Phe Leu His Leu Met Lys Ile Pro Thr His Arg His Ile
    450                 455                 460

Lys Gly Gly Thr Cys Pro Lys Pro His Arg Leu Thr Ser Lys Gly Ile
```

```
                465                 470                 475                 480
Cys Ser Cys Gly Ala Phe Lys Val Pro Gly Val Lys Thr Val Trp Lys
                    485                 490                 495
Arg Arg

<210> SEQ ID NO 13
<211> LENGTH: 489
<212> TYPE: PRT
<213> ORGANISM: Mopeia mammarenavirus

<400> SEQUENCE: 13

Met Gly Gln Ile Val Thr Phe Phe Gln Glu Val Pro His Ile Leu Glu
1               5                   10                  15

Glu Val Met Asn Ile Val Leu Met Thr Leu Ser Ile Leu Ala Ile Leu
                20                  25                  30

Lys Gly Ile Tyr Asn Val Met Thr Cys Gly Ile Ile Gly Leu Ile Thr
            35                  40                  45

Phe Leu Phe Leu Cys Gly Arg Ser Cys Ser Ser Ile Tyr Lys Asp Asn
50                  55                  60

Tyr Glu Phe Phe Ser Leu Asp Leu Asp Met Ser Ser Leu Asn Ala Thr
65                  70                  75                  80

Met Pro Leu Ser Cys Ser Lys Asn Asn Ser His His Tyr Ile Gln Val
                85                  90                  95

Gly Asn Glu Thr Gly Leu Glu Leu Thr Leu Thr Asn Thr Ser Ile Ile
            100                 105                 110

Asp His Lys Phe Cys Asn Leu Ser Asp Ala His Arg Arg Asn Leu Tyr
        115                 120                 125

Asp Lys Ala Leu Met Ser Ile Leu Thr Thr Phe His Leu Ser Ile Pro
130                 135                 140

Asp Phe Asn Gln Tyr Glu Ala Met Ser Cys Asp Phe Asn Gly Gly Lys
145                 150                 155                 160

Ile Ser Ile Gln Tyr Asn Leu Ser His Ser Asn Tyr Val Asp Ala Gly
                165                 170                 175

Asn His Cys Gly Thr Ile Ala Asn Gly Ile Met Asp Val Phe Arg Arg
            180                 185                 190

Met Tyr Trp Ser Thr Ser Leu Ser Val Ala Ser Asp Ile Ser Gly Thr
        195                 200                 205

Gln Cys Ile Gln Thr Asp Tyr Lys Tyr Leu Ile Ile Gln Asn Thr Ser
    210                 215                 220

Trp Glu Asp His Cys Met Phe Ser Arg Pro Ser Pro Met Gly Phe Leu
225                 230                 235                 240

Ser Leu Leu Ser Gln Arg Thr Arg Asn Phe Tyr Ile Ser Arg Arg Leu
                245                 250                 255

Leu Gly Leu Phe Thr Trp Thr Leu Ser Asp Ser Glu Gly Asn Asp Met
            260                 265                 270

Pro Gly Gly Tyr Cys Leu Thr Arg Ser Met Leu Ile Gly Leu Asp Leu
        275                 280                 285

Lys Cys Phe Gly Asn Thr Ala Ile Ala Lys Cys Asn Gln Ala His Asp
    290                 295                 300

Glu Glu Phe Cys Asp Met Leu Arg Leu Phe Asp Phe Asn Lys Gln Ala
305                 310                 315                 320

Ile Ser Lys Leu Arg Ser Glu Val Gln Gln Ser Ile Asn Leu Ile Asn
                325                 330                 335

Lys Ala Val Asn Ala Leu Ile Asn Asp Gln Leu Val Met Arg Asn His
```

```
                  340                 345                 350
Leu Arg Asp Leu Met Gly Ile Pro Tyr Cys Asn Tyr Ser Lys Phe Trp
            355                 360                 365

Tyr Leu Asn Asp Thr Arg Thr Gly Arg Thr Ser Leu Pro Lys Cys Trp
        370                 375                 380

Leu Val Thr Asn Gly Ser Tyr Leu Asn Glu Thr Gln Phe Ser Thr Glu
385                 390                 395                 400

Ile Glu Gln Glu Ala Asn Asn Met Phe Thr Asp Met Leu Arg Lys Glu
                405                 410                 415

Tyr Glu Lys Arg Gln Ser Thr Thr Pro Leu Gly Leu Val Asp Leu Phe
            420                 425                 430

Val Phe Ser Thr Ser Phe Tyr Leu Ile Ser Val Phe Leu His Leu Ile
        435                 440                 445

Lys Ile Pro Thr His Arg His Ile Lys Gly Lys Pro Cys Pro Lys Pro
    450                 455                 460

His Arg Leu Asn His Met Ala Ile Cys Ser Cys Gly Phe Tyr Lys Gln
465                 470                 475                 480

Pro Gly Leu Pro Thr Gln Trp Lys Arg
                485
```

<210> SEQ ID NO 14
<211> LENGTH: 446
<212> TYPE: PRT
<213> ORGANISM: Homo sapiens

<400> SEQUENCE: 14

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 15
<211> LENGTH: 218
<212> TYPE: PRT
<213> ORGANISM: Homo sapiens

<400> SEQUENCE: 15

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 16
<211> LENGTH: 446
<212> TYPE: PRT
<213> ORGANISM: Homo sapiens

<400> SEQUENCE: 16

Glu Val Met Leu Val Glu Ser Gly Gly Gly Leu Val Gln Pro Gly Gly
1               5                   10                  15
Ser Leu Arg Leu Ser Cys Thr Ala Ser Gly Phe Thr Phe Ser Ala Ser
            20                  25                  30
Ala Met Ser Trp Val Arg Gln Ala Pro Gly Lys Gly Leu Glu Trp Val
        35                  40                  45
Ala Tyr Ile Ser Gly Gly Gly Asp Thr Tyr Tyr Ser Ser Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg His Ser Asn Pro Asn Tyr Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
```

```
                305                 310                 315                 320
        Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Gln Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                        420                 425                 430

His Asn His Tyr Thr Gln Lys Ser Leu Ser Leu Ser Leu Gly
                        435                 440                 445

<210> SEQ ID NO 17
<211> LENGTH: 218
<212> TYPE: PRT
<213> ORGANISM: Homo sapiens

<400> SEQUENCE: 17

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
                20                  25                  30

Gly Ile Ser Phe Met Asn Trp Tyr Gln Gln Lys Pro Gly Gln Ala Pro
            35                  40                  45

Lys Leu Leu Ile Tyr Val Ala Ser Asn Gln Gly Ser Gly Ile Pro Ala
        50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 18
<211> LENGTH: 446
```

```
<212> TYPE: PRT
<213> ORGANISM: Homo sapiens

<400> SEQUENCE: 18
```

| | | | | | | | | | | | | | | | |
|---|---|---|---|---|---|---|---|---|---|---|---|---|---|---|---|
| Glu | Val | Met | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Thr | Ala | Ser | Gly | Phe | Thr | Phe | Ser | Lys | Ser |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ala | Tyr | Ile | Ser | Gly | Gly | Gly | Asp | Thr | Tyr | Tyr | Ser | Ser | Val |
| | 50 | | | | | 55 | | | | | 60 | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | His | Ser | Asn | Val | Asn | Tyr | Tyr | Ala | Met | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Cys | Ser | Arg | Ser | Thr | Ser | Glu | Ser | Thr | Ala | Ala |
| | | 130 | | | | | 135 | | | | | 140 | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | | 180 | | | | | 185 | | | | | 190 | |
| Ser | Ser | Ser | Leu | Gly | Thr | Lys | Thr | Tyr | Thr | Cys | Asn | Val | Asp | His | Lys |
| | | | | 195 | | | | | 200 | | | | | 205 | |
| Pro | Ser | Asn | Thr | Lys | Val | Asp | Lys | Arg | Val | Glu | Ser | Lys | Tyr | Gly | Pro |
| | | | 210 | | | | | 215 | | | | | 220 | | |
| Pro | Cys | Pro | Pro | Cys | Pro | Ala | Pro | Glu | Phe | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | Gln | Glu | Asp | Pro | Glu |
| | | | 260 | | | | | 265 | | | | | 270 | | |
| Val | Gln | Phe | Asn | Trp | Tyr | Val | Asp | Gly | Val | Glu | Val | His | Asn | Ala | Lys |
| | | | 275 | | | | | 280 | | | | | 285 | | |
| Thr | Lys | Pro | Arg | Glu | Glu | Gln | Phe | Asn | Ser | Thr | Tyr | Arg | Val | Val | Ser |
| | | 290 | | | | | 295 | | | | | 300 | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Gly | Leu | Pro | Ser | Ser | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | | 340 | | | | | 345 | | | | | 350 | |
| Pro | Ser | Gln | Glu | Glu | Met | Thr | Lys | Asn | Gln | Val | Ser | Leu | Thr | Cys | Leu |
| | | | | 355 | | | | | 360 | | | | | 365 | |
| Val | Lys | Gly | Phe | Tyr | Pro | Ser | Asp | Ile | Ala | Val | Glu | Trp | Glu | Ser | Asn |
| | | | 370 | | | | | 375 | | | | | 380 | | |
| Gly | Gln | Pro | Glu | Asn | Asn | Tyr | Lys | Thr | Thr | Pro | Pro | Val | Leu | Asp | Ser |
| 385 | | | | | 390 | | | | | 395 | | | | | 400 |

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly
    435                 440                 445

<210> SEQ ID NO 19
<211> LENGTH: 218
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 446
<212> TYPE: PRT
<213> ORGANISM: Homo sapiens

<400> SEQUENCE: 20

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 21
<211> LENGTH: 218
<212> TYPE: PRT
<213> ORGANISM: Homo sapiens

```
<400> SEQUENCE: 21

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 22
<211> LENGTH: 446
<212> TYPE: PRT
<213> ORGANISM: Homo sapiens

<400> SEQUENCE: 22

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

-continued

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 23
<211> LENGTH: 218
<212> TYPE: PRT
<213> ORGANISM: Homo sapiens

<400> SEQUENCE: 23

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

```
Arg Leu Glu Pro Glu Asp Phe Ala Val Tyr Tyr Cys Gln Gln Ser Lys
                85                  90                  95
Glu Val Pro Trp Thr Phe Gly Gln Gly Thr Lys Leu Glu Ile Lys Arg
               100                 105                 110
Thr Val Ala Ala Pro Ser Val Phe Ile Phe Pro Pro Ser Asp Glu Gln
           115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 24
<211> LENGTH: 12603
<212> TYPE: RNA
<213> ORGANISM: Vesicular stomatitis virus

<400> SEQUENCE: 24

```
ugcuucuguu uguuugguaa uaauaguaau uuuccgaguc cucuuugaaa uugucauuag      60
uuuuacagac aaugucaguu cucuuaguaa cuguugaguc agcaucaagg uuugaagga     120
cguuuacucc uaggucaccu uaugggccgu cuaaugaagu cuuuuaguuu ccucuaagga    180
gaaauguagu uaugauguuu ucaaacaguu cuagauucuc cuauacagau gguuccggag    240
uuuaggccuu uacauaguua guaugucag ugucgauga acauaccucg uaauuuccug      300
uaggccccau ucaaccuauu cuaaccagu ucaaagccuu auuuguagcc cuucguccc      360
cuauguuagc cuuauaaacu ggaacauagg aacuuucggg accugccgca ugaaggucua    420
ccucauagcc uacgaagguc uuggucgcgu cuacuguuua ccaacggaaa cauagaugaa    480
ccgaauaugu cucacccguc uuguguuuac ggacuuaugu cuuuuuucga guaccuaccc    540
gacuguuuag uuacguuuua cuaguuacuu gucaaacuug gagaacacgg ucuuccagca    600
cuguaaaaac uacacacccc uuuacuguca uuaauguguu uuuaacagcg acgucaccug    660
uacaagaagg uguacaaguu uuuuguacuu acacggagca agucuaugcc uugauaacaa    720
aggucuaagu uucuaacacg acguaaccgu uguaaaccug uggagacguu uuauuggccu    780
uacagauguc uucuacauug cuggaccuag aacuuggcuc uucaacgucu acuuuaccag    840
guuuacuacg aagguccggu ucuuuaacg uuccggcuaa guauguacgg aauaaacuag    900
cugaaaccua acagaagauu cagagguaua agaaggcagu uuugggacg gaaggugaag     960
accccccguua acugucgaga agacgagucu aggugguuc guuccuuacg ggcugucgga  1020
cuacuguaac ucauauguag agaaugaugu cguccaaaca acaugcgaau acgucauccu  1080
aggagacggc ugaaccgugu ugucaaaaca caaccucuau uguuuaugug aggucuacua  1140
ucauggccuc cuaacugcug auuacggggc ggugguuccgu cucuacacca gcuuaccgag  1200
ccuaccaaac uucuaguuuu gucuuuuggc ugaggacuau acuacgucau acgcuuuucu  1260
cgucaguaca gugacguucc ggauucucuc uucuguuaac cguucauacg auucagucuu  1320
```

```
aaacuguuua cugggauauu aagagucuag uggauaauau auaauacgau guauacuuuu    1380
uuugauuguc uauaguaccu auuagagugu uuucaagcac ucauagaguu caggauaaga    1440
gcagaccuag uccgccaucc ucucuaucua cucuagcuuc guguugcucg acuuuucagg    1500
uuaauacuca acaagguucu ccuaccucac cuucucguau gauucgggag aauaaaaguc    1560
cgucgucuac uaagacugug ucuuagacuu ggucuuuaac uucguuagu ccgaacaua      1620 cguggucuag gucuucgacu cguucaacuu ccgaaauaug uccccggaaa uacugaua     1680 cgucuacucc uucaccuaca acauaaauga agccugaccu uugucggacu cgaacuuaga    1740
cugcucguac cuuucuggaa ugccaacugu agcggucucc caaauucacc ucucgucuuu    1800
agggucaccg aaagcugcua auuucgucag cacguuucac gguuaugac cuuagaccgu     1860 cucacgugua aacuucguag ccccuuuccc caguaauacu uccucgcggu cuauugaggc    1920
cuacauauau uccagugagg ucacuacuug uguaggca gggguuagucu ucgucauagu     1980 cuacaaacca gagagaguuu cuguaggac ugaaagguug gguucuuucg uucagaaguc    2040
ggagaguggu auaggaaccu acuuaacaag aguagaucuc cucucaagua gagacagccu    2100
ccacugccug cuuacagagu auuucuccgg uaggacgagc cggacucuau guuuucaac    2160 auguuaguc gcucucaguu uauaagagac aucgauacu uuuuucauu gucuauagug      2220 cuagauucac aauaggguua gguaaguagu acucaaggaa uuucuucuaa gagccagacu    2280 ucccuuucc auucuuuaga uucuuuaauc ccuagcgugg ugggggaaua cuucuccugu    2340
gaucguaccu cauacgaggc ucgcgagguu aacuguuuag gauaaaaccu caacugcucu    2400 accguggau acuaggcuua guuaauucua uacucuuuaa gaagaaaugu cacuuuuacu     2460
gccaaucuag auuagcaggc aagucuugua ugagucuaca ccgucggcga cauaggguaa    2520
cccuagugua cauguagccu uaccgucccu uugcaggaa gauguuuag aaccgaaaaa     2580 acccaagaag auuagauuuc cggugaqguc gccauaaccg ucuaguucca guugucuca    2640 uagugcgagu gacgcuuccg ucccgaauaa acguguauc cuacccccuuc uggggagggu    2700 acgaguuaca uggucucgug aagucuucug guaaguauua uccagaaaug uucccuugcu    2760
aacucgagug uuacuggouag augcuacuac ucagugaccu cgucgagga acuagaccc     2820 uaguaaaguu aagaagguuu aaaagacuaa agucucucuu ccggaauuac aaaccggacu    2880
aacagcucuu uuuccguaga ccucgcaccc aggaccugga auagccgug aaguuuacuc     2940 gaucagauug aagaucgaag acuuguuagg ggccaaauga gucagagggg auuaaggucg    3000
gagagcuugu ugauuauagg acagaaaaga uagggauacu uuuuuugauu gucucuagcu    3060
agacaaaugc gcagugccua gggggcccga cguccuuaag cggguguacc cggucuagca    3120
cugguacaag cuccgggacg ggguguagua gcugcuccac uaguuguagc acuaguagca    3180
cgaguaguag uaggugucgu aguccggca cauguugaag cgguggacgc cguaggaccg     3240
ggaccacucg aaggacaagg accggccguc uucgacgccg uacaugccgg acuuaccggg    3300
gcuauagaug uucccgcaca uggucaaguu cucgcaccuc aagcuguacu cgguggacuu    3360
ggagugguac ggguugcgga cgucgcgguu guuaucggug ugaugua gu cguacccguc    3420 gucgccggac cucaacugga aguguugcu cguaggac uugguguuga agacguugga      3480 gggucgcgg aaguuguucu uuuggaagcu gguguggag uacucuagc acucgucgga      3540 cguggacucg uagucccgu ugucguuggu guuccggcac ucgacgcuga aguuguugcc    3600 guaguggag gucauguugg acucgaaguc gcuaggaguc ucgcgguagu cggucacguc    3660
```

| | | | | | |
|---|---|---|---|---|---|
| uuggaagucu | ccgucucacg | accuguacaa | gucuuggcgg | aagccgccgu | ucauguacuc | 3720 |
| uucgccgacc | ccgacccggc | cgucgcugcc | guucuggugg | accacgucgg | ucggucgau | 3780 |
| ggucauggag | uaguaggucu | ugucuuggac | ccucuuggug | acgucuaugc | ggccuggaaa | 3840 |
| gccguacucg | ucuuaggaca | agcggguccu | cuuuugguuc | aaggaguggu | ccucugaccg | 3900 |
| gccguggaag | uggaccuggg | acucgcuguc | gucgccgcac | cucuugggac | cgccgaugac | 3960 |
| ggagugguuc | accuacuagg | accggcggcu | cgacuuacg | aagccguugu | ggcggcaccg | 4020 |
| guucacguug | cacuuggugc | ugcuccucaa | gacgcuguac | gacucugagu | agcugauguu | 4080 |
| guuccggcgg | gacucguuca | aguucguccu | gcaccucucg | cgggacgugc | acaaguucug | 4140 |
| guggcacuug | ucggaguagu | cgcuggucga | cgaguacucu | uggugacu | cucuggagua | 4200 |
| cccgcacggg | augacguuga | ugucguucaa | gaccauagac | cucgugcggu | ucuggccgcu | 4260 |
| cuggucgcac | ggguucacga | ccgaccacug | guuaccgucg | auggacuugc | ucugggugaa | 4320 |
| gucgcugguc | uagcucgucc | uucggcuguu | guacuagugg | cucuacgacu | ccuuccugau | 4380 |
| guaguucucu | gucccgucgu | gggggaccg | ggaguaccua | gacgaguaca | agucgggguc | 4440 |
| gcggauggag | uagucguaga | aggacgugga | ccacuucuag | gggugggugu | cuguguaguu | 4500 |
| cccgccgucg | acggguucg | gggugucuga | guggguguuc | ccguagacgu | cgacgccgcg | 4560 |
| gaaguuccac | gggccgcacu | uuugguagac | cuucccucu | auucgccggc | gaugcuggag | 4620 |
| cugauacuuu | uuuugauugu | cuauaggagc | ugcgguggua | cccggugugu | ucuuccgucc | 4680 |
| cuuguucggg | gucguucacg | gggauggacu | ugaagaaagu | cgacgaccac | gaccggccgg | 4740 |
| acucggugaa | aacaagaccg | cacuaggugc | acugguuucu | ucacuuucuc | cagcggugug | 4800 |
| acucgacgcc | ggguugcaa | agucaccuuc | uugaccgggu | cuggucuuag | augaccgucu | 4860 |
| uucuuuucuu | uuaccacgac | uguacuacu | cgccgcugua | cuuguagacc | gggcucaugu | 4920 |
| ucuuggccug | guagaagcug | uaguggugu | uggacucgua | gcacuaagac | cgggacuccg | 4980 |
| gaagacuacu | cccgguggaua | cucacgcacc | acgacuucau | gcucuuccug | cggaaguucg | 5040 |
| cgcucguaga | ccggcuucac | ugugacucgc | acuuccggcu | gaaagggugu | ggaucguagu | 5100 |
| cgcugaagcu | cuaggggugg | ucguuguagu | cugccuagua | gacaucgugg | ucgccgccga | 5160 |
| aaggucucgg | aguagacaga | accgaccuuu | ugccgcuccu | ugacuugcgg | uaguuguggu | 5220 |
| ggcacagagu | ccuggggcuc | ugucucgaca | uacggcacag | gucuucgac | cugaaguugu | 5280 |
| acuggugguu | ggugucgaag | uacacggacu | aauucaugcc | ggggacucu | cacuuggucu | 5340 |
| ggaaguugac | cuuguggugg | uucguucucg | ugaaggggcu | gcuguucugg | gugugggacag | 5400 |
| gagguacagg | acgaggucuu | gacgagccgc | cugggaggca | caaagacaag | ggagguuucg | 5460 |
| gauuccugug | ggacuacuag | ucgcuugggg | gacuucacug | gacgcaccac | caccuacaca | 5520 |
| gagugcuccu | gggucuucac | uucaaguuaa | ccaugcaccu | gccgcaccuu | cacguguugc | 5580 |
| gguucugguu | cggaucucuc | cuugucaugu | ugcgugggau | gucucaccac | aggcacgacu | 5640 |
| ggcacgacgu | aguccugacc | gacuugccgu | uucaugu | cacguccac | agguuguucc | 5700 |
| gggacggacg | aggauagcuc | uuuugguagu | cguuccgguu | cccgucggg | gcccuuggag | 5760 |
| uucacauaug | ggacggagga | ucggcccuuc | ucuacugguu | cuuagccac | agggacugga | 5820 |
| cggagcacuu | cccgaagaug | ggaaggcuau | agcggcaccu | uacccucucg | uuaccggucg | 5880 |
| gacucuuguu | gauguucgu | uggggaggac | acgaccugcu | gcugccgagu | aagaaggaca | 5940 |
| ugucguuuga | cuggcaccug | uucucgucua | ccgucguccc | guuacacaag | ucgacgcgc | 6000 |
| acuacgugcu | ccggggacgug | uuggugaugu | gggucuuuuc | ggacucggac | agaggaccga | 6060 |

```
                                                         -continued cuaguugauc ggucuaagaa guacaaaccu gguuuaguug aacacuaugg uacgaguuuc      6120
uccggaguua auauaaacuc aaaaauuaaa aauacuuuuu uugauugcg uuaguaccuu        6180 caggugcuaa aacucuggcu gcucaaguua cuaaguuac uucuacugau acgguguucu       6240
cuuaaggacu uagggcuacu cgcguacugc augaacuuag uacgacuaau guuggacuua      6300
agaggagauu aaucacuacu auaacuguua aauuagccu uuaaguuaag agaagguuaa       6360
gggagcuaca cccuaucauu cuugacccua ccucaagaac ucuacaauug caguacaguu      6420
cgguuagggu aggguuguag agcuacgua uuuaccuacc cuucaaccaa uuacagacua       6480
uuaguacuac ggucaguucc cauaucaaaa aaugcacuuc accguuucu ccgucuuuau       6540 uguaaacugc accaccucug aaguaggcg ccgaccccgu uguugguua acuuauguag        6600 uuuuuccuuu cuaccugacu gaguaaguuu uaagagcgaa uaaacacagu uuucaaaaac     6660
cugaaugugu ucaacuguaa uuagaauuua cgacagagac uccaccuuaa cgaguugaac     6720
cgcuccugaa aguuccguu ucagucuucu ucaagaguac cuugcuugua uacguccuaa      6780
ucccaagggu cgaacccagg augaaauaa agucuuccua cccgaaugaa guucuuugaa      6840
cuauaagauu accuggcuuu gaaagacaau uaccaguuuc uacacuaaua ucccuccuac     6900
guuugccacg auagguacca acaucuuau cuguuggaca agagucucgu ucuguagaag     6960
agggaagauu auagaugcuc uuaaccucua uuuuaacacc ucccgucccc uuuaaaaga    7020 auacgaacu aauuuuacca ccuuggcuau acguugaacu ucgacuacuu uaaucguucu     7080
cuuaguuccg gaaaucaggg uguuaaggga guaaaacuuu uaguauagu cugaagacaa     7140 cuacuuccc guuuuaaucu ggcuccauau ucuaaggagg uacuagcuua uuacucacac     7200
uuuugucacc uagaguguga ccacuaaaua ccuagcaagu cuguaacccc aguaggaaaa   7260
uaucuaauaa ugugaccuga ucuuuuaau guaagggyuuc auuggacuu cuuucuauaa    7320 cuacacagua uacguuucg ugaacguuca cuaaaucgag ccuaacaaga uaaaguugc    7380 aaguuacuag uauuuucac caagcacuua ccucugaacg agggaguacu aguagggaaa    7440
uuuucaguac aauuucuuuu augauaccgg ugucgacgag uucaaguucu aaaaccucua    7500
uuuaccguac uugaaggcga cuaauuaca aaacuuuaug ggcugaauga ucugggguagc   7560 uauuauauga gacuguuuuc aguaaguuac uuaccaguc uccacaacuu guacaggcu    7620 uacuuaggcu ugugaggaua gggaucauu uccacaacg ucuguacaa ccuguguuuc    7680 cgaugguuaa ccuuucuuaa agaauuucuc uaacuacucu ucccgaaucu acuacuacua     7740
gauuaauaac cagaauuucc uuccucucc cuugacuuca accgccauc uaaaagagg       7800 gauuacagaa ccuuuaacgc ucuuaugaaa cauuaauggc uuauaaacua uuucugagua    7860
aagcagggau acaaauucc ggacuguac cgccugcuag auugacguca guaauuuuc      7920 uacaaucuaa ggaguaggcc gguuccuaac uucaguauac uccguuaaac guacggguua   7980
guguaacuaa ugcuuuuuac cuuauuggug guuuccuuca auaguuugcc gggucacaag   8040
gcucaauacc cggucaagaa uccaauaggu aggaauuagc ucucuugagu acuuaaaaaa   8100
cucuuuucag aauauaugau guuaccuucu ggucugaacu acgcacaagu guuguugugu    8160
gacuaguuaa guuggagggu ugcucaaaca accguuccug uucucccacc ugaccuucca    8220
gaugccguuu uuccuaccuc auaggaguua gaugaccaau aaguuucucu ccgauuuuag   8280
ucuuugugac gacaguuuca gaaccguguu ccacauauuag uucaauaaac gugugucauua   8340 uuuugcuucu uuagcucuuu gcaacaucuu aaugcccac gagaguuagu uuaccaaaga    8400
```

-continued

```
uuauuacucu uuuaauacug acguuaguuu uaucccuguc ccuucaaucc ugaaaacuau      8460
uuacugcuac ucugaucgu uagacgucua augaacuuaa uaccuuuuua uggcuaaaag      8520
gcaccucacu aaucucccaa ucucugguuc ucuaccagug cucacugaac acaguggcua     8580
cugguuuaug ggugaacacg auuauauuac ucgagucaaa ggguguuucg agaguggcau     8640
cgaguaaaac gacucuuggg uuaguuacgg uacuauguca uguuaauaaa acccuguaaa     8700
cgaucgaga caacuacua cguacuagga cgagaagcag uuaguaacau acuucaaguu      8760
cuauucuaug gcccgaacgu gucaagauga aaguuuaugc gguacaacau aaaccuggga    8820
agguaaccuc cucacagccc guacagaaac agguccaaaa acuaaucucg gaagggucua   8880
gggcauuguc uuucagagag uaagaccucu aaguagguac augaacgagc uucacucgua   8940
gacuccucu acucacguca uaaaccuuug gggcucuauc gguucaaagc uuauugagug    9000
uaucuguucg aucaucuucu agguuggaga gacuguagc gauacccuua cucaggucgc    9060
uugaacaauu ucugaucca auuuuuacg aauuagcuua guucuguuug guaguccuug     9120
guccacuaau uccuacguug guauauaaac auaguacuuc uccagccga gucuucaaag    9180
aauaccaguu auuuaggaga caagggaucu aaaaauucac uuaaguuuag uccgugaaaa   9240
aacccucagc gucugcccga guagucagau aaaguuuuaa gagcaugaua agccuugagg    9300
aaauucuuuu ucauaguauc ccuuaaccua cuaaacuaac acuccucacu ccauaggaga   9360
aacuguguaa aucccuuuga aguaaacucu uccccuagua cauuuuacac cuguacaagu    9420
cgaugaguac gacuguguaa uucuaugguu aggaccccgg caugucaaua acccuguuga   9480
cauggguag guaaucuuua caacccaggu guuguagcuu uucucugagg aacacggugu   9540
acauugugua gucccaaguu aauacaaaga cacguaacag gucugcccua gguacugcag   9600
aaaucaagug ccccgguaa cggacgaauua gaucccagau uuuguagacu uagauguaga    9660
uaaaacgucg gaacccuuuc ccuucguuu cagggugacu aauuuucucg augugcagaa   9720
ucucuacgau agagaaccaa acaacuuggg cugagauuug aucguuacug auaugaaaga    9780
uuguaggugu gaaauugcc gcuucuuacc ugguuuccg ucguaccaa guuucuugu       9840
cccagacggag aaguauccaa aagcuguaga gccuacuccgg uaccaccaa gcguagaguc    9900
ucgugacguc guaacuggcu caacuaccgu ugaugucugu gguacucccu agacccucua    9960
gucuuaaagc ugaaaaauaa gguucguugc aacgagauac gaguuuaaug gugguggacaa    10020
cguucucugc cuaccuagug gucaacaugu cuaguaauag uauaacggac auucaggaca   10080
aacucugggu aucuucucua gugggaccug aguucauacc ugaugugcgg gggcucuacau   10140
aggguacacg acuucuguac cuccuuaccc cuuccaagca ccccguuucu cuauuuuguc    10200
uagauaggaa aucuucccuu aaccuucuua aaucgguggac gacucguuag gauaguucag    10260
ccgucuacau auccaaaaga uauaccucug aaccgcauau cuuuuagaug aguacggcuc    10320
cugucaagag auaaaggaga uagauauguu ccagcauaau cuccagcucc aaagaauuuu    10380
cccaacgauc ugccuaauua cucucguuca acgacgguuc auuaugugcc cucuucagac   10440
cgaguaaacu ucuccggccg guugcgucac augccuccaa acuaaaugaa cuaacuauuu    10500
aacucacaua guggagguaa ggaaagagaa ugaucuaguc cuggauaauc ucugcuuaau     10560
cuuugcuaag ggguguucua ggguuggagg auaggcuguu cguggcacuu auaccccccac    10620
uaacagucuu uaaugaaguu uauggguacg gcagauuaac uuuucccuuu uaugucuagu    10680
guaauaagug uuaauaccaa uaagagucua cagaauaggu aucgaaguua accugguaag    10740
agauaaaggu ggugggagaa cguuuaggau auguucggua aaaauagacc cuuucuauuc    10800
```

```
uuacucaacu cucucgaccg uuuagaaaga aguaacgauu cuaguccucu ccccacccuu    10860
cuguauguac acuuuaagaa gugguuccug uauaauaaca caggucuccu uuagucugua    10920
cgaacguuca agcccuaacg auuccuauua uuauuucugu acucgauagg gggaaccccu    10980
ucccuuaggu cucccuguua auguguuag ggacaaauaa uaugcuggug gggaaugggu    11040
uucuacgauc ucuacggagg uucuuagguu uuaggggacg acaggccuua guccaacccg    11100
guuaaugguu gaccgcgagu aauauuuuaa gccucauaua auguaccuua cccuuaggua    11160 auccccuga agaacucaac accucugccg aggccucccu acugacgacg uaaugaugcu    11220
cuuuuacacg uaucgucucc uuauaaguua ucagacaauc uuaauaguc cagucaguac    11280 gcuccgcgga gaggacucgg ggggucacgg gaucuuugaa auccuccucu auuuagcucu    11340
acacauuuac cacuuuguac aacccuuaua gguagacuga auacacuggg uuccugaacc    11400
cugauaaagg aggcugaguu ucguccgaac cccgaaguuu aacuaaauua acauuaccua    11460
uaccuucaag cccuaagaag augaucggac uuuuaacucu gcuuacaauc uuuaauacac    11520
guggccuaaa accacucgu uccucaaaau uagauguucu gaauaccuug uauauaaaca    11580
cucucgcuuu ucuuacguca uuguuaggaa ccaggguaca aguucugcca gcugaaucaa    11640
guuugucuua aaucaucaag aguuugcaga cuucauauau accauacauu uccaaacuuc    11700
uuuaauuagc uacuuggguu agggcuaacc agaagguagu uacuuaggac cuuuuuggac    11760
augcguaagg ucaguagucu uguccuuaaa cggucucguu ucuuccaauc auguaugaaa    11820
uggaacuguc cauaagggag gguuaaguaa ggacuaggaa aacauuugua acucugauac    11880
gauguuuaua agccucaugg gugcccacac agaguacgcc gacggaauuu uaguagacua    11940
ucuggacguc uaaauaacug guaaucgaa aaaauauacc gcuaauauag cauaauauug    12000
uaguuaguau agucucaucc uggcuaugga ggcuuggggg guagucuacc uuaacguguu    12060
uuacaccccu agcgauauug accauauucg aaaaccgacu caaacuaccu cuuucuguaa    12120
ggugauauag uugucacaaa ucgucaauag gucguuagua agggcuaauc cacccuccga    12180
caaagucauu uuccuccuau guucgucuuc accucaugau cuccacuacc cgagggguuu    12240
cuaugggcuu aaagucugag gaaccggggu uagcccuuga ccuagucuag agaccuuaac    12300
caggcuuugg uucaagcaga uuuaggguaag uuacucuaga acaaguuagu cgauacagca    12360
ugucaccuau uaguaaaacuu uaccaguuua aacgcuucuu uguguccuua cuaacuuacc    12420
uaguuaucug cuuaaaguuu ucuucuggcc agauaugacu acaacuucuc acuggaugug    12480
cuccuuuuga gaaccucucu aauuuuuuag uacuccucug agguuugaaa uucauacuuu    12540
uuuugaaacu aggaauucug ggagaacacc aaaaauaaaa aauagaccaa aacaccagaa    12600
gca                                                               12603
```